(12) United States Patent
Nagy et al.

(10) Patent No.: US 9,914,767 B2
(45) Date of Patent: Mar. 13, 2018

(54) **CROSS-REACTIVE *STAPHYLOCOCCUS AUREUS* ANTIBODY**

(71) Applicant: ARSANIS BIOSCIENCES GMBH, Vienna (AT)

(72) Inventors: Eszter Nagy, Vienna (AT); Adriana Badarau, Vienna (AT); Harald Rouha, Vienna (AT); Lukas Stulik, Vienna (AT); Gábor Nagy, Sopron (HU); Irina Mirkina, Vienna (AT); Zoltán Magyarics, Vienna (AT); Zehra Visram, Vienna (AT); Michaela Jaegerhofer, Vienna (AT); Manuel Zerbs, Vienna (AT); Ivana Dolezilkova, Vienna (AT); Astrid Teubenbacher, Vienna (AT); Michael Benjamin Battles, Lebanon, NH (US); Bianka Dominique Prinz, Lebanon, NH (US)

(73) Assignee: ARSANIS BIOSCIENCES GMBH, Vienna (AT)

( * ) Notice: Subject to any disclaimer, the term of this patent is extended or adjusted under 35 U.S.C. 154(b) by 0 days.

(21) Appl. No.: 14/395,259

(22) PCT Filed: Apr. 17, 2013

(86) PCT No.: PCT/EP2013/058022
§ 371 (c)(1),
(2) Date: Oct. 17, 2014

(87) PCT Pub. No.: WO2013/156534
PCT Pub. Date: Oct. 24, 2013

(65) Prior Publication Data
US 2015/0086539 A1    Mar. 26, 2015

(30) Foreign Application Priority Data

Apr. 17, 2012  (EP) .................................... 12164506
Jan. 11, 2013  (EP) .................................... 13151010

(51) Int. Cl.
| | | |
|---|---|---|
| *A61K 39/00* | (2006.01) | |
| *A61K 39/395* | (2006.01) | |
| *A61K 49/00* | (2006.01) | |
| *C07K 16/12* | (2006.01) | |
| *G01N 33/569* | (2006.01) | |
| *C07K 16/00* | (2006.01) | |
| *C07K 14/195* | (2006.01) | |

(52) U.S. Cl.
CPC ... *C07K 16/1271* (2013.01); *G01N 33/56938* (2013.01); *A61K 2039/505* (2013.01); *C07K 14/195* (2013.01); *C07K 16/00* (2013.01); *C07K 2317/21* (2013.01); *C07K 2317/33* (2013.01); *C07K 2317/76* (2013.01); *C07K 2317/92* (2013.01)

(58) Field of Classification Search
CPC .............................. C07K 16/00; C07K 14/195
USPC ....... 424/9.1, 9.2, 130.1, 136.1, 141.1, 150.1
See application file for complete search history.

(56) References Cited

U.S. PATENT DOCUMENTS

| | | |
|---|---|---|
| 6,331,415 B1 | 12/2001 | Cabilly et al. |
| 7,947,808 B2 | 5/2011 | Ohishi et al. |
| 2002/0177170 A1 | 11/2002 | Luo et al. |
| 2008/0131457 A1 | 6/2008 | Taylor et al. |

FOREIGN PATENT DOCUMENTS

| | | |
|---|---|---|
| JP | 2009-539979 A | 11/2009 |
| RU | 2007106725 A | 8/2008 |
| WO | 2003074679 A2 | 9/2003 |
| WO | 2006033700 A2 | 3/2006 |
| WO | 2008004536 A1 | 1/2008 |
| WO | 2009036379 A2 | 3/2009 |
| WO | 2010105256 A1 | 9/2010 |
| WO | 2011018208 A1 | 2/2011 |
| WO | 2011140337 A2 | 11/2011 |
| WO | 2012009568 A2 | 1/2012 |

OTHER PUBLICATIONS

Alonzo, F. et al. (2012). *Staphylococccus aureus* leukocidin ED contributes to systemic infection by targeting neutrophils and promoting bacterial growth in vivo. Molecular Microbiology, 83(2), 423-435.
Comai, Massimiliano et al. (2002). Protein engineering modulates the transport properties and ion selectivity of the pores formed by staphylococcal gamma-haemolysins in lipid membranes. Molecular Microbiology, 44(5), 1251-1267.
Dalla Serra, Mauro et al. (2005). *Staphylococcus aureus* bicomponent gamma-hemolysins, JIgA, JIgB, HIgC, and can form mixed pores containing all components. J. Chem. Inf. Model, 45(6), 1539-1545.
Dumont, A.L. et al. (2011). Characterization of a new cytotoxin that contributes to *Staphylococcus aureus* pathogenesis. Molecular Microbiology, 79(3), 814-825.
Galdiero, S. and Gouaux, E. (2004). High resolution crystallographic studies of alpha-hemolysin-phospholipid complexes define heptamer-lipid head group interactions: implication for understanding protein-lipid interactions. Protein Science, 13, 1503-1511.
Gravet, A. et al. (1998). Characterization of a novel structural member, LukE-LukD, of the bi-component staphylococcal leucotoxins family. FEBS Letters, 436, 202-208.

(Continued)

*Primary Examiner* — Rodney P Swartz
(74) *Attorney, Agent, or Firm* — Meunier Carlin & Curtman LLC

(57) ABSTRACT

The subject relates to a cross-neutralizing antibody comprising at least one polyspecific binding site that binds to alpha-toxin (Hla) and at least one of the bi-component toxins of *Staphylococcus aureus*, its medical and diagnostic use, method of producing the antibody, including an isolated nucleotide sequence, plasmids and host cells as used in the production of the antibody; and further an isolated conformational epitope recognized by a specific cross-neutralizing antibody.

21 Claims, 18 Drawing Sheets

(56) References Cited

OTHER PUBLICATIONS

Figure 2:
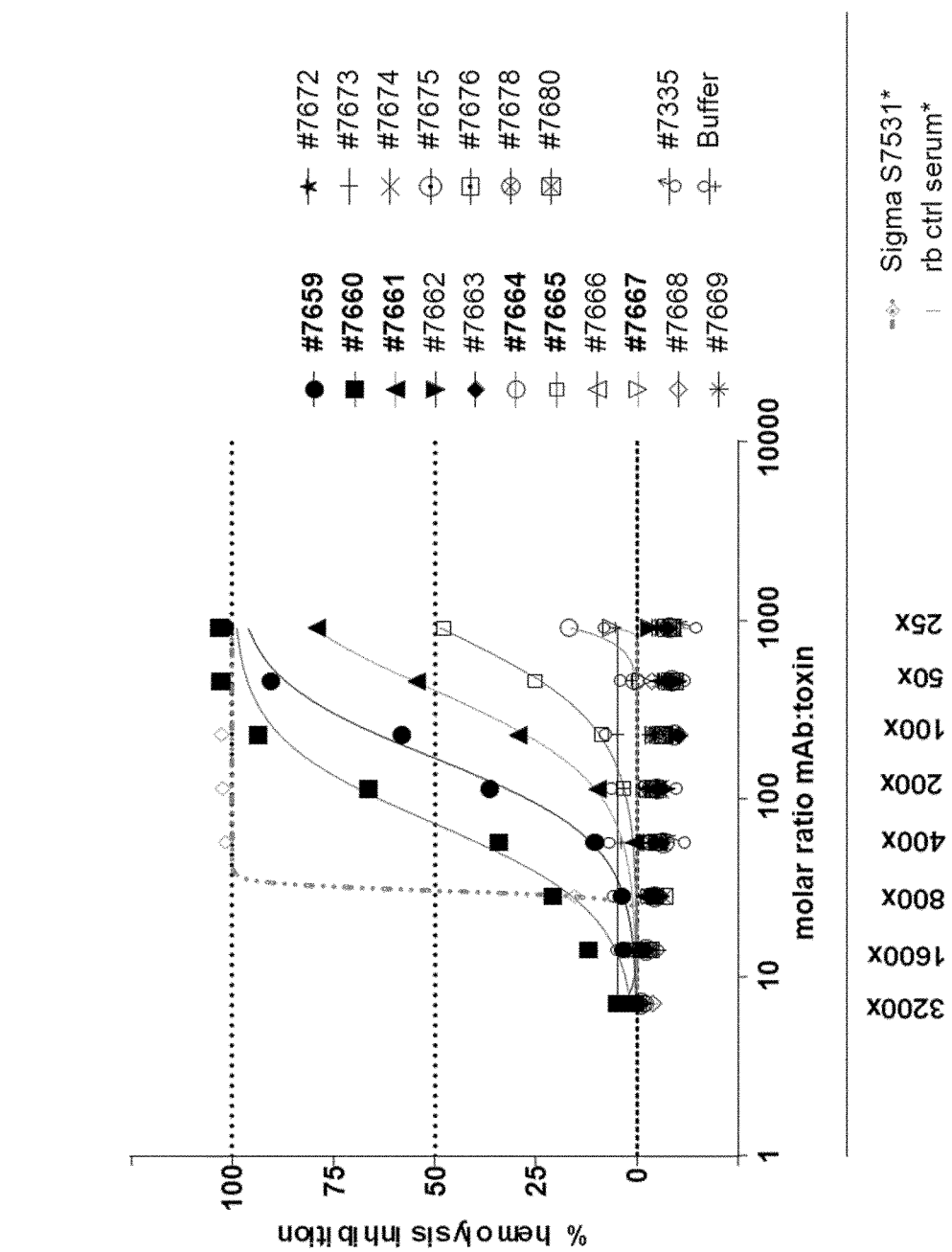
Figure 2:
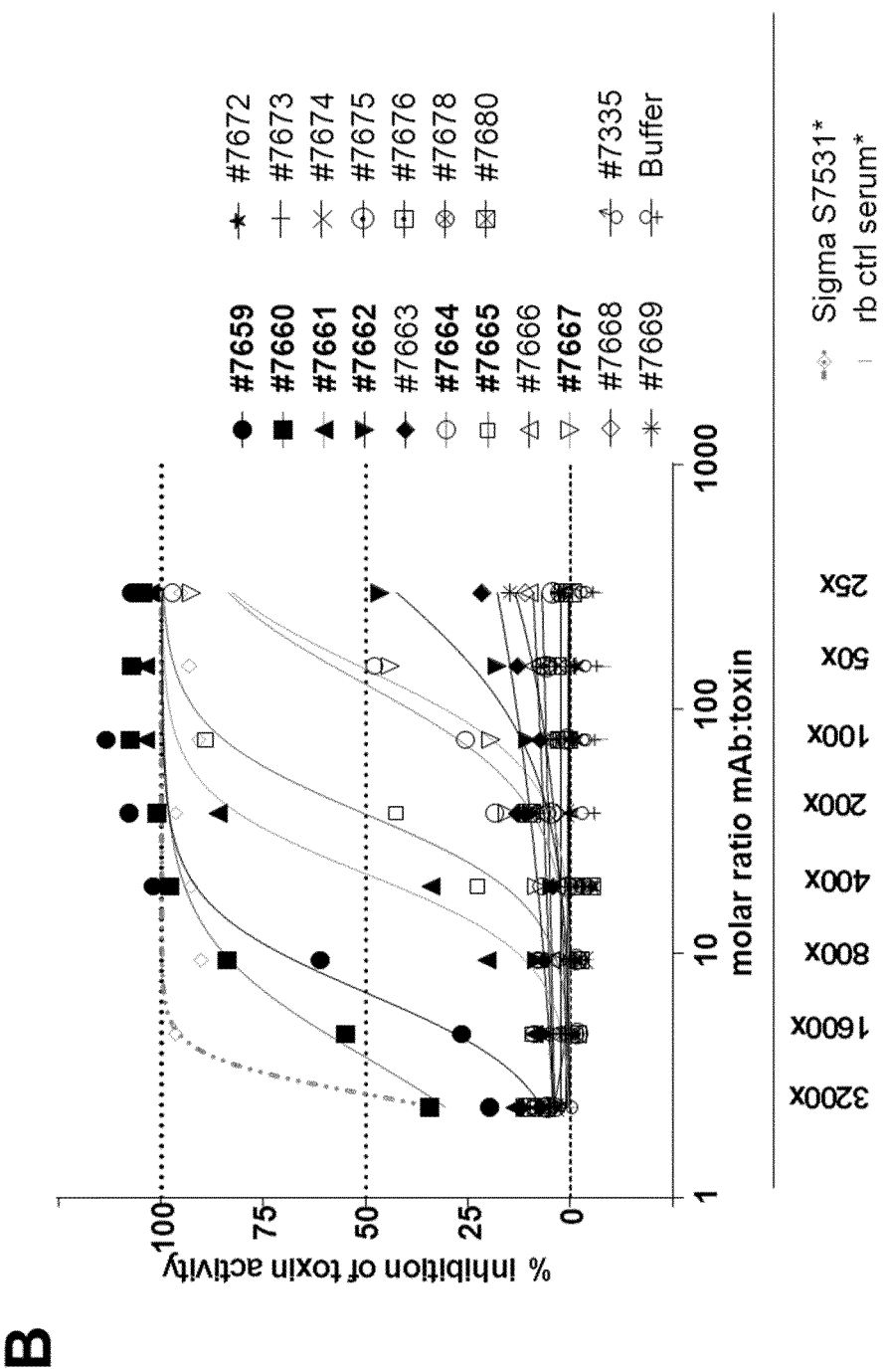

Heveker, N., et al. (1994). A human monoclonal antibody with the capacity to neutralize *Staphylococcus aureus* alpha-toxin. Hum. Antibod. Hybridomas, 5(1-2), 18-24.
Kaneko, J. and Kamio, Y. (2004). Bacterial two-component and hetero-heptameric pore-forming cytolytic toxins: structures, pore-forming mechanism, and organization of the genes. Biosci. Biotechnol. Biochem., 68(5), 981-1003.
Kobayashi, S.D. et al. (2011). Comparative analysis of USA300 virulence determinants in a rabbit model of skin and soft tissue infection. Journal of Infectious Diseases, 204, 937-941.
Kohler, G. and Milstein, C. (1975). Continuous cultures of fused cells secreting antibody of predefined specificity. Nature, 256, 495-497.
Kozbor, D. et al. (1984). A human hybrid myeloma for production of human monoclonal antibodies. Journal of Immunology, 133(6), 3001-3005.
Laventie, B.-J., et al. (2011). Heavy chain-only antibodies and tetravalent bispecific antibody neutralizing *Staphylococcus aureus* leukotoxins. Proceedings of the National Academy of Sciences of the United States of America, 108(39), 16404-16409.
Lee, M-H. and Kwak, J-W. (2003). Expression and functional reconstitution of a recombinant antibody (Fab') specific for human apolipoprotein B-100. Journal of Biotechnology, 101, 189-198.
Lina, G. et al. (1999). Involvement of panton-valentine leukocidin-producing *Staphylococcus aureus* in primary skin infections and pneumonia. Clinical Infectious Diseases, 29, 1128-1132.
Malachowa, N. et al. (2011). Global changes in *Staphylococcus aureus* gene expression in human blood. PLoS One, 6(4), e18617. doi: 10.1371/journal.pone.0018617.
Menestrina, G. et al. (2003). Ion channels and bacterial infection: the case of beta-barrel pore-forming protein toxins of *Staphylococcus aureus*. FEBS Letters, 552, 54-60.
Ohlsen, K., and Lorenz, U. (2010). Immunotherapeutic strategies to combat staphylococcal infections. International Journal of Medical Microbiology, 300(6), 402-410.
Pedelacq, J-D. et al. (1999). The structure of a *Staphylococcus aureus* leucocidin component (LukF-PV) reveals the fold of the water-soluble species of a family of transmembrane pore-forming toxins. Structure, 7(3), 277-287.
Prassler, J. et al. (2009). In vitro affinity maturation of HuCAL antibodies: complementarity determining region exchange and RapMAT technology. Immunotherapy, 1(4), 571-583.
Ragle, B.E. et al. (2010). Prevention and treatment of *Staphylococcus aureus* pneumonia with a beta-cyclodextrin derivative. Antimicrobial Agents and Chemotherapy, 54(1), 298-304.
Ragle, B. E., and Wardenburg, J. B. (2009). Anti-alpha-hemolysin monoclonal antibodies mediate protection against *Staphylococcus aureus* pneumonia. Infection and Immunity, 77(7), 2712-2718.
Sheedy, C. et al. (2007). Isolation and affinity maturation of hapten-specific antibodies. Biotechnology Advances, 25, 333-352.
Shukla, S.K. et al. (2010). Virulence genes and genotypic associations in nasal carriage, community-associated methicillin-susceptible and methicillin-resistant USA400 *Staphylococcus aureus* isolates. Journal of Clinical Microbiology, 48(10), 3582-3592.
Umana, P. et al. (1999). Engineered glycoforms of an antineuroblastoma IgG1 with optimized antibody-dependent cellular cytotoxic activity. Nature Biotechnology, 17, 176-180.
Ventura, C.L. et al. (2010). Identification of a novel *Staphylococcus aureus* two-component leukotoxin using cell surface proteomics. PLoS One, 5(7), e11634. doi:10.1371/journal.pone.0011634.
Wardenburg, J. B., and Schneewind, O. (2008). Vaccine protection against *Staphylococcus aureus* pneumonia. The Journal of Experimental Medicine, 205(2), 287-294.
Wardenburg, J.B. et al. (2008). Panton-valentine leukocidin is not a virulence determinant in murine models of community-associated methicillin-resistant *Staphylococcus aureus* disease. Journal of Infectious Disease, 198(8), 1166-1170.
Wibbenmeyer, J.A. et al. (1999). Cloning, expression, and characterization of the Fab fragment of the anti-lysozyme antibody HyHEL-5. Biochimica et Biophysica Acta, 1430, 191-202.
Yamashita, K. et al. (2011). Crystal structure of the octameric pore of staphylococcal gamma-hemolysin reveals the beta-barrel pore formation mechanism by two components. PNAS, 108(42) 17314-17319.
International Search Report and Written Opinion of the International Searching Authority, received in related application PCT/EP2013/058022, completed Jul. 30, 2013.
European Search Report, received in related application 13151010. 9, completed on Apr. 17, 2013.
Communication pursuant to Article 94(3) EPC from related Argentinian Application No. 13 728 122.6-1403, dated Apr. 22, 2014.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody", J Immunol., 2002, vol. 169, N. 6, pp. 3076-3084.
Hanada Y., et al., "Silkworm Apolipophorin Protein Inhibits *Staphylococcus aureus* Virulence", Journal of Biological Chemistry, 2011, V.286, N.45, pp. 39360-39369.
Mulualem E., et al., "Potent Neutralization of Staphylococcal Enterotoxin B by Synergistic Action of Chimeric Antibodies", Infection and Immunity, 2010, vol. 78, No. 6 pp. 2801-2811.
Riechmann L.,et al., "Reshaping human antibodies for therapy", Nature, Mar. 24, 1988; 332(6162):323-327.
Salasia S., et al., "Genotypic characterization of *Staphylococcus aureus* isolated from bovines, humans, and food in Indonesia", J. Vet Sci., 2011, V.12, N.4, pp. 353-361.
Vajdos F. F., et al., "Comprehensive Functional Maps of the Antigen-binding Site of an Anti-ErbB2 Antibody Obtained with Shotgun Scanning Mutagenesis", J. Mol. Biol., 2002, vol. 320, pp. 415-428.

Fig. 1

Hla

HlgB

LukF

LukD

Fig. 9

SEQ ID NO: 1 Hla nucleotide sequence

GCCGACAGCGACATCAACATCAAAACGGGCACGACGGACATTGGCTCAAATACGACGGTGAAAAC
GGGCGATCTGGTTACCTATGACAAAGAAAACGGCATGCATAAAAAAGTGTTTTATAGTTTCATCGAT
GACAAAAACCACAACAAAAAACTGCTGGTCATTCGTACCAAAGGCACGATCGCAGGCCAGTATCGC
GTGTACAGCGAAGAAGGCGCTAATAAATCAGGTCTGGCATGGCCGTCGGCTTTTAAAGTTCAGCTG
CAACTGCCGGATAACGAAGTCGCGCAAATTAGCGACTATTACCCGCGTAACTCTATCGATACCAAA
GAATACATGTCTACCCTGACGTACGGCTTCAACGGTAATGTTACCGGCGATGACACGGGTAAAATT
GGCGGTCTGATCGGCGCCAACGTGAGCATTGGTCATACCCTGAAATATGTTCAGCCGGACTTTAAA
ACCATCCTGGAATCTCCGACGGATAAAAAAGTGGGCTGGAAAGTTATCTTCAACAACATGGTTAAC
CAGAACTGGGGTCCGTATGATCGTGACTCATGGAACCCGGTCTACGGCAATCAACTGTTTATGAAA
ACCCGCAACGGTTCGATGAAAGCGGCCGATAACTTCCTGGACCCGAATAAAGCGAGCTCTCTGCT
GAGTTCCGGCTTTAGTCCGGACTTCGCGACCGTGATTACGATGGATCGCAAAGCCTCCAAACAGCA
AACCAATATTGATGTCATCTATGAACGTGTGCGCGATGACTACCAGCTGCACTGGACCAGCACGAA
CTGGAAAGGTACCAATACGAAAGATAAATGGATTGACCGCTCCTCGGAACGCTACAAAATTGACTG
GGAAAAAGAAGAAATGACGAAC

SEQ ID NO: 2 Hla amino acid sequence

ADSDINIKTGTTDIGSNTTVKTGDLVTYDKENGMHKKVFYSFIDDKNHNKKLLVIRTKGTIAGQYRVYSEE
GANKSGLAWPSAFKVQLQLPDNEVAQISDYYPRNSIDTKEYMSTLTYGFNGNVTGDDTGKIGGLIGANV
SIGHTLKYVQPDFKTILESPTDKKVGWKVIFNNMVNQNWGPYDRDSWNPVYGNQLFMKTRNGSMKAA
DNFLDPNKASSLLSSGFSPDFATVITMDRKASKQQTNIDVIYERVRDDYQLHWTSTNWKGTNTKDKWID
RSSERYKIDWEKEEMTN

SEQ ID NO: 3 LukS nucleotide sequence

GACAACAACATTGAAAACATTGGTGATGGCGCAGAAGTGGTGAAACGCACGGAAGATACCTCAAGC
GATAAATGGGGTGTGACGCAGAACATTCAGTTCGATTTCGTCAAAGACAAAAAATACAACAAAGATG
CACTGATTCTGAAAATGCAAGGCTTTATCAACAGCAAAACCACGTACTACAACTACAAAAACACCGA
CCATATCAAAGCTATGCGTTGGCCGTTCCAGTACAATATCGGTCTGAAAACGAACGATCCGAATGTT
GACCTGATCAACTACCTGCCGAAAAACAAAATCGATTCAGTGAACGTTTCGCAAACCCTGGGCTAC
AATATCGGCGGTAACTTTAATAGTGGCCCGTCCACCGGCGGTAACGGTAGCTTCAACTACTCTAAA
ACGATCAGTTACAACCAGCAAAACTACATCTCTGAAGTCGAACGTCAGAACAGCAAATCTGTGCAAT
GGGGCATTAAAGCGAATTCCTTTATCACCCTCACTGGGCAAAATGTCGGGTCATGATCCGAACCTGT
TTGTGGGTTATAAACCGTACAGCCAGAACCCGCGCGATTATTTCGTTCCGGACAATGAACTGCCGC
CGCTGGTCCATTCTGGCTTTAACCCGAGTTTCATTGCAACCGTGAGCCACGAAAAAGGCTCGGGTG
ATACCAGCGAATTTGAAATCACGTATGGTCGCAATATGGACGTTACCCATGCGACGCGTCGCACCA
CGCACTATGGCAACTCCTACCTGGAAGGTTCACGTATTCACAATGCCTTCGTTAACCGCAATTACAC
GGTGAAATACGAAGTCAACTGGAAAACGCACGAAATCAAAGTGAAAGGTCATAAC

SEQ ID NO: 4 LukS amino acid sequence

DNNIENIGDGAEVVKRTEDTSSDKWGVTQNIQFDFVKDKKYNKDALILKMQGFINSKTTYYNYKNTDHIK
AMRWPFQYNIGLKTNDPNVDLINYLPKNKIDSVNVSQTLGYNIGGNFNSGPSTGGNGSFNYSKTISYNQ
QNYISEVERQNSKSVQWGIKANSFITSLGKMSGHDPNLFVGYKPYSQNPRDYFVPDNELPPLVHSGFN
PSFIATVSHEKGSGDTSEFEITYGRNMDVTHATRRTTHYGNSYLEGSRIHNAFVNRNYTVKYEVNWKTH
EIKVKGHN

Fig. 9 (continued)

SEQ ID NO: 5 LukF nucleotide sequence

GCGCAGCACATCACGCCGGTCTCCGAAAAAAAAGTTGACGACAAAATCACCCTGTATAAAACGACG
GCCACGAGCGACTCTGACAAACTGAAAATTTCTCAGATCCTGACCTTCAACTTCATCAAAGATAAAA
GTTACGATAAAGACACGCTGATTCTGAAAGCGGCCGGTAACATCTATTCTGGCTACACCAAACCGA
ATCCGAAAGACACGATCAGCTCTCAATTCTACTGGGGTTCCAAATACAACATCTCAATCAACAGTGA
TTCCAACGACTCCGTCAATGTGGTTGATTATGCACCGAAAAACCAGAATGAAGAATTCCAAGTCCAG
CAAACCGTGGGCTATAGTTACGGCGGTGACATTAACATCTCGAATGGTCTGAGCGGCGGTGGCAA
CGGCTCAAAATCGTTCAGCGAAACGATCAACTACAAACAGGAATCTTACCGTACCAGTCTGGATAA
ACGCACGAATTTCAAGAAAATTGGTTGGGACGTTGAAGCGCATAAAATCATGAACAATGGTTGGGG
CCCGTATGGCCGTGATTCTTATCACAGTACCTACGGTAACGAAATGTTTCTGGGCTCCCGCCAGTC
AAACCTGAATGCCGGTCAAAATTTCCTGGAATACCATAAAATGCCGGTTCTGAGCCGTGGTAACTTT
AATCCGGAATTCATTGGCGTCCTGTCGCGCAAACAGAACGCAGCGAAAAAATCTAAAATCACCGTG
ACGTATCAGCGTGAAATGGATCGCTACACCAACTTTTGGAATCAACTGCATTGGATCGGCAACAAC
TACAAAGATGAAAACCGTGCCACCCACACGAGCATCTACAAGTTGACTGGGAAAACCACACGGTG
AAACTGATTGATACCCAAAGTAAAGAAAAAAACCCGATGTCG

SEQ ID NO: 6 LukF amino acid sequence

AQHITPVSEKKVDDKITLYKTTATSDSDKLKISQILTFNFIKDKSYDKDTLILKAAGNIYSGYTKPNPKDTISS
QFYWGSKYNISINSDSNDSVNVVDYAPKNQNEEFQVQQTVGYSYGGDINISNGLSGGGNGSKSFSETI
NYKQESYRTSLDKRTNFKKIGWDVEAHKIMNNGWGPYGRDSYHSTYGNEMFLGSRQSNLNAGQNFLE
YHKMPVLSRGNFNPEFIGVLSRKQNAAKKSKITVTYQREMDRYTNFWNQLHWIGNNYKDENRATHTSI
YEVDWENHTVKLIDTQSKEKNPMS

SEQ ID NO: 7 LukE nucleotide sequence

AATACGAATATCGAAAATATCGGCGACGGCGCAGAAGTTATCAAACGCACGGAAGATGTCAGCAGC
AAAAAATGGGGTGTTACGCAGAATGTTCAGTTCGATTTCGTCAAAGACAAAAAATACAACAAAGATG
CACTGATTGTGAAAATGCAAGGCTTTATCAATTCTCGTACCAGTTTCTCCGACGTTAAAGGCAGTGG
TTATGAACTGACGAAACGCATGATTTGGCCGTTTCAGTACAACATCGGTCTGACCACGAAAGATCC
GAACGTTTCCCTGATCAACTACCTGCCGAAAAACAAAATCGAAACCACGGACGTCGGCCAGACCCT
GGGTTACAACATTGGCGGTAATTTTCAAAGCGCTCCGTCTATCGGCGGTAACGGCTCATTCAATTA
CTCGAAAACCATTAGCTATACGCAGAAAAGTTACGTGTCCGAAGTTGATAAACAAAACTCAAAATCG
GTCAAATGGGGCGTGAAAGCGAACGAATTTGTCACCCCGGATGGTAAAAAATCTGCCCATGACCGT
TACCTGTTTGTGCAGTCGCCGAATGGTCCGACGGGTAGCGCACGTGAATACTTTGCCCCGGATAAT
CAGCTGCCGCCGCTGGTGCAATCTGGCTTTAACCCGAGTTTCATTACCACGCTGAGCCATGAAAAA
GGCAGCTCTGATACCTCCGAATTCGAAATTTCATATGGTCGTAATCTGGACATCACCTACGCAACG
CTGTTTCCGCGTACCGGTATCTATGCAGAACGCAAACACAACGCTTTTGTTAACCGCAATTTCGTTG
TCCGCTACGAAGTGAACTGGAAAACCCATGAAATCAAAGTGAAAGGCCATAAC

SEQ ID NO: 8 LukE amino acid sequence

NTNIENIGDGAEVIKRTEDVSSKKWGVTQNVQFDFVKDKKYNKDALIVKMQGFINSRTSFSDVKGSGYE
LTKRMIWPFQYNIGLTTKDPNVSLINYLPKNKIETTDVGQTLGYNIGGNFQSAPSIGGNGSFNYSKTISYT
QKSYVSEVDKQNSKSVKWGVKANEFVTPDGKKSAHDRYLFVQSPNGPTGSAREYFAPDNQLPPLVQS
GFNPSFITTLSHEKGSSDTSEFEISYGRNLDITYATLFPRTGIYAERKHNAFVNRNFVVRYEVNWKTHEIK
VKGHN

Fig. 9 (continued)

SEQ ID NO: 9 LukD nucleotide sequence

GCCCAACACATTACGCCGGTCTCGGAAAAAAAGTGGATGACAAAATCACGCTGTATAAAACGACG
GCAACCTCAGATAACGACAAACTGAACATTAGTCAGATCCTGACCTTCAACTTCATCAAAGATAAAT
CCTACGATAAAGACACGCTGGTGCTGAAAGCGGCCGGCAACATTAATTCAGGTTACAAAAAACCGA
ACCCGAAAGACTATAATTACTCGCAGTTTTATTGGGGCGGTAAATACAACGTCAGCGTGAGCTCTG
AATCTAACGATGCAGTCAATGTGGTTGACTATGCTCCGAAAAACCAGAATGAAGAATTTCAAGTGCA
GCAAACCCTGGGCTATAGCTACGGCGGTGATATTAACATCTCAAATGGCCTGTCGGGCGGTCTGAA
CGGTTCGAAAAGCTTCTCTGAAACCATCAACTACAAACAGGAAAGCTACCGTACCACGATTGATCG
CAAAACGAACCATAAATCTATCGGCTGGGGTGTTGAAGCGCACAAAATTATGAACAATGGCTGGGG
TCCGTATGGCCGTGATTCCTATGACCCGACCTACGGTAATGAACTGTTTCTGGGCGGTCGCCAGAG
TTCCTCAAACGCGGGCCAAAATTTCCTGCCGACGCATCAGATGCCGCTGCTGGCACGTGGTAACTT
TAATCCGGAATTCATCAGTGTGCTGTCCCACAAACAAAACGATACCAAAAAATCTAAAATCAAAGTT
ACGTATCAACGTGAAATGGACCGCTACACCAACCAGTGGAATCGCCTGCATTGGGTTGGTAACAAC
TACAAAAACCAGAACACCGTTACGTTCACCTCTACGTACGAAGTCGATTGGCAAAACCATACGGTC
AAACTGATTGGCACGGACAGCAAAGAAACGAACCCGGGCGTC

SEQ ID NO: 10 LukD amino acid sequence

AQHITPVSEKKVDDKITLYKTTATSDNDKLNISQILTFNFIKDKSYDKDTLVLKAAGNINSGYKKPNPKDYN
YSQFYWGGKYNVSVSSESNDAVNVVDYAPKNQNEEFQVQQTLGYSYGGDINISNGLSGGLNGSKSFS
ETINYKQESYRTTIDRKTNHKSIGWGVEAHKIMNNGWGPYGRDSYDPTYGNELFLGGRQSSSNAGQNF
LPTHQMPLLARGNFNPEFISVLSHKQNDTKKSKIKVTYQREMDRYTNQWNRLHWVGNNYKNQNTVTFT
STYEVDWQNHTVKLIGTDSKETNPGV

SEQ ID NO: 11 HlgA nucleotide sequence

GAAAACAAAATCGAAGACATCGGCCAAGGTGCTGAAATCATCAAACGCACGCAAGACATCACGAGT
AAACGCCTGGCAATCACGCAGAATATTCAGTTCGATTTCGTGAAAGACAAAAAATACAACAAAGATG
CACTGGTGGTTAAAATGCAAGGCTTTATCAGCTCTCGTACCACGTACAGCGATCTGAAAAAATATCC
GTACATTAAACGCATGATCTGGCCGTTCCAGTACAACATCAGTCTGAAAACCAAAGATTCCAACGTG
GACCTGATTAATTACCTGCCGAAAAACAAAATCGATAGTGCGGACGTTTCCCAGAAACTGGGCTAT
AACATTGGCGGTAATTTTCAATCAGCCCGTCGATCGGCGGTAGTGGTTCCTTCAATTACTCAAAAA
CCATCTCGTACAACCAGAAAAATTACGTTACGGAAGTCGAAAGCCAAAACTCTAAAGGCGTGAAAT
GGGGTGTTAAAGCGAATTCATTTGTCACCCCGAACGGCCAGGTGTCGGCGTATGATCAGTACCTGT
TTGCACAAGACCCGACGGGTCCGGCAGCACGTGATTATTTCGTTCCGGACAATCAGCTGCCGCCG
CTGATTCAAAGCGGCTTTAACCCGTCTTTCATCACCACGCTGTCCCATGAACGTGGCAAAGGTGAT
AAAAGCGAATTTGAAATTACCTATGGTCGCAACATGGATGCAACCTATGCTTACGTTACGCGTCATC
GCCTGGCAGTCGATCGTAAACACGACGCTTTCAAAAACCGCAATGTCACCGTGAAATACGAAGTCA
ACTGGAAAACGCACGAAGTCAAAATCAAATCAATCACCCCGAAA

SEQ ID NO: 12 HlgA amino acid sequence

ENKIEDIGQGAEIIKRTQDITSKRLAITQNIQFDFVKDKKYNKDALVVKMQGFISSRTTYSDLKKYPYIKRMI
WPFQYNISLKTKDSNVDLINYLPKNKIDSADVSQKLGYNIGGNFQSAPSIGGSGSFNYSKTISYNQKNYV
TEVESQNSKGVKWGVKANSFVTPNGQVSAYDQYLFAQDPTGPAARDYFVPDNQLPPLIQSGFNPSFIT
TLSHERGKGDKSEFEITYGRNMDATYAYVTRHRLAVDRKHDAFKNRNVTVKYEVNWKTHEVKIKSITPK

Fig. 9 (continued)

SEQ ID NO: 13 HlgC nucleotide sequence

GCAAACGACACGGAAGACATCGGCAAAGGTTCAGACATCGAAATCATCAAACGCACGGAAGACAA
AACGAGCAATAAATGGGGTGTGACCCAGAACATTCAATTCGATTTCGTGAAAGACAAAAAATACAAT
AAAGATGCGCTGATTCTGAAAATGCAGGGCTTTATCAGCTCTCGTACCACGTACTACAACTACAAGA
AAACCAACCATGTTAAAGCCATGCGCTGGCCGTTCCAATACAACATCGGTCTGAAAACGAATGACA
AATATGTCAGTCTGATTAACTACCTGCCGAAAAATAAAATCGAATCGACCAACGTGAGCCAGACGCT
GGGCTATAACATTGGCGGTAATTTTCAATCCGCACCGTCACTGGGCGGTAACGGTTCATTCAATTA
CTCAAAATCGATCAGCTATACCCAGCAAAACTACGTGTCTGAAGTTGAACAGCAAAATTCTAAAAGT
GTCCTGTGGGGCGTGAAAGCGAATAGCTTTGCCACGGAATCTGGTCAGAAAAGTGCATTTGATTCC
GACCTGTTCGTGGGCTATAAACCGCATTCAAAAGATCCGCGTGACTACTTCGTGCCGGATTCGGAA
CTGCCGCCGCTGGTTCAGTCAGGTTTTAACCCGTCGTTCATTGCTACCGTTAGTCACGAAAAAGGC
AGTTCCGATACCTCCGAATTTGAAATTACGTATGGTCGTAATATGGACGTCACCCATGCAATCAAAC
GCAGCACGCACTATGGCAACTCTTACCTGGATGGTCATCGTGTTCACAATGCTTTTGTCAACCGCA
ATTATACGGTGAAATACGAAGTCAACTGGAAAACGCACGAAATCAAAGTCAAAGGTCAAAAC

SEQ ID NO: 14 HlgC amino acid sequence

ANDTEDIGKGSDIEIIKRTEDKTSNKWGVTQNIQFDFVKDKKYNKDALILKMQGFISSRTTYYNYKKTNHV
KAMRWPFQYNIGLKTNDKYVSLINYLPKNKIESTNVSQTLGYNIGGNFQSAPSLGGNGSFNYSKSISYTQ
QNYVSEVEQQNSKSVLWGVKANSFATESGQKSAFDSDLFVGYKPHSKDPRDYFVPDSELPPLVQSGF
NPSFIATVSHEKGSSDTSEFEITYGRNMDVTHAIKRSTHYGNSYLDGHRVHNAFVNRNYTVKYEVNWKT
HEIKVKGQN

SEQ ID NO: 15 HlgB nucleotide sequence

GCGGAAGGCAAAATTACCCCGGTCTCGGTGAAAAAAGTTGACGACAAAGTGACGCTGTATAAAACG
ACGGCCACGGCTGATTCGGATAAATTTAAAATTAGCCAGATCCTGACCTTCAACTTCATCAAAGATA
AATCTTACGATAAAGACACCCTGGTGCTGAAAGCAACGGGCAACATCAATAGCGGTTTTGTTAAAC
CGAACCCGAATGATTACGACTTCTCAAAACTGTATTGGGGCGCAAAATACAATGTTTCGATTAGCTC
TCAGAGTAACGATTCCGTCAATGTGGTTGACTATGCTCCGAAAAACCAAAATGAAGAATTTCAGGTG
CAAAACACCCTGGGTTACACGTTCGGCGGTGATATTTCAATCTCGAATGGCCTGAGTGGCGGTCTG
AACGGTAATACCGCGTTTTCCGAAACGATTAACTATAAACAGGAAAGCTACCGTACCACGCTGTCTC
GCAACACCAATTATAAAAATGTCGGCTGGGGTGTGGAAGCCCATAAAATCATGAACAATGGCTGGG
GTCCGTATGGCCGTGACTCCTTTCACCCGACGTACGGCAACGAACTGTTCCTGGCAGGTCGCCAG
AGTTCCGCATATGCAGGTCAAAATTTTATTGCCCAGCATCAAATGCCGCTGCTGAGCCGTTCTAACT
TTAATCCGGAATTCCTGTCAGTCCTGTCGCACCGCCAGGATGGCGCGAAAAAATCTAAAATCACCG
TTACGTACCAGCGTGAAATGGACCTGTACCAAATCCGCTGGAACGGCTTCTATTGGGCAGGTGCTA
ACTACAAAAACTTCAAAACCCGTACGTTCAAATCTACCTATGAAATCGATTGGGAAAACCACAAAGT
CAAACTGCTGGACACGAAAGAAACGGAAAATAATAAA

SEQ ID NO: 16 HlgB amino acid sequence

AEGKITPVSVKKVDDKVTLYKTTATADSDKFKISQILTFNFIKDKSYDKDTLVLKATGNINSGFVKPNPNDY
DFSKLYWGAKYNVSISSQSNDSVNVVDYAPKNQNEEFQVQNTLGYTFGGDISISNGLSGGLNGNTAFS
ETINYKQESYRTTLSRNTNYKNVGWGVEAHKIMNNGWGPYGRDSFHPTYGNELFLAGRQSSAYAGQN
FIAQHQMPLLSRSNFNPEFLSVLSHRQDGAKKSKITVTYQREMDLYQIRWNGFYWAGANYKNFKTRTF
KSTYEIDWENHKVKLLDTKETENNK

Fig. 9 (continued)

SEQ ID NO: 17 LukH USA300 nucleotide sequence

AACTCGGCTCATAAAGATAGTCAGGATCAAAATAAAAAAGAACACGTGGATAAATCACAACAGAAAG
ATAAACGCAATGTCACCAATAAAGATAAAAATAGCACCGCACCGGATGACATTGGCAAAAACGGTA
AAATCACCAAACGTACCGAAACGGTGTATGATGAAAAAACGAATATTCTGCAGAACCTGCAATTTGA
TTTCATCGATGACCCGACCTACGACAAAAATGTGCTGCTGGTTAAAAAACAGGGCAGCATTCATTCT
AACCTGAAATTCGAAAGTCACAAAGAAGAGAAAAACTCCAACTGGCTGAAATATCCGTCAGAATACC
ATGTCGATTTCCAGGTGAAACGTAATCGCAAACCGAAATTCTGGACCAACTGCCGAAAAACAAAAT
CAGTACCGCCAAAGTTGATAGTACGTTTTCCTATAGCTCTGGCGGTAAATTCGACTCTACCAAAGGC
ATCGGTCGTACGAGTTCCAACTCATACTCGAAAACCATCTCGTACAACCAGCAAAACTACGATACGA
TCGCAAGCGGCAAAAACAATAACTGGCATGTTCACTGGTCTGTCATTGCTAACGATCTGAAATATGG
CGGTGAAGTTAAAAATCGCAACGACGAACTGCTGTTTTACCGTAATACCCGCATCGCGACGGTCGA
AAACCCGGAACTGTCATTCGCGTCGAAATATCGTTACCCGGCCCTGGTGCGCTCCGGTTTTAATCC
GGAATTCCTGACCTACCTGAGCAACGAAAAATCTAACGAAAAAACGCAGTTCGAAGTCACCTATAC
GCGTAATCAAGATATTCTGAAAAACCGTCCGGGCATTCACTACGCACCGCCGATCCTGGAGAAAAA
CAAAGATGGTCAGCGCCTGATCGTGACCTATGAAGTTGACTGGAAAAACAAACCGTGAAAGTGGT
GGACAAATACTCGGACGACAATAAACCGTACAAAGAAGG

SEQ ID NO: 18 LukH USA300 amino acid sequence

NSAHKDSQDQNKKEHVDKSQQKDKRNVTNKDKNSTAPDDIGKNGKITKRTETVYDEKTNILQNLQFDFI
DDDPTYDKNVLLVKKQGSIHSNLKFESHKEEKNSNWLKYPSEYHVDFQVKRNRKTEILDQLPKNKISTAKV
DSTFSYSSGGKFDSTKGIGRTSSNSYSKTISYNQQNYDTIASGKNNNWHVHWSVIANDLKYGGEVKNR
NDELLFYRNTRIATVENPELSFASKYRYPALVRSGFNPEFLTYLSNEKSNEKTQFEVTYTRNQDILKNRP
GIHYAPPILEKNKDGQRLIVTYEVDWKNKTVKVVDKYSDDNKPYKE

SEQ ID NO: 19 LukG USA300 nucleotide sequence

AAAATCAACAGCGAAATCAAACAAGTCAGCGAAAAAAATCTGGATGGCGATACGAAAATGTACACG
CGCACGGCAACCACGAGCGATTCGCAGAAAAACATCACCCAGAGCCTGCAATTTAATTTCCTGACC
GAACCGAACTACGATAAAGAAACGGTGTTCATCAAAGCAAAAGGCACCATCGGCTCAGGTCTGCGT
ATTCTGGACCCGAATGGCTACTGGAACTCGACCCTGCGCTGGCCGGGTAGCTATTCTGTGAGTATT
CAGAATGTTGATGACAACAATAACACCAACGTTACGGATTTTGCTCCGAAAAATCAAGATGAAAGCC
GTGAAGTCAAATATACCTACGGCTATAAAACGGGCGGTGATTTCTCTATCAATCGCGGCGGTCTGA
CCGGTAATATTACGAAAGAATCGAACTATAGCGAAACCATCTCCTACCAGCAACCGTCATATCGTAC
CCTGCTGGATCAGTCCACGTCACATAAAGGCGTTGGTTGGAAAGTCGAAGCGCACCTGATCAATAA
CATGGGCCATGATCACACCCGTCAACTGACGAATGATAGCGACAACCGCACGAAATCTGAAATTTT
TAGTCTGACCCGCAATGGTAACCTGTGGGCGAAAGATAACTTCACGCCGAAAGACAAAATGCCGGT
CACCGTGTCCGAAGGCTTTAATCCGGAATTCCTGGCCGTTATGTCTCATGATAAAAAAGACAAAGG
TAAAAGTCAGTTCGTGGTTCACTACAAACGTTCCATGGATGAATTCAAAATCGACTGGAACCGCCAT
GGCTTCTGGGGTTACTGGAGCGGTGAAAACCACGTCGATAAAAAAGAAGAAAAACTGTCTGCACTG
TATGAAGTGGACTGGAAAACCCACAATGTCAAATTCGTGAAAGTTCTGAATGATAATGAAAAAAAA

SEQ ID NO: 20 LukG USA300 amino acid sequence

KINSEIKQVSEKNLDGDTKMYTRTATTSDSQKNITQSLQFNFLTEPNYDKETVFIKAKGTIGSGLRILDPN
GYWNSTLRWPGSYSVSIQNVDDNNNTNVTDFAPKNQDESREVKYTYGYKTGGDFSINRGGLTGNITKE
SNYSETISYQQPSYRTLLDQSTSHKGVGWKVEAHLINNMGHDHTRQLTNDSDNRTKSEIFSLTRNGNL
WAKDNFTPKDKMPVTVSEGFNPEFLAVMSHDKKDKGKSQFVVHYKRSMDEFKIDWNRHGFWGYWSG
ENHVDKKEEKLSALYEVDWKTHNVKFVKVLNDNEKK

Fig. 9 (continued)

SEQ ID NO: 21 LukH MRSA252 nucleotide sequence

GCAAACAAGGACTCCCAGGACCAGACCAAAAAAGAACACGTCGATAAAGCACAGCAGAAAGAAAA
GCGTAATGTCAACGATAAAGATAAAAATACCCCGGGCCCGGATGACATTGGCAAAAACGGCAAGGT
TACCAAACGTACCGTCAGTGAATATGACAAAGAAACCAATATTCTGCAGAACCTGCAATTTGATTTC
ATCGATGACCCGACGTACGACAAAAATGTGCTGCTGGTTAAAAAGCAAGGTAGTATCCATTCCAAC
CTGAAGTTTGAAAGCCACCGTAATGAAACCAACGCGAGTTGGCTGAAATATCCGTCCGAATACCAT
GTCGATTTCCAGGTGCAACGCAATCCGAAAACGGAAATTCTGGACCAGCTGCCGAAAAACAAGATC
TCAACCGCAAAAGTGGATTCGACGTTTAGTTATTCCCTGGGCGGTAAATTCGACAGCACCAAAGGC
ATTGGTCGCACCAGCAGCAACAGCTACTCGAAGAGCATCTCTTACAACCAGCAAAACTACGATACC
ATCGCAAGCGGCAAAAACAATAACCGTCATGTTCACTGGTCTGTGGTTGCTAATGATCTGAAGTATG
GTAACGAAATCAAAAATCGCAACGACGAATTTCTGTTCTACCGTAATACCCGCCTGAGTACGGTCG
AAAACCCGGAACTGTCATTTGCGTCGAAATATCGTTACCCGGCCCTGGTTCGCTCCGGCTTTAATC
CGGAATTTCTGACCTACATCAGCAACGAAAAGTCTAACGAAAAGACGCGTTTCGAAGTGACCTATA
CGCGCAATCAGGATATCCTGAAAAACAAGCCGGGCATTCACTACGGTCAGCCGATCCTGGAACAAA
ACAAAGATGGCCAGCGTTTTATTGTCGTGTATGAAGTGGACTGGAAAAATAAGACCGTTAAGGTTGT
CGAAAAATATTCTGATCAGAACAAGCCGTACAAAGAAGGT

SEQ ID NO: 22 LukH MRSA252 amino acid sequence

ANKDSQDQTKKEHVDKAQQKEKRNVNDKDKNTPGPDDIGKNGKVTKRTVSEYDKETNILQNLQFDFID
DPTYDKNVLLVKKQGSIHSNLKFESHRNETNASWLKYPSEYHVDFQVQRNPKTEILDQLPKNKISTAKV
DSTFSYSLGGKFDSTKGIGRTSSNSYSKSISYNQQNYDTIASGKNNNRHVHWSVVANDLKYGNEIKNRN
DEFLFYRNTRLSTVENPELSFASKYRYPALVRSGFNPEFLTYISNEKSNEKTRFEVTYTRNQDILKNKPGI
HYGQPILEQNKDGQRFIVVYEVDWKNKTVKVVEKYSDQNKPYKEG

SEQ ID NO: 23 LukG MRSA252 nucleotide sequence

GCAAGCTCGTATGCGGAAATCAAAAGCAAGATCACCACCGTCTCAGAAAAGAACCTGGATGGCGA
CACCAAGATGTACACCCGTACCGCGACCACGAGCGATACGGAAAAGAAAATTAGCCAGTCTCTGCA
ATTTAATTTCCTGACCGAACCGAACTACGACAAAGAAACGGTGTTTATTAAAGCCAAGGGCACCATC
GGCAGCGGTCTGAAAATTCTGAATCCGAACGGCTACTGGAACAGCACCCTGCGTTGGCCGGGTAG
TTATTCCGTTTCAATTCAGAACGTCGATGACAACAATAACTCAACCAATGTCACGGATTTTGCACCG
AAAAACCAAGACGAATCGCGTGAAGTGAAATATACCTACGGCTATAAGACGGGCGGTGATTTCAGT
ATCAATCGCGGTGGTCTGACCGGTAACATCACGAAGGAAAAGAACTACTCGGAAACCATCAGCTAC
CAGCAACCGTCTTATCGTACCCTGATTGATCAGCCGACCACGAATAAAGGCGTCGCGTGGAAGGT
GGAAGCCCATAGCATCAATAACATGGGTCATGATCACACCCGTCAACTGACGAACGACTCTGATGA
CCGCGTGAAATCTGAAATTTTTAGTCTGACCCGCAATGGCAACCTGTGGGCAAAAGATAATTTCAC
GCCGAAAAACAAGATGCCGGTGACCGTTTCCGAAGGCTTTAATCCGGAATTTCTGGCTGTTATGTC
CCATGATAAAAACGACAAAGGTAAGTCACGTTTCATCGTCCACTATAAACGCTCGATGGATGACTTT
AAACTGGATTGGAATAAGCATGGCTTCTGGGGTTACTGGAGTGGTGAAAACCACGTTGACCAGAAA
GAAGAAAAGCTGTCCGCCCTGTATGAAGTGGATTGGAAAACGCACGACGTTAAACTGATTAAGACC
ATCAACGATAAAGAACAGAAG

SEQ ID NO: 24 LukG MRSA252 amino acid sequence

ASSYAEIKSKITTVSEKNLDGDTKMYTRTATTSDTEKKISQSLQFNFLTEPNYDKETVFIKAKGTIGSGLKI
LNPNGYWNSTLRWPGSYSVSIQNVDDNNNSTNVTDFAPKNQDESREVKYTYGYKTGGDFSINRGGLT
GNITKEKNYSETISYQQPSYRTLIDQPTTNKGVAWKVEAHSINNMGHDHTRQLTNDSDDRVKSEIFSLTR
NGNLWAKDNFTPKNKMPVTVSEGFNPEFLAVMSHDKNDKGKSRFIVHYKRSMDDFKLDWNKHGFWG
YWSGENHVDQKEEKLSALYEVDWKTHDVKLIKTINDKEQK

Fig. 9 (continued)

SEQ ID NO: 25 LukH MSHR nucleotide sequence

GACTCACAGGACCAAAACAAAAAGGAACACGTTGATAAGGCACAGCAGAAAGACAAGCAAGATAGC
ACCAAGAAAGGCAAAAACGTTGCGGCCCCGGATGACGTCGGCAAAAACGGCAAGGTGACCAAACG
TACGGAAAGCGAATACGATGAAAAGACCAACATCCTGCAGAACCTGGAATTTAATTTCATCGATGAC
CCGACCTACGATAAAGACGTCCTGCTGGTGAAAAAGCAAGGCAGTATTCATTCCAACCTGAAGTTC
GAAAGTCACAAAGAAGAAAAGAACAGCACCTGGCTGAAATATCCGTCAGAATACCATGTTGATTTCC
AGGTCAAGCGTAACCCGAAAACCGAATTCTGGACCAACTGCCGAAAAATAAGATCAGTACGGCAA
AAGTGGATTCAACCTTTTCGTATACGCTGGGCGGTAAATTCGACTCCATTAAAGGCATCGGTCGCA
ATAGCTCTAACAGCTATTCTCAGACCATTTCGTATAATCAGCAAAACTACGATACGATCGCGAGCGG
CAAAAACAATAACTGGCATGTGCACTGGTCTGTTATTGCCAACGATCTGAAGTATGGCGGTGAAGT
TAAAAATCGTAACGACGAATTTCTGTTCTACCGTAACACCCGCACGAGTTCCGTTGATAATCCGGAA
TCATCGTTTGCAGCTAAATATCGTTACCCGGCACTGGTCCGCAGTGGTTTTAATCCGGAATTTCTGA
CCTATCTGAGCAACGAAAAGTCTAATGAAAAAACGCAGTTTGAAGTGACCTATACGCGTAACCAAGA
TATCCTGAAAAATAGCCCGGGCCTGCATTACGCTCCGCCGATTCTGGAAAAGAACAAGGTTGGTCA
CCGCTTTATCGTCACCTATGAAGTGGATTGGAAAAATAAGACGGTGAAGGTGGTTGACAAATACTCT
GATGACCAGCCGTTCCGCGAAGGT

SEQ ID NO: 26 LukH MSHR amino acid sequence

DSQDQNKKEHVDKAQQKDKQDSTKKGKNVAAPDDVGKNGKVTKRTESEYDEKTNILQNLEFNFIDDPT
YDKDVLLVKKQGSIHSNLKFESHKEEKNSTWLKYPSEYHVDFQVKRNPKTEILDQLPKNKISTAKVDSTF
SYTLGGKFDSIKGIGRNSSNSYSQTISYNQQNYDTIASGKNNNWHVHWSVIANDLKYGGEVKNRNDEFL
FYRNTRTSSVDNPESSFAAKYRYPALVRSGFNPEFLTYLSNEKSNEKTQFEVTYTRNQDILKNSPGLHY
APPILEKNKVGHRFIVTYEVDWKNKTVKVVDKYSDDQPFREG

SEQ ID NO: 27 LukG MSHR nucleotide sequence

AAAATCAAATCGGAAATCACGCAAGTTAGCGAACAGAATATCGACGGCAATACGAAGATGTTTACC
CGCACGGCAACGACCTCGGATAGCCAGAAAAAGATCAGCCAGTCTCTGCAATTTAACTTCCTGACC
GAACCGAACTACGACAAGGAAACGGTGTTCATCAAGGCAAAGGGCACCATCGGCTCTGGTCTGAA
AATTCTGGACCCGAACGGCTACTGGAATAGTACCCTGCGTTGGCCGGGTAGTTATTCCGTGTCAAT
CCAGAACGTTGATAACAATACCAATACGAAGGTTACGGATTTTGCCCCGAAAAACCAAGACGAAAC
CCGCGAAGTCAAGTATACCTACGGCTATAAAAACGGGCGGTGATTTCTCGATTAGCCCGGGCGGTAT
TACCGGTAACATCACGAAAGAACGTAATTATTCTGAAACCATCAGTTACCAGCAACCGAGTTATGC
ACCCTGATTGACCAGCCGGCGACGAATAAGGGCGTTGGTTGGAAAGTCGAAGCCCATCTGATCAA
CAATATGGGCCATGATCACACCCGTCAACTGACGAACGATTCCGACAATCGCGTGGGCTCAGAAAT
TTTTACCCTGACGCGTAACGGTAATCTGTGGGCGAAAGATAACTTCACGCCGAAAAATAAGATGCC
GGTCACCGTGTCCGAAGGCTTTAACCCGGAATTTCTGGCCGTTATGTCGCATGATAAAAAGGACAA
AGGCAAGAGCAAATTTGTGGTTCACTATAAACGTACGATGGATGACTTTAAAATCGATTGGATGCGC
CATGGCTTCTGGGGTTACTGGACCGGTAAAAATCACGTTGACCAGAAGGAAGAAAAACTGTCTGCA
CTGTATGAAGTCGATTGGAAAACCCACGACGTGAAGTTCATTAAAGCTCTGGATGACAAAGAAAAG
AAA

SEQ ID NO: 28 LukG MSHR amino acid sequence

KIKSEITQVSEQNIDGNTKMFTRTATTSDSQKKISQSLQFNFLTEPNYDKETVFIKAKGTIGSGLKILDPNG
YWNSTLRWPGSYSVSIQNVDNNTNTKVTDFAPKNQDETREVKYTYGYKTGGDFSISPGGITGNITKERN
YSETISYQQPSYRTLIDQPATNKGVGWKVEAHLINNMGHDHTRQLTNDSDNRVGSEIFTLTRNGNLWAK
DNFTPKNKMPVTVSEGFNPEFLAVMSHDKKDKGKSKFVVHYKRTMDDFKIDWMRHGFWGYWTGKNH
VDQKEEKLSALYEVDWKTHDVKFIKALDDKEKK

CROSS-REACTIVE *STAPHYLOCOCCUS AUREUS* ANTIBODY

BIOLOGIC DEPOSIT UNDER THE BUDAPEST TREATY

This application contains reference to a material or materials deposited under the Budapest Treaty. The deposit was made on Jan. 8, 2013 at DSMZ—Deutsche Samnlung von Mikroorganismen und Zellkulturen GmbH, Inhoffenstr. 7B, D-38124, Braunschweig, Germany under Accession Nos. DSMZ 26747 and DSMZ 26748. All restrictions imposed by the depositor on the availability to the public of the deposited material will be irrevocably removed upon the granting of the patent, with the possible exception of requiring the request for the deposit to be in the format specified in 37 C.F.R. 1.808(b).

BACKGROUND OF THE INVENTION

*Staphylococcus aureus*, an important human pathogen, expresses a multitude of secreted toxins (exotoxins) that can kill several different cell types, including erythrocytes, neutrophil granulocytes and other immune cells, as well as epithelial cells of the lung or skin. Moreover, most of these toxins activate immune cells and act as potent pro-inflammatory signals.

A prominent member of *S. aureus* cytotoxins is alpha hemolysin (Ha), which exerts cytolytic function on human lung epithelial and endothelial cells, lymphocytes and macrophages. It is also able to lyse rabbit red blood cells (RBCs) but much less toxic to human RBCs. Hla is considered to be the key virulence factor in *S. aureus* pneumonia pathogenesis and responsible for tissue damage via lysis of pulmonary epithelial cells and recruiting immune cells in mass quantity. The recruited phagocytic cells, mainly neutrophil granulocytes become targets for other cytotoxins produced by *S. aureus* during disease. The most potent toxins are the bi-component cytolysins, or leukocidins, formed by one S (slow eluted), and one F (fast eluted) component. The gamma hemolysin (Hlg) gene products—universally expressed by all *S. aureus* strains—can form two toxins: HlgAB and HlgCB (subunit B is the F-component), both are highly potent in killing human immune cells: PMNs, lymphocytes and macrophages. The former one is also a very potent hemolysin for human RBCs.

The Panton-Valentine Leukocidin (PVL), also called LukSF is the best characterized of the bi-component toxins. It is carried by phage derived genetic elements, and produced by approximately 5-10% of *S. aureus* strains isolated from patients, however, the rate of PVL-expressing strains is reported to be 50-93% in skin and soft tissue infections, depending on the type of disease (Lina, *Clin Infect Dis,* 1999:1128). LukED (LukD is the F-component) is a less potent leukocidin, but confirmed to be present in the majority of clinical *S. aureus* isolates (Shukla, *J Clin Microbiol,* 2010:3582). Initially, its role was implicated in skin infections only, but being the least characterized among the bi-component toxins, its contribution to other types of *S. aureus* infections can not be excluded. LukED has recently been reported to be involved in bloodstream infection in a murine model of *S. aureus* infection (Alonzo, *Mol Microbiol,* 2012:423). These two gene pairs share significant homology with each other (68-82% amino acid identity), while the recently identified leukocidin LukGH (LukG is the F-component) has a lower homology, with 33-40% identity (Ventura, *PloS ONE,* 2010:e11634; DuMont, *Mol Microbiol,* 2011:814).

The crystal structure of Hla, LukS, LukF, HlgA and HlgB have been determined, and revealed some structural homology, in spite of the low level of amino acid homology between Hla and the bi-component toxin subunits with 16-28% amino acid identity (Galdiero, *Protein Sci,* 2004: 1503; Pedelacq, *Structure,* 1999:277; Menestrina, *FEBS Letters,* 2003:54). All these toxins form a ring-like structure formed by oligomerized subunits, leading to pore formation within the cell membrane and subsequent cytolysis. In case of Hla, the pore has been shown to be heptameric, but for the bi-component toxins, hexameric (Comai, *Mol Microbiol,* 2002:1251), heptameric and octameric (Yamashita, *PNAS,* 2011:17314) heterooligomers have been reported, leading to a debate within the scientific community (reviewed in detail by Kaneko, *Biosci Biotechnol Biochem,* 2004:981)

The different F- and S-components of this toxin family can form not only cognate pairs (these are: LukS-LukF, LukE-LukD, HlgC-HlgB, HlgA-HlgB and LukH-LukG), but also non-cognate pairs, many of those pairs reported by Gravet et al. (Gravet, *FEBS Letters,* 1998:202) and by Dalla Serra et al. for gamma hemolysins and LukS (Dalla Serra, *J Chem Inf Model,* 2005:1539) Due to the redundancy and promiscuous nature of this toxin family, inactivating one single component is unlikely to be effective to fight *S. aureus* infections. This notion is supported by observations reported in the literature when neutralization of a single bi-component toxin only partially affected the phenotype (e.g. Ventura, *PloS ONE,* 2010:e11634; Malachowa, *PloS ONE,* 2011:e18617). Animal studies showed a differential impact of the various bi-component toxins on the survival, depending on the model employed or the species used for in vivo experiments. The most prominent reduction in disease severity was observed when multiple toxins were deleted, e.g. as in a rabbit model of infection using a knock-out strain of *S. aureus* where the agr quorum sensing system, a global regulator of toxin expression was inactivated (Kobayashi, *J Infect Dis,* 2011:204). Therefore, it is expected that antibody cocktails neutralizing more toxins offer a significant advantage over mAbs against single toxins. However, monoclonal antibody (mAb) cocktails comprising of more than three components are challenging to be developed.

The likelihood of finding single antibodies that cross-react between alpha hemolysin and any of the bi-component toxins was considered to be low, based on the low (<30%) sequence homology between Hla and bi-component toxins. The chance of finding single antibodies cross-reactive among S- and F-components is expected to be higher, due to the higher level of sequence homology, with the exception of LukGH. It has been described that hyperimmune serum from animals immunized with LukS can recognize HlgC, however, this is due to the presence of different specificities in the polyclonal serum. Laventie et al. (Laventie, *PNAS,* 2011:16404) described a bi-specific neutralizing antibody against LukS and HlgC. This type of antibody however cannot form avid interaction due to the single binding sites on the cognate antigen. The cross-reactivity of such bi-specific mAbs is normally limited to two specificities, i.e. it does not offer the potential of broad cross-neutralization. In summary, no cross-reactive mAbs against different bi-component *S. aureus* toxins or against alpha hemolysin and any of the bi-component toxins have been reported to date.

SUMMARY OF THE INVENTION

It is the objective of the present invention to provide for an antibody directed against the different *S. aureus* cytotoxins with improved cross-reactive and cross-neutralizing potency.

The object is solved by the subject of the present invention.

According to the invention there is provided a cross-neutralizing antibody comprising at least one polyspecific binding site that binds to alpha-toxin (Ha) and at least one of the bi-component toxins of *Staphylococcus aureus*.

Specifically the bi-component toxin is selected from the group consisting of cognate and non-cognate pairs of F and S components of gamma-hemolysins (HlgABC), PVL (LukSF) and PVL-like toxins, preferably any of HlgAB, HlgCB, LukSF, LukED, LukGH, LukS-HlgB, LukSD, HlgA-LukD, HlgA-LukF, LukG-HlgA, LukEF, LukE-HlgB, HlgC-LukD or HlgC-LukF.

Preferably the binding site binds to at least two or at least three bi-component toxins, preferably at least two or three of any of HlgAB, HlgCB, LukSF and LukED, preferably all of HlgAB, HlgCB, LukSF and LukED.

According to a specific embodiment, the binding site is a CDR binding site, preferably comprising the CDR sequences of a VH and/or a VL binding site.

Specifically, the antibody is a full-length monoclonal antibody or an antibody fragment thereof comprising at least one antibody domain incorporating the binding site, preferably an antibody selected from the group consisting of murine, chimeric, humanized or human antibodies, heavy-chain antibodies, Fab, Fd, scFv and single-domain antibodies like VH, VHH or VL, preferably a human IgG1 antibody.

The antibody preferably has an affinity to bind each of the toxins with a Kd of less than $10^{-8}$M, preferably less than $10^{-9}$M.

According to a specific aspect, the antibody exhibits in vitro neutralization potency in a cell-based assay with an 1050 of less than 50:1 mAb:toxin ratio (mol/mol), preferably less than 10:1, more preferably less than 1:1.

According to a further specific aspect, the antibody neutralizes the targeted toxins in animals, including both, human and non-human animals, and inhibits *S. aureus* pathogenesis in vivo, preferably any models of pneumonia, bacteremia or sepsis, peritonitis and osteomyelitis.

According to a specific embodiment, the antibody binds the same epitope as an antibody designated #AB-24.

According to a further specific embodiment, the antibody comprises the same binding site as an antibody designated #AB-24.

According to a further specific embodiment, the antibody binds the same epitope as an antibody designated #AB-24.

Specifically, the antibody is or is derived from an antibody produced by a host cell deposited under DSM 26747 and/or DSM 26748, or a functionally active variant thereof.

Specifically, the antibody comprises
  (a) an antibody light chain produced by a host cell deposited under DSM 26748; and/or
  (b) an antibody heavy chain produced by a host cell deposited under DSM DSM 26747;
  (c) or a functionally active variant of (a) and/or (b).

According to a further aspect, the invention provides for a plasmid comprising a nucleotide sequence
  encoding an antibody light chain designated #AB-24-LC comprised in a host cell deposited under DSM 26748; and/or
  encoding an antibody heavy chain designated #AB-24-HC comprised in a host cell deposited under DSM 26747.

According to a further aspect, the invention provides for an expression cassette comprising a coding sequence to express an antibody according to the invention, which expression cassette or coding sequence is derived from the plasmid of the invention.

According to a further aspect, the invention provides for a method of producing an antibody of the invention, wherein a host cell is transformed with the plasmid of the invention or the expression cassette of the invention.

Specifically preferred is a host cell and a production method employing such host cell, which host cell comprises
  the plasmid or expression cassette of the invention, which incorporates a coding sequence to express the antibody light chain; and
  the plasmid or expression cassette of the invention, which incorporates a coding sequence to express the antibody heavy chain.

According to a further aspect, the invention provides for a host cell comprising the plasmid of the invention or the expression cassette of the invention.

Specifically the invention refers to a host cell, which is deposited under DSM 26747 or DSM 26748. Such host cell is an *E. coli* host cell transformed with a plasmid of the invention. Specifically, the host cell deposited under DSM 26748 is transformed with the plasmid comprising a nucleotide sequence encoding the antibody light chain designated #AB-24-LC; and the host cell deposited under DSM 26747 is transformed with the plasmid comprising a nucleotide sequence encoding the antibody heavy chain designated #AB-24-HC.

According to a further aspect, the invention provides for a method of producing an antibody of the invention, wherein a host cell of the invention is cultivated or maintained under conditions to produce said antibody.

According to a further aspect, the invention provides for a method of identifying a candidate protective antibody comprising:
  (a) providing a sample containing an antibody or antibody-producing cell; and
  (b) assessing for binding of an antibody in or produced by the sample with an epitope recognized by the antibody designated #AB-24, wherein a positive reaction between the antibody and the epitope identifies the antibody as candidate protective antibody.

According to a further aspect, the invention provides for a method of identifying a candidate protective antibody comprising:
  (a) providing a sample containing an antibody or antibody-producing cell; and
  (b) assessing for binding of an antibody in or produced by the sample with alpha-toxin and at least one of a bi-component toxin of *Staphylococcus aureus*, wherein a positive reaction between the antibody and the toxins identifies the antibody as candidate protective antibody.

According to a further aspect, the invention provides for a method of producing an antibody of the invention, comprising
  (a) providing a candidate protective antibody identified according to the identification method of the invention; and
  (b) producing a monoclonal antibody, or a humanized or human form of the candidate protective antibody, or a derivative thereof with the same epitope binding specificity as the candidate protective antibody.

According to a further aspect, the invention provides for a method of producing an antibody of the invention, comprising (a) immunizing a non-human animal with an epitope recognized by the antibody designated #AB-24;

(b) forming immortalized cell lines from the isolated B-cells;

(c) screening the cell lines obtained in b) to identify a cell line producing a monoclonal antibody that binds to the epitope; and (d) producing the monoclonal antibody, or a humanized or human form of the antibody, or a derivative thereof with the same epitope binding specificity as the monoclonal antibody.

According to a further aspect, the invention provides for a method of producing an antibody of the invention, comprising (a) immunizing a non-human animal with alpha-toxin and at least one of a bi-component toxin of *Staphylococcus aureus* and isolating B-cells producing antibodies;

(b) forming immortalized cell lines from the isolated B-cells;

(c) screening the cell lines to identify a cell line producing a monoclonal antibody that binds to alpha-toxin and at least one of a bi-component toxin of *Staphylococcus aureus*; and (d) producing the monoclonal antibody, or a humanized or human form of the antibody, or a derivative thereof with the same epitope binding specificity as the monoclonal antibody.

According to a further aspect, the invention provides for an antibody of the invention for medical use, including human medical and veterinary use. Specifically the antibody is provided for use in treating a subject at risk of or suffering from a *S. aureus* infection comprising administering to the subject an effective amount of the antibody to limit the infection in the subject, to ameliorate a disease condition resulting from said infection or to inhibit *S. aureus* pneumonia pathogenesis.

Specifically the antibody is provided for protecting against *S. aureus* infections.

According to a specific aspect, there is further provided a method of treatment wherein a subject at risk of or suffering from a *S. aureus* infection is treated, which method comprises administering to the subject an effective amount of the antibody to limit the infection in the subject, to ameliorate a disease condition resulting from said infection or to inhibit *S. aureus* pneumonia pathogenesis.

Specifically, the method of treatment is provided for protecting against pathogenic *S. aureus*.

According to a specific embodiment, the antibody is administered in a parenteral or mucosal formulation.

According to a further aspect, the invention provides for a pharmaceutical preparation of an antibody of the invention, preferably comprising a parenteral or mucosal formulation, optionally containing a pharmaceutically acceptable carrier or excipient.

According to a further aspect, the invention provides for an antibody of the invention, for diagnostic use to detect any *S. aureus* infections, including high toxin producing MRSA infections, such as necrotizing pneumonia, and toxin production in furunculosis and carbunculosis.

Specifically, the antibody is provided for use according to the invention, wherein a systemic infection with *S. aureus* in a subject is determined ex vivo by contacting a sample of body fluid of said subject with the antibody, wherein a specific immune reaction of the antibody determines the infection.

According to a specific aspect, there is further provided a method of diagnosing an *S. aureus* infection in a subject, including high toxin producing MRSA infections, such as necrotizing pneumonia, and toxin production in furunculosis and carbunculosis.

Specifically, the method of diagnosing is provided, wherein a systemic infection with *S. aureus* in a subject is determined ex vivo by contacting a sample of body fluid of said subject with the antibody, wherein a specific immune reaction of the antibody determines the infection.

According to a further aspect, the invention provides for a diagnostic preparation of an antibody of the invention, optionally containing the antibody with a label and/or a further diagnostic reagent with a label.

According to a further aspect, the invention provides for an isolated conformational epitope recognized by an antibody designated #AB-24. Such epitope may consist of a single epitope or a mixture of epitopes comprising epitope variants, each recognized by the antibody designated #AB-24.

According to a further aspect, the invention provides for an immunogen comprising:

(a) an epitope of the invention;

(b) optionally further epitopes not natively associated with said epitope of (a); and (c) a carrier.

Specifically, the carrier is a pharmaceutically acceptable carrier, preferably comprising buffer and/or adjuvant substances.

The immunogen of the invention is preferably provided in a vaccine formulation, preferably for parenteral use.

Specifically the immunogen of the invention is provided for medical use, specifically for use in treating a subject by administering an effective amount of said immunogen to protect the subject from an *S. aureus* infection, to prevent a disease condition resulting from said infection or to inhibit *S. aureus* pneumonia pathogenesis.

Specifically the immunogen of the invention is provided for eliciting a protective immune response.

According to a specific aspect, there is further provided a method of treatment wherein a subject at risk of a *S. aureus* infection is treated, which method comprises administering to the subject an effective amount of the immunogen to prevent infection in the subject, in particular to protect against pathogenic *S. aureus*.

According to a further aspect, the invention provides for an isolated nucleic acid encoding an antibody of the invention, or encoding an epitope of the invention.

FIGURES

Figure 1:
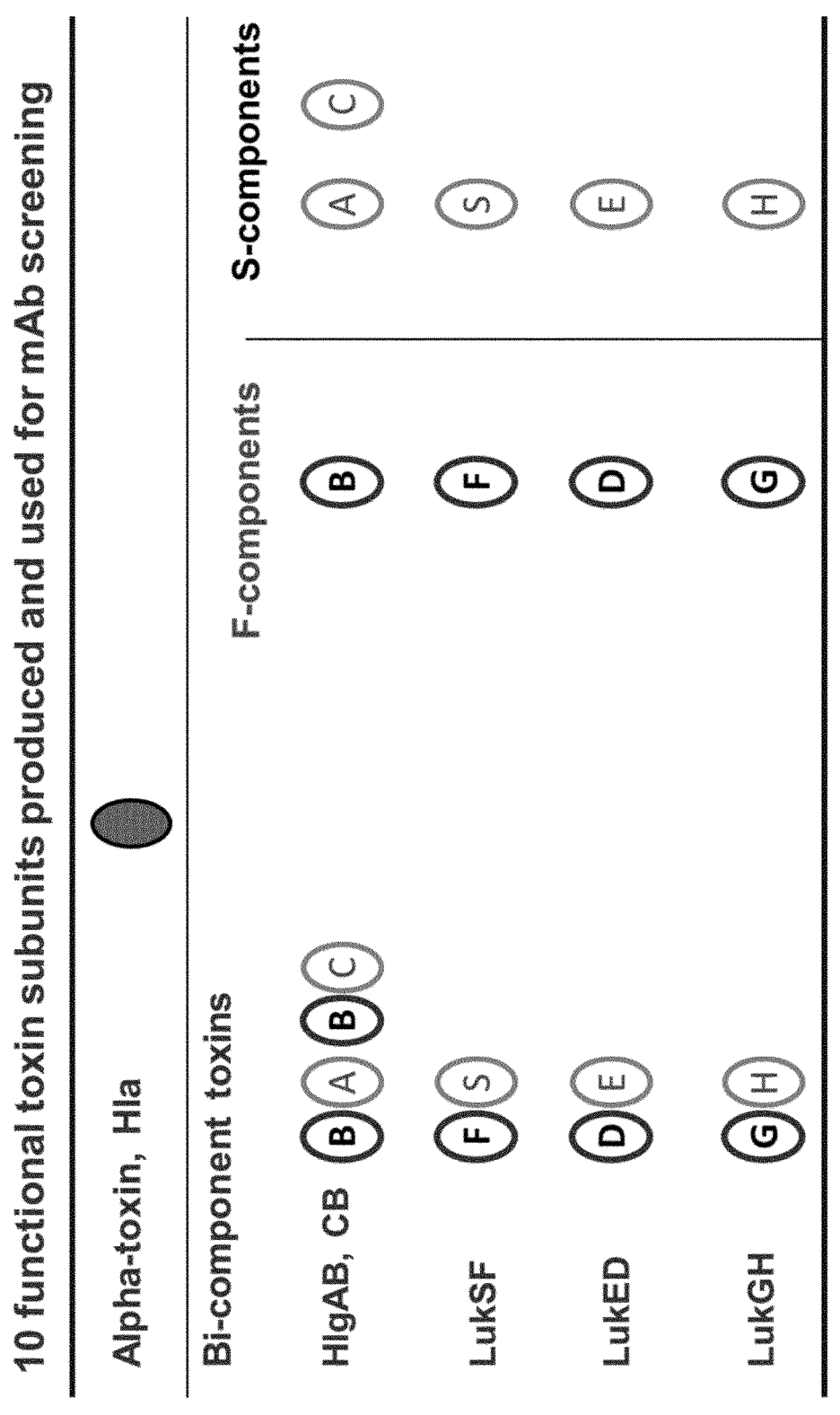

FIG. 1: Schematic figure representing toxin components produced in recombinant forms for mAb screening.

FIG. 2: Determining the Hla neutralization potency of monoclonal antibodies in vitro, as described in Example 3.

A: using rabbit red blood cells B: using human lung epithelial cells (A549 cell line (from ATCC)

Figure 3:
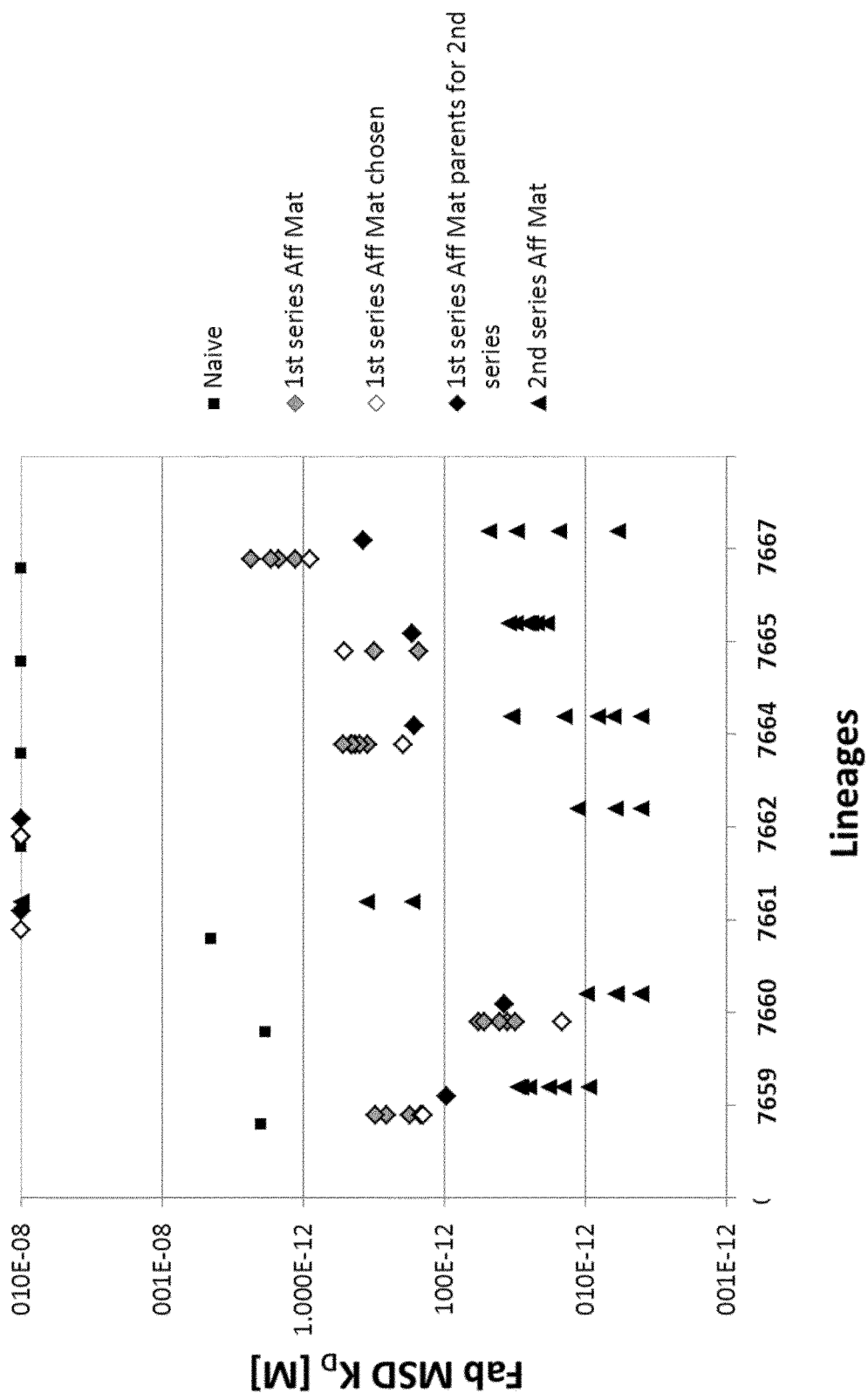

FIG. 3: Affinity (Kd) of naïve and affinity matured Hla specific mAbs with neutralizing potency, as described in Example 3.

Figure 4:
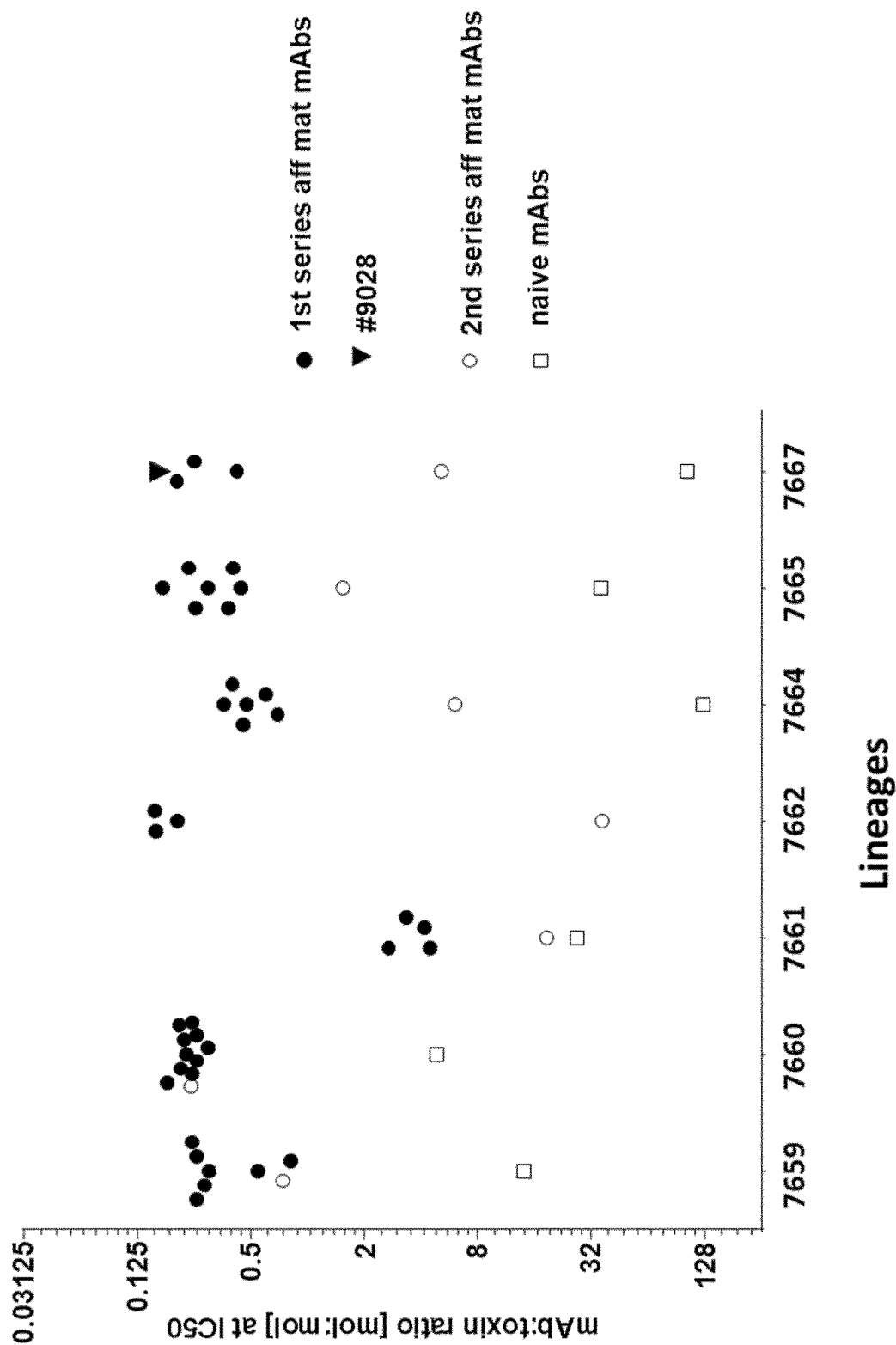

FIG. 4: In vitro neutralization potency of affinity matured Hla mAbs, including the cross-neutralizing Hla mAb #AB-24 (named #9028) as described in Example 3.

Figure 5:
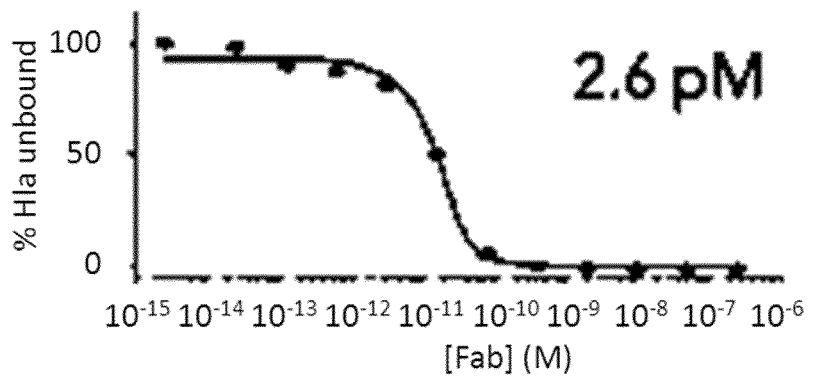
Figure 5:
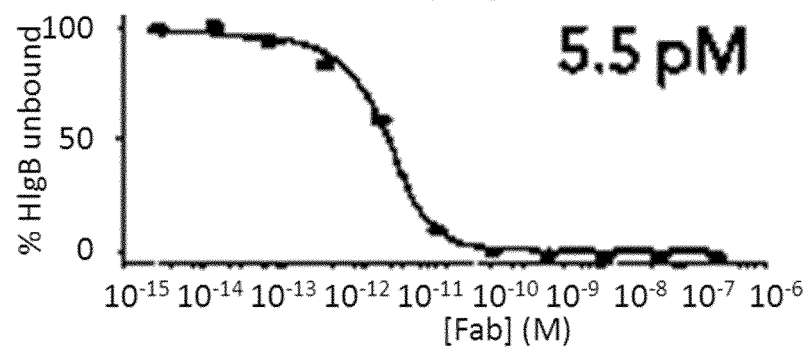
Figure 5:
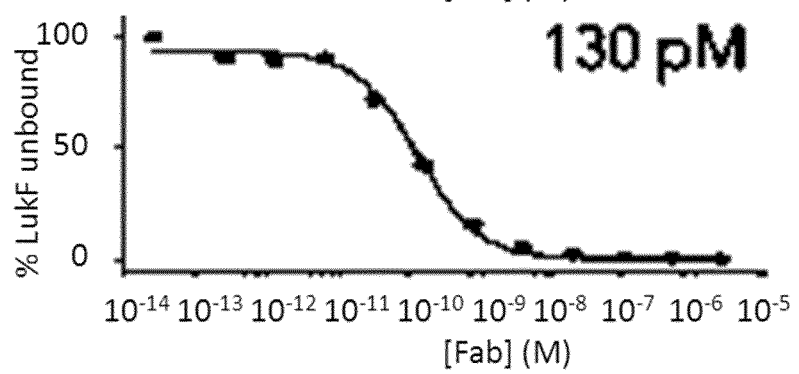
Figure 5:
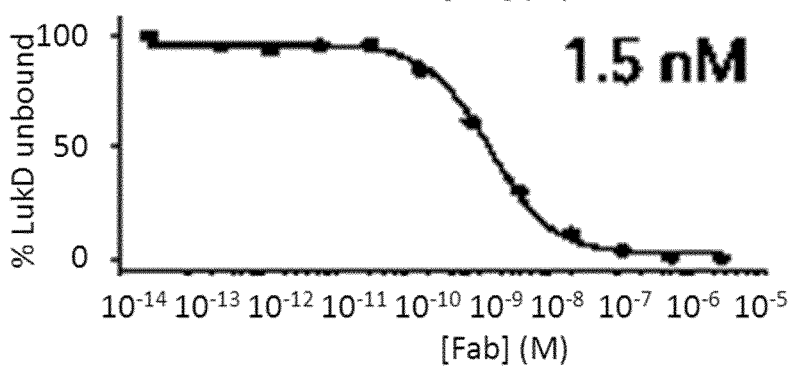

FIG. 5: Affinity (Kd) of broadly cross-neutralizing Hla mAb #AB-24 (named #9028) to F-components of leukocidins, as described in Example 3.

Figure 6:
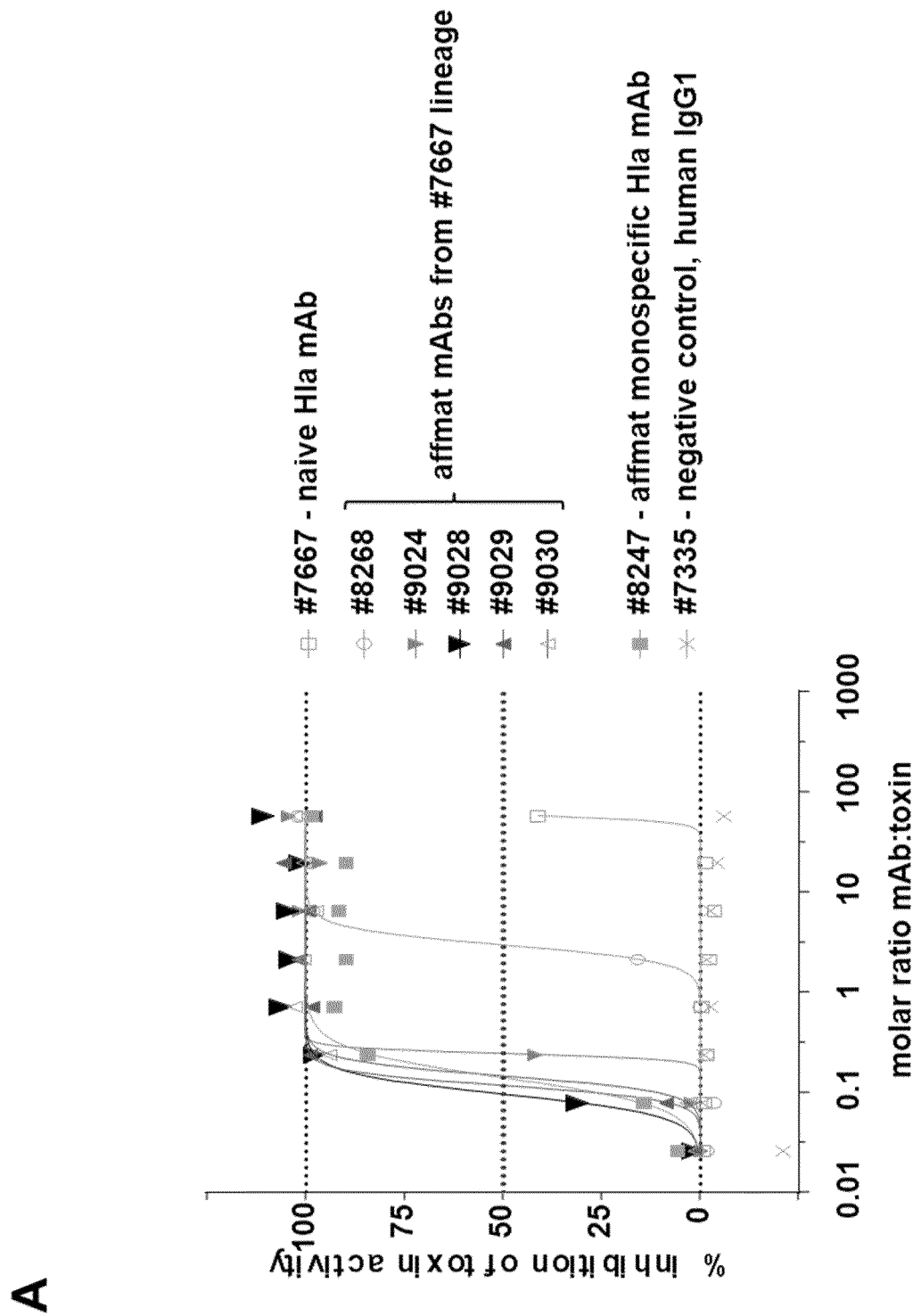
Figure 6:
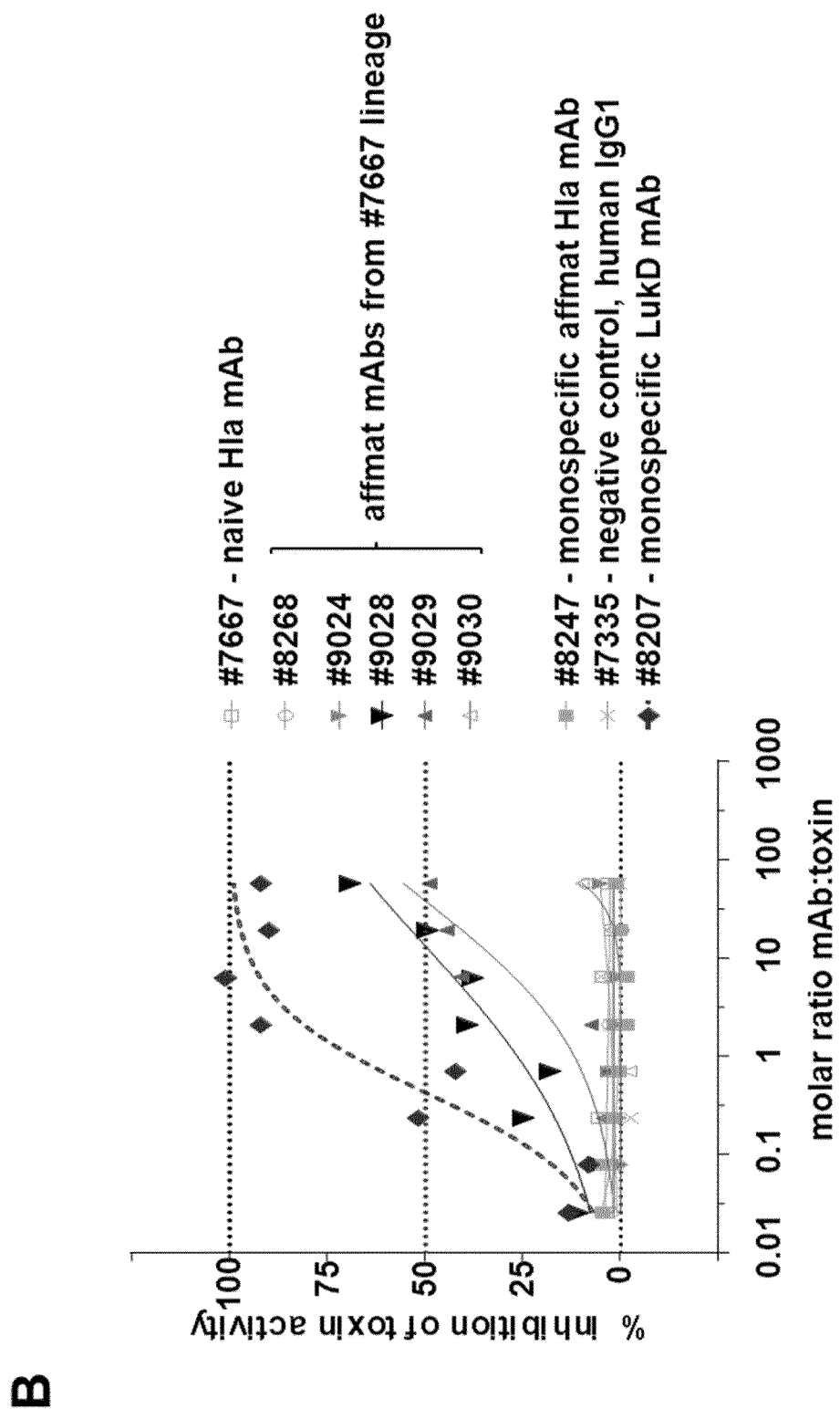
Figure 6:
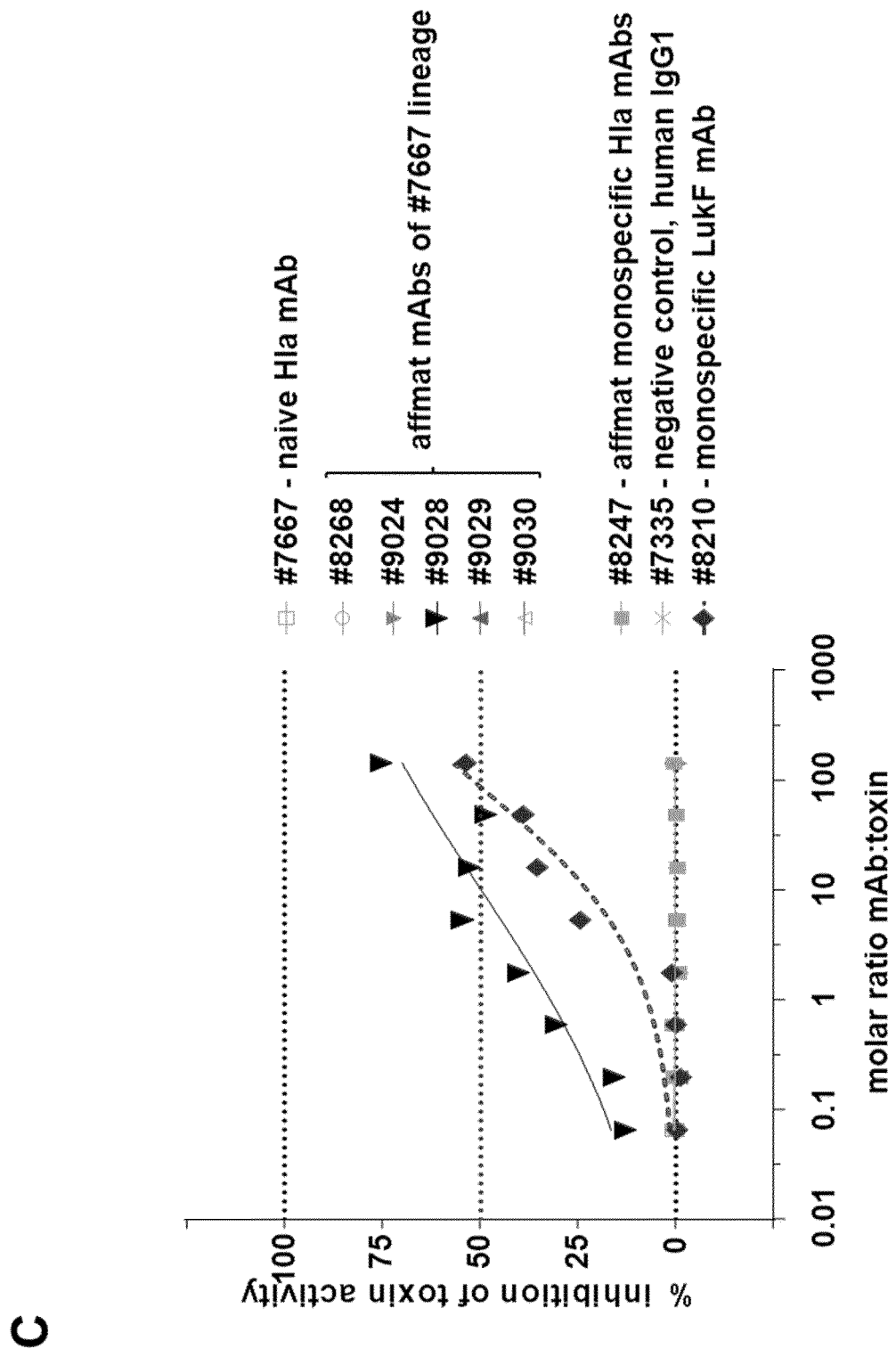

FIG. 6: In vitro neutralization potency of #7667 lineage. Alpha hemolysin neutralization assay on A549 cells (A), neutralization of LukS-LukF (B), HlgC-HlgB (C) and LukE-LukD. Note: #AB-24 is herein named #9028.

Figure 7:
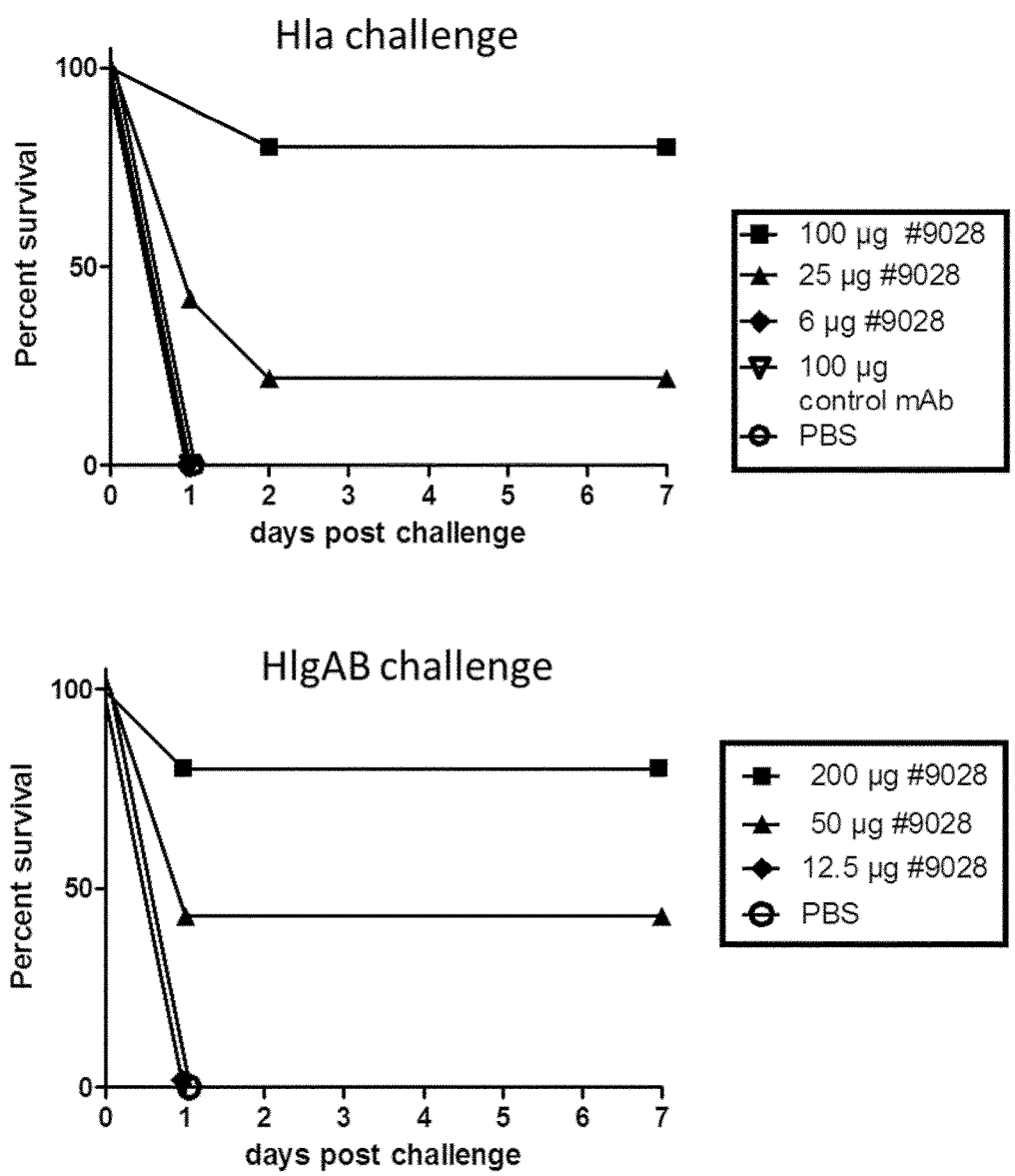

FIG. 7: Protection of mice from lethal toxin challenge by treatment with monoclonal antibodies, as described in Example 5. Note: #AB-24 is herein named #9028. (Top panel) intranasal Hla challenge, (bottom panel) intravaneus HlgAB challenge.

Figure 8:
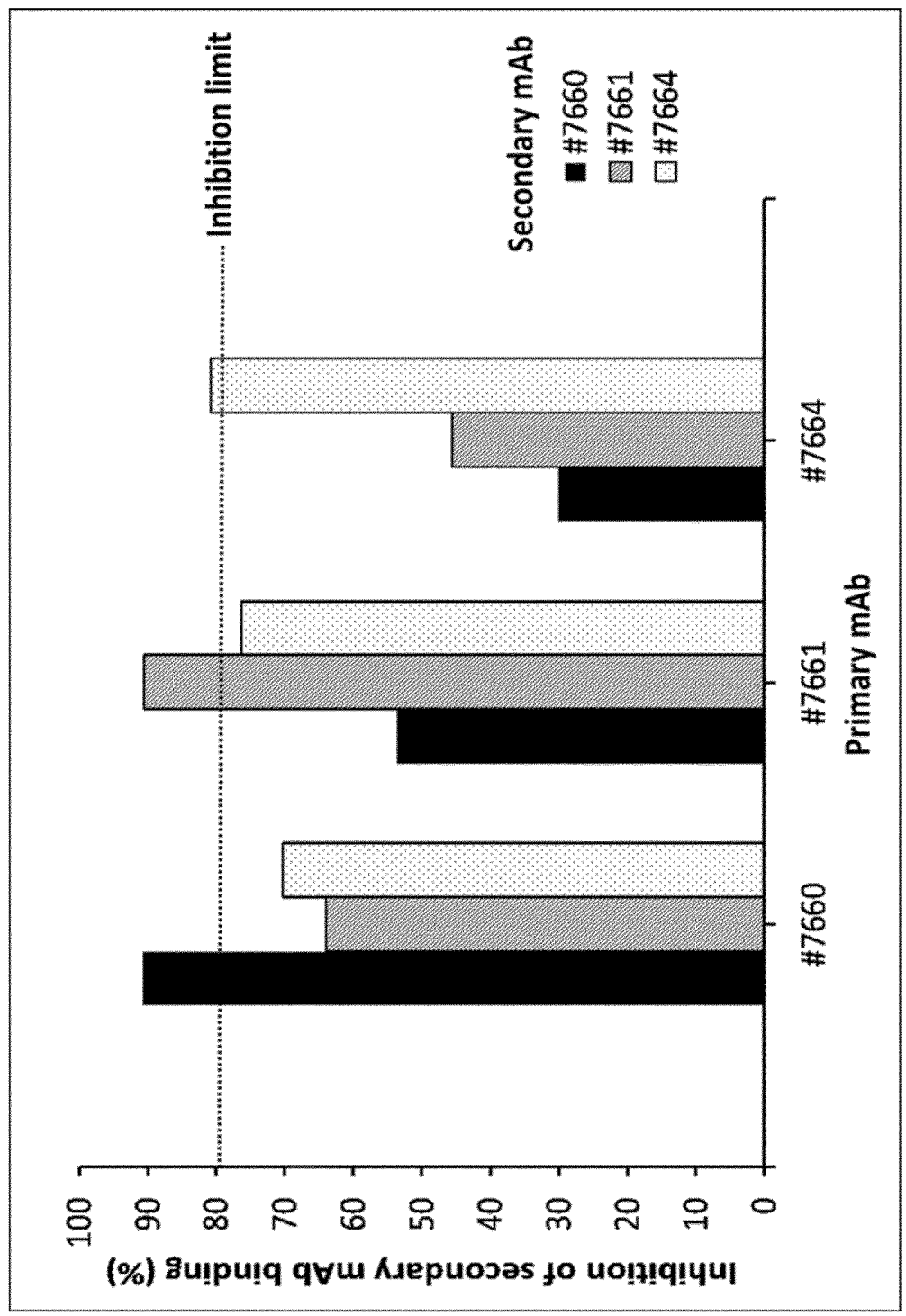

FIG. 8: Competition between Hla mAbs determined in Forte-Bio, as described in Example 6.

FIG. 9: S. aureus toxin sequences obtained as described in Example 1.

SEQ ID 1 Hla nucleotide sequence of the USA300 TCH1516 strain (Genbank, accession number CP000730)

SEQ ID 2: Hla amino acid sequence of the USA300 TCH1516 strain

SEQ ID 3 LukS nucleotide sequence of the USA300 TCH1516 strain

SEQ ID 4: LukS amino acid sequence of the USA300 TCH1516 strain

SEQ ID 5 LukF nucleotide sequence of the USA300 TCH1516 strain

SEQ ID 6: LukF amino acid sequence of the USA300 TCH1516 strain

SEQ ID 7 LukE nucleotide sequence of the USA300 TCH1516 strain

SEQ ID 8: LukE amino acid sequence of the USA300 TCH1516 strain

SEQ ID 9 LukD nucleotide sequence of the USA300 TCH1516 strain

SEQ ID 10: LukD amino acid sequence of the USA300 TCH1516 strain

SEQ ID 11 HlgA nucleotide sequence of the USA300 TCH1516 strain

SEQ ID 12: HlgA amino acid sequence of the USA300 TCH1516 strain

SEQ ID 13 HlgC nucleotide sequence of the USA300 TCH1516 strain

SEQ ID 14: HlgC amino acid sequence of the USA300 TCH1516 strain

SEQ ID 15 HlgB nucleotide sequence of the USA300 TCH1516 strain

SEQ ID 16: HlgB amino acid sequence of the USA300 TCH1516 strain

SEQ ID 17: LukH nucleotide sequence of the USA300 TCH1516 strain

SEQ ID 18: LukH amino acid sequence of the USA300 TCH1516 strain

SEQ ID 19 LukG nucleotide sequence of the USA300 TCH1516 strain

SEQ ID 20: LukG amino acid sequence of the USA300 TCH1516 strain

SEQ ID 21 LukH nucleotide sequence of the MRSA252 strain (Genbank, accession number BX571856)

SEQ ID 22: LukH amino acid sequence of the MRSA252 strain

SEQ ID 23 LukG nucleotide sequence of the MRSA252 strain

SEQ ID 24: LukG amino acid sequence of the MRSA252 strain

SEQ ID 25 LukH nucleotide sequence of the MSHR1132 strain (Genbank, accession number FR821777)

SEQ ID 26: LukH amino acid sequence of the MSHR1132 strain

SEQ ID 27 LukG nucleotide sequence of the MSHR1132 strain

SEQ ID 28: LukG amino acid sequence of the MSHR1132 strain

DETAILED DESCRIPTION

The term "antibody" as used herein shall refer to polypeptides or proteins that consist of or comprise antibody domains, which are understood as constant and/or variable domains of the heavy and/or light chains of immunoglobulins, with or without a linker sequence. Polypeptides are understood as antibody domains, if comprising a beta-barrel structure consisting of at least two beta-strands of an antibody domain structure connected by a loop sequence. Antibody domains may be of native structure or modified by mutagenesis or derivatization, e.g. to modify the antigen binding properties or any other property, such as stability or functional properties, such as binding to the Fc receptors FcRn and/or Fcgamma receptor.

The antibody as used herein has a specific binding site to bind one or more antigens or one or more epitopes of such antigens, specifically comprising a CDR binding site of a single variable antibody domain, such as VH, VL or VHH, or a binding site of pairs of variable antibody domains, such as a VL/VH pair, an antibody comprising a VL/VH domain pair and constant antibody domains, such as Fab, F(ab'), (Fab)₂, scFv, Fv, or a full length antibody.

The term "antibody" as used herein shall particularly refer to antibody formats comprising or consisting of single variable antibody domain, such as VH, VL or VHH, or combinations of variable and/or constant antibody domains with or without a linking sequence or hinge region, including pairs of variable antibody domains, such as a VL/VH pair, an antibody comprising or consisting of a VL/VH domain pair and constant antibody domains, such as heavy-chain antibodies, Fab, F(ab'), (Fab)₂, scFv, Fd, Fv, or a full-length antibody, e.g. of an IgG type (e.g., an IgG1, IgG2, IgG3, or IgG4 sub-type), IgA1, IgA2, IgD, IgE, or IgM antibody. The term "full length antibody" can be used to refer to any antibody molecule comprising at least most of the Fc domain and other domains commonly found in a naturally occurring antibody monomer. This phrase is used herein to emphasize that a particular antibody molecule is not an antibody fragment.

The term "antibody" shall specifically include antibodies in the isolated form, which are substantially free of other antibodies directed against different target antigens or comprising a different structural arrangement of antibody domains. Still, an isolated antibody may be comprised in a combination preparation, containing a combination of the isolated antibody, e.g. with at least one other antibody, such as monoclonal antibodies or antibody fragments having different specificities.

The term "antibody" shall apply to antibodies of animal origin, including human species, such as mammalian, including human, murine, rabbit, goat, lama, cow and horse, or avian, such as hen.

The term "antibody" further applies to chimeric antibodies with sequences of origin of different species, such as sequences of murine and human origin.

The term "chimeric" as used with respect to an antibody refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations.

The term "antibody" further applies to humanized antibodies.

The term "humanized" as used with respect to an antibody refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen-binding sites may be wild-type or modified, e.g. by one or more amino acid substitutions, preferably modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "antibody" further applies to human antibodies.

The term "human" as used with respect to an antibody, is understood to include antibodies having variable and constant regions derived from human germline immunoglobulin sequences. The human antibody of the invention may include amino acid residues not encoded by human germline immunoglobulin sequences (e.g., mutations introduced by random or site-specific mutagenesis in vitro or by somatic mutation in vivo), for example in the CDRs. Human antibodies include antibodies isolated from human immunoglobulin libraries or from animals transgenic for one or more human immunoglobulin.

The term specifically applies to antibodies of any class or subclass. Depending on the amino acid sequence of the constant domain of their heavy chains, antibodies can be assigned to the major classes of antibodies IgA, IgD, IgE, IgG, and IgM, and several of these may be further divided into subclasses (isotypes), e.g., IgG1, IgG2, IgG3, IgG4, IgA, and IgA2.

The term further applies to monoclonal or polyclonal antibodies, specifically a recombinant antibody, which term includes all antibodies and antibody structures that are prepared, expressed, created or isolated by recombinant means, such as antibodies originating from animals, e.g. mammalians including human, that comprises genes or sequences from different origin, e.g. chimeric, humanized antibodies, or hybridoma derived antibodies. Further examples refer to antibodies isolated from a host cell transformed to express the antibody, or antibodies isolated from a recombinant, combinatorial library of antibodies or antibody domains, or antibodies prepared, expressed, created or isolated by any other means that involve splicing of antibody gene sequences to other DNA sequences.

It is understood that the term "antibody" also refers to derivatives of an antibody, in particular functionally active derivatives. An antibody derivative is understood as any combination of one or more antibody domains or antibodies and/or a fusion protein, in which any domain of the antibody may be fused at any position of one or more other proteins, such as other antibodies, e.g. a binding structure comprising CDR loops, a receptor polypeptide, but also ligands, scaffold proteins, enzymes, toxins and the like. A derivative of the antibody may be obtained by association or binding to other substances by various chemical techniques such as covalent coupling, electrostatic interaction, di-sulphide bonding etc. The other substances bound to the antibody may be lipids, carbohydrates, nucleic acids, organic and inorganic molecules or any combination thereof (e.g. PEG, prodrugs or drugs). In a specific embodiment, the antibody is a derivative comprising an additional tag allowing specific interaction with a biologically acceptable compound. There is not a specific limitation with respect to the tag usable in the present invention, as far as it has no or tolerable negative impact on the binding of the antibody to its target. Examples of suitable tags include His-tag, Myc-tag, FLAG-tag, Strep-tag, Calmodulin-tag, GST-tag, MBP-tag, and S-tag. In another specific embodiment, the antibody is a derivative comprising a label. The term "label" as used herein refers to a detectable compound or composition which is conjugated directly or indirectly to the antibody so as to generate a "labeled" antibody. The label may be detectable by itself, e.g. radioisotope labels or fluorescent labels, or, in the case of an enzymatic label, may catalyze chemical alteration of a substrate compound or composition which is detectable.

The preferred derivatives as described herein are functionally active with regard to the antigen binding, preferably which have a potency to neutralize S. aureus and/or which are protective antibodies.

It is understood that the term "antibody" also refers to variants of an antibody.

The term "variant" shall particularly refer to antibodies, such as mutant antibodies or fragments of antibodies, e.g. obtained by mutagenesis methods, in particular to delete, exchange, introduce inserts into a specific antibody amino acid sequence or region or chemically derivatize an amino acid sequence, e.g. in the constant domains to engineer the antibody stability, effector function or half-life, or in the variable domains to improve antigen-binding properties, e.g. by affinity maturation techniques available in the art. Any of the known mutagenesis methods may be employed, including point mutations at desired positions, e.g. obtained by randomisation techniques. In some cases positions are chosen randomly, e.g. with either any of the possible amino acids or a selection of preferred amino acids to randomise the antibody sequences. The term "mutagenesis" refers to any art recognized technique for altering a polynucleotide or polypeptide sequence. Preferred types of mutagenesis include error prone PCR mutagenesis, saturation mutagenesis, or other site directed mutagenesis.

The term "variant" shall specifically encompass functionally active variants.

The term "functionally active variant" of an antibody as used herein, means a sequence resulting from modification of this sequence (a parent antibody or a parent sequence) by insertion, deletion or substitution of one or more amino acids, or chemical derivatization of one or more amino acid residues in the amino acid sequence, or nucleotides within the nucleotide sequence, or at either or both of the distal ends of the sequence, and which modification does not affect (in particular impair) the activity of this sequence. In the case of a binding site having specificity to a selected target antigen, the functionally active variant of an antibody would still have the predetermined binding specificity, though this could be changed, e.g. to change the fine specificity to a specific epitope, the affinity, the avidity, the Kon or Koff rate, etc. Specifically the functionally active variants of an antibody of the invention has the polyspecific binding site that binds to Hla and at least one of the bi-component toxins of *S. aureus*, as further described herein.

Functionally active variants may be obtained, e.g. by changing the sequence of a parent antibody, e.g. an antibody comprising the same binding site as the antibody designated #AB-24, but with modifications within an antibody region besides the binding site, or derived from a parent antibody, which is the #AB-24 antibody, by a modification that does not impair the antigen binding, and preferably would have a biological activity similar to the parent antibody, including the ability to bind toxins of *S. aureus* and/or to neutralize *S. aureus* with a specific potency, e.g. with substantially the same biological activity, as determined by a specific binding assay or functional test to target *S. aureus* or *S. aureus* toxins. The term "substantially the same biological activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent antibody.

In a preferred embodiment the functionally active variant of a parent antibody a) is a biologically active fragment of the antibody, the fragment comprising at least 50% of the sequence of the molecule, preferably at least 70%, more preferably at least 80%, still more preferably at least 90%, even more preferably at least 95% and most preferably at least 97%, 98% or 99%;

b) is derived from the antibody by at least one amino acid substitution, addition and/or deletion, wherein the functionally active variant has a sequence identity to the molecule or part of it, such as an antibody of at least 50% sequence identity, preferably at least 60%, more preferably at least 70%, more preferably at least 80%, still more preferably at least 90%, even more preferably at least 95% and most preferably at least 97%, 98% or 99%; and/or c) consists of the antibody or a functionally active variant thereof and additionally at least one amino acid or nucleotide heterologous to the polypeptide or the nucleotide sequence.

In one preferred embodiment of the invention, the functionally active variant of the antibody according to the invention is essentially identical to the variant described above, but differs from its polypeptide or the nucleotide sequence, respectively, in that it is derived from a homologous sequence of a different species. These are referred to as naturally occurring variants or analogs.

The term "functionally active variant" also includes naturally occurring allelic variants, as well as mutants or any other non-naturally occurring variants. As is known in the art, an allelic variant is an alternate form of a (poly) peptide that is characterized as having a substitution, deletion, or addition of one or more amino acids that does essentially not alter the biological function of the polypeptide.

Functionally active variants may be obtained by sequence alterations in the polypeptide or the nucleotide sequence, e.g. by one or more point mutations, wherein the sequence alterations retains a function of the unaltered polypeptide or the nucleotide sequence, when used in combination of the invention. Such sequence alterations can include, but are not limited to, (conservative) substitutions, additions, deletions, mutations and insertions.

Specific functionally active variants are CDR variants. A CDR variant includes an amino acid sequence modified by at least one amino acid in the CDR region, wherein said modification can be a chemical or a partial alteration of the amino acid sequence, which modification permits the variant to retain the biological characteristics of the unmodified sequence. A partial alteration of the CDR amino acid sequence may be by deletion or substitution of one to several amino acids, e.g. 1, 2, 3, 4 or 5 amino acids, or by addition or insertion of one to several amino acids, e.g. 1, 2, 3, 4 or 5 amino acids, or by a chemical derivatization of one to several amino acids, e.g. 1, 2, 3, 4 or 5 amino acids, or combination thereof. The substitutions in amino acid residues may be conservative substitutions, for example, substituting one hydrophobic amino acid for an alternative hydrophobic amino acid.

Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc.

A point mutation is particularly understood as the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

Preferred point mutations refer to the exchange of amino acids of the same polarity and/or charge. In this regard, amino acids refer to twenty naturally occurring amino acids encoded by sixty-four triplet codons. These 20 amino acids can be split into those that have neutral charges, positive charges, and negative charges:

The "neutral" amino acids are shown below along with their respective three-letter and single-letter code and polarity:

Alanine: (Ala, A) nonpolar, neutral;
Asparagine: (Asn, N) polar, neutral;
Cysteine: (Cys, C) nonpolar, neutral;
Glutamine: (Gln, Q) polar, neutral;
Glycine: (Gly, G) nonpolar, neutral;
Isoleucine: (Ile, I) nonpolar, neutral;
Leucine: (Leu, L) nonpolar, neutral;
Methionine: (Met, M) nonpolar, neutral;
Phenylalanine: (Phe, F) nonpolar, neutral;
Proline: (Pro, P) nonpolar, neutral;
Serine: (Ser, S) polar, neutral;
Threonine: (Thr, T) polar, neutral;
Tryptophan: (Trp, W) nonpolar, neutral;
Tyrosine: (Tyr, Y) polar, neutral;
Valine: (Val, V) nonpolar, neutral; and
Histidine: (His, H) polar, positive (10%) neutral (90%).
The "positively" charged amino acids are:
Arginine: (Arg, R) polar, positive; and
Lysine: (Lys, K) polar, positive.
The "negatively" charged amino acids are:
Aspartic acid: (Asp, D) polar, negative; and
Glutamic acid: (Glu, E) polar, negative.

"Percent (%) amino acid sequence identity" with respect to the antibody sequences and homologs described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

An antibody variant is specifically understood to include homologs, analogs, fragments, modifications or variants with a specific glycosylation pattern, e.g. produced by glycoengineering, which are functional and may serve as functional equivalents, e.g. binding to the specific targets and with functional properties. The preferred variants as described herein are functionally active with regard to the antigen binding, preferably which have a potency to neutralize *S. aureus* and/or which are protective antibodies.

An antibody of the present invention may or may not exhibit Fc effector function. Though the mode of action is mainly mediated by neutralizing antibodies without Fc effector functions, Fc can recruit complement and aid elimination of the target antigen, such as a toxin, from the circulation via formation of immune complexes.

Specific antibodies may be devoid of an active Fc moiety, thus, either composed of antibody domains that do not contain an Fc part of an antibody or that do not contain an Fcgamma receptor binding site, or comprising antibody domains lacking Fc effector function, e.g. by modifications to reduce Fc effector functions, in particular to abrogate or reduce ADCC and/or CDC activity. Alternative antibodies may be engineered to incorporate modifications to increase Fc effector functions, in particular to enhance ADCC and/or CDC activity.

Such modifications may be effected by mutagenesis, e.g. mutations in the Fcgamma receptor binding site or by derivatives or agents to interfere with ADCC and/or CDC activity of an antibody format, so to achieve reduction or increase of Fc effector function.

A significant reduction of Fc effector function is typically understood to refer to Fc effector function of less than 10% of the unmodified (wild-type) format, preferably less than 5%, as measured by ADCC and/or CDC activity.

A significant increase of Fc effector function is typically understood to refer to an increase in Fc effector function of at least 10% of the unmodified (wild-type) format, preferably at least 20%, 30%, 40% or 50%, as measured by ADCC and/or CDC activity.

The term "glycoengineered" variants with respect to antibody sequences shall refer to glycosylation variants having modified immunogenic properties, ADCC and/or CDC as a result of the glycoengineering. All antibodies contain carbohydrate structures at conserved positions in the heavy chain constant regions, with each isotype possessing a distinct array of N-linked carbohydrate structures, which variably affect protein assembly, secretion or functional activity. IgG1 type antibodies are glyco-proteins that have a conserved N linked glycosylation site at Asn297 in each CH2 domain. The two complex bi-antennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC). Removal of N-Glycan at N297, e.g. through mutating N297, e.g. to A, or T299 typically results in aglycosylated antibody formats with reduced ADCC.

Major differences in antibody glycosylation occur between cell lines, and even minor differences are seen for a given cell line grown under different culture conditions. Expression in bacterial cells typically provides for an aglycosylated antibody. CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Nature Biotech. 17:176-180). In addition to the choice of host cells, factors that affect glycosylation during recombinant production of antibodies include growth mode, media formulation, culture density, oxygenation, pH, purification schemes and the like.

The term "antigen-binding site" or "binding site" refers to the part of an antibody that participates in antigen binding. The antigen binding site is formed by amino acid residues of the N-terminal variable ("V") regions of the heavy ("H") and/or light ("L") chains, or the variable domains thereof. Three highly divergent stretches within the V regions of the heavy and light chains, referred to as "hypervariable regions", are inter-posed between more conserved flanking stretches known as framework regions, The antigen-binding site provides for a surface that is complementary to the three-dimensional surface of a bound epitope or antigen, and the hypervariable regions are referred to as "complementarity-determining regions", or "CDRs." The binding site incorporated in the CDRs is herein also called "CDR binding site".

The term "antigen" as used herein interchangeably with the terms "target" or "target antigen" shall refer to a whole target molecule or a fragment of such molecule recognized by an antibody binding site. Specifically, substructures of an antigen, e.g. a polypeptide or carbohydrate structure, generally referred to as "epitopes", e.g. B-cell epitopes or T-cell epitope, which are immunologically relevant, may be recognized by such binding site.

The term "epitope" as used herein shall in particular refer to a molecular structure which may completely make up a specific binding partner or be part of a specific binding partner to a binding site of an antibody. An epitope may either be composed of a carbohydrate, a peptidic structure, a fatty acid, an organic, biochemical or inorganic substance or derivatives thereof and any combinations thereof. If an epitope is comprised in a peptidic structure, such as a peptide, a polypeptide or a protein, it will usually include at least 3 amino acids, preferably 5 to 40 amino acids, and more preferably between about 10-20 amino acids. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding the polypeptide to form a tertiary structure and the amino acids are not necessarily adjacent to one another in the linear sequence. Specifically and with regard to polypeptide antigens a conformational or discontinuous epitope is characterized by the presence of two or more discrete amino acid residues, separated in the primary sequence, but assembling to a consistent structure on the surface of the molecule when the polypeptide folds into the native protein/antigen.

Herein the term "epitope" shall particularly refer to the single epitope recognized by an antibody, or the mixture of epitopes comprising epitope variants, each recognized by a cross-reactive antibody.

The term "expression" is understood in the following way. Nucleic acid molecules containing a desired coding sequence of an expression product such as e.g. an antibody as described herein, and control sequences such as e.g. a promoter in operable linkage, may be used for expression purposes. Hosts transformed or transfected with these sequences are capable of producing the encoded proteins. In order to effect transformation, the expression system may be included in a vector; however, the relevant DNA may also be integrated into the host chromosome. Specifically the term refers to a host cell and compatible vector under suitable conditions, e.g. for the expression of a protein coded for by foreign DNA carried by the vector and introduced to the host cell.

Coding DNA is a DNA sequence that encodes a particular amino acid sequence for a particular polypeptide or protein such as e.g. an antibody. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes.

"Vectors" used herein are defined as DNA sequences that are required for the transcription of cloned recombinant nucleotide sequences, i.e. of recombinant genes and the translation of their mRNA in a suitable host organism.

An "expression cassette" refers to a DNA coding sequence or segment of DNA that code for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct".

Expression vectors comprise the expression cassette and additionally usually comprise an origin for autonomous replication in the host cells or a genome integration site, one or more selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The term "vector" as used herein includes autonomously replicating nucleotide sequences as well as genome integrating nucleotide sequences. A common type of vector is a "plasmid", which generally is a self-contained molecule of double-stranded DNA that can readily accept additional (foreign) DNA and which can readily be introduced into a suitable host cell. A plasmid vector often contains coding DNA and promoter DNA and has one or more restriction sites suitable for inserting foreign DNA. Specifically, the term "vector" or "plasmid" refers to a vehicle by which a DNA or RNA sequence (e.g. a foreign gene) can be introduced into a host cell, so as to transform the host and promote expression (e.g. transcription and translation) of the introduced sequence.

The term "host cell" as used herein shall refer to primary subject cells transformed to produce a particular recombinant protein, such as an antibody as described herein, and any progeny thereof. It should be understood that not all progeny are exactly identical to the parental cell (due to deliberate or inadvertent mutations or differences in environment), however, such altered progeny are included in these terms, so long as the progeny retain the same functionality as that of the originally transformed cell. The term "host cell line" refers to a cell line of host cells as used for expressing a recombinant gene to produce recombinant polypeptides such as recombinant antibodies. The term "cell line" as used herein refers to an established clone of a particular cell type that has acquired the ability to proliferate over a prolonged period of time. Such host cell or host cell line may be maintained in cell culture and/or cultivated to produce a recombinant polypeptide.

An "immune response" to a composition, e.g. an immunogenic composition, herein also termed "immunogen" comprising an antigen or epitope, or a vaccine as described herein is the development in the host or subject of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

A "protective immune response" is understood as an immune response that provides a significantly better outcome of an induced or natural infection or toxin challenge in comparison to that of the non-immune population. Protective immune response against toxins is mainly mediated by neutralizing antibodies having high affinity, e.g. with a Kd of less than $10^{-8}$M. The benefit of neutralization of toxins is the protection of targets cells and prevention of inflammation. Fc mediated immune complex formation can contribute as well by removing the toxin from the circulation (via the RES cells).

An immunogen or immunogenic composition usually comprises the antigen or epitope and a carrier, which may specifically comprise an adjuvant. The term "adjuvant" refers to a compound that when administered in conjunction with an antigen augments and/or redirects the immune response to the antigen, but when administered alone does not generate an immune response to the antigen. Adjuvants can augment an immune response by several mechanisms including lymphocyte recruitment, stimulation of B and/or T cells, and stimulation of macrophages. Exemplary carriers are liposomes or cationic peptides; exemplary adjuvants are aluminium phosphate or aluminium hydroxide, MF59 or CpG oligonucleotide.

The term "isolated" or "isolation" as used herein with respect to a nucleic acid, an antibody or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

With reference to polypeptides or proteins, such as antibodies or epitopes of the invention, the term "isolated" shall specifically refer to compounds that are free or substantially free of material with which they are naturally associated such as other compounds with which they are found in their natural environment, or the environment in which they are prepared (e g. cell culture) when such preparation is by recombinant DNA technology practiced in vitro or in vivo. Isolated compounds can be formulated with diluents or adjuvants and still for practical purposes be isolated—for example, the polypeptides or polynucleotides can be mixed with pharmaceutically acceptable carriers or excipients when used in diagnosis or therapy.

The term "neutralizing" or "neutralization" is used herein in the broadest sense and refers to any molecule that inhibits a pathogen, such as *S. aureus* from infecting a subject, or to inhibit the pathogen from promoting infections by producing potent protein toxins, or to inhibit the toxins from damaging a target cell in a subject, irrespective of the mechanism by which neutralization is achieved. Neutralization can be achieved, e.g., by an antibody that inhibits the binding and/or interaction of the *S. aureus* toxin(s) with its cognate receptor on target cells. In certain embodiments, the antibodies described herein can neutralize the toxin activity wherein the in vivo or in vitro effects of the interaction between the toxin and the target cell, such as red blood cells are reduced or eliminated. Neutralization can further occur by inhibition of forming active toxin, for example in the case of the *S. aureus* bi-component cytolysins, by inhibition of binding of the S- and F-components or formation of the oligomeric pores in cytomembranes.

The neutralization potency of antibodies against cytolytic toxins is typically determined in a standard assay by measuring increased viability or functionality of cells susceptible to the given toxin. Neutralization can be expressed by percent of viable cells with and without antibodies. For highly potent antibodies, a preferred way of expressing neutralization potency is the antibody:toxin molar ratio, where lower values correspond to higher potency. Values below 1 define very high potency.

The term "cross-neutralizing" as used herein shall refer to neutralizing a number of toxins, e.g. toxins incorporating a cross-reactive epitope recognized by the cross-reactive or polyspecific antibody.

The term "*Staphylococcus aureus*" or "*S. aureus*" or "pathogenic *S. aureus*" is understood in the following way. *Staphylococcus aureus* bacteria are normally found on the skin or in the nose of people and animals. The bacteria are generally harmless, unless they enter the body through a cut or other wound. Typically, infections are minor skin problems in healthy people. Historically, infections were treated by broad-spectrum antibiotics, such as methicillin. Now, though, certain strains have emerged that are resistant to methicillin and other beta-lactam antibiotics, such as penicillin and cephalosporins. They are referred to as methicillin-resistant *Staphylococcus aureus* (also known as multi-drug resistant *Staphylococcus aureus*, or "MRSA").

*Staphylococcus aureus*, an important human pathogen, expresses a multitude of secreted toxins (exotoxins). These can attack various host cell types, including erythrocytes, neutrophil granulocytes and other immune cells, as well as epithelial cells of the lung or skin. A prominent member of *S. aureus* toxins is alpha hemolysin (Ha), which exerts cytolytic function on lymphocytes, macrophages, lung epithelial cells and pulmonary endothelial cells.

*S. aureus* infections, including MRSA, generally start as small red bumps that resemble pimples, boils or spider bites. These bumps or blemishes can quickly turn into deep, painful abscesses that require surgical draining. Sometimes the bacteria remain confined to the skin. On occasion, they can burrow deep into the body, causing potentially life-threatening infections in a broad range of human tissue, including skin, soft tissue, bones, joints, surgical wounds, the bloodstream, heart valves, lungs, or other organs. Thus, *S. aureus* infections can result in disease conditions associated therewith, which are potentially fatal diseases, such as necrotizing fasciitis, endocarditis, sepsis, toxic shock syndrome, and various forms of pneumonia, including necrotizing pneumonia, and toxin production in furunculosis and carbunculosis. MRSA infection is especially troublesome in hospital or nursing home settings where patients are at risk of or prone to open wounds, invasive devices, and weakened immune systems and, thus, are at greater risk for infection than the general public.

Antibodies neutralizing *S. aureus* toxins are interfering with the pathogens and pathogenic reactions, thus able to limit or prevent infection and/or to amleiorate a disease condition resulting from such infection, or to inhibit *S. aureus* pathogenesis, in particular pneumonia pathogenesis. In this regard "protective antibodies" are understood herein as neutralizing antibodies that are responsible for immunity to an infectious agent observed in active or passive immunity. In particular, protective antibodies as described herein are able to neutralize toxic effects (such as cytolysis, induction of pro-inflammatory cytokine expression by target cells) of secreted virulence factors (exotoxins) and hence interfere with pathogenic potential of *S. aureus*.

The term "recombinant" as used herein shall mean "being prepared by or the result of genetic engineering". A recombinant host specifically comprises an expression vector or cloning vector, or it has been genetically engineered to contain a recombinant nucleic acid sequence, in particular employing nucleotide sequence foreign to the host. A recombinant protein is produced by expressing a respective recombinant nucleic acid in a host. The term "recombinant antibody", as used herein, includes antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant antibodies comprise antibodies engineered to include rearrangements and mutations which occur, for example, during antibody maturation.

As used herein, the term "specificity" or "specific binding" refers to a binding reaction which is determinative of the cognate ligand of interest in a heterogeneous population of molecules. Thus, under designated conditions (e.g. immunoassay conditions), an antibody specifically binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term is also applicable where e.g. an antibody is specific for a particular epitope which is cross-reactive a number of antigens, in which case the specific antibody will be able to bind to the various antigens carrying the cross-reactive epitope. Such binding site of an antibody or and antibody with a specificity to bind a cross-reactive epitope is also called a polyspecific or cross-specific binding site and antibody, respectively. For example, an antibody may have a polyspecific binding site specifically binding an epitope cross-reactive a number of different antigens with sequence homology within the epitope and/or structural similarities to provide for a conformational epitope of essentially the same structure, e.g. cross-reactive at least the Hla and a bi-component toxin of S. aureus.

The imrnunospecificity of an antibody, its binding capacity and the attendant affinity the antibody exhibits for a cross-reactive binding sequence, are determined by a cross-reactive binding sequence with which the antibody immunoreacts (binds). The cross-reactive binding sequence specificity can be defined, at least in part, by the amino acid residues of the variable region of the heavy chain of the immunoglobulin the antibody and/or by the light chain variable region amino acid residue sequence.

Use of the term "having the same specificity", "having the same binding site" or "binding the same epitope" indicates that equivalent monoclonal antibodies exhibit the same or essentially the same, i.e. similar immunoreaction (binding) characteristics and compete for binding to a pre-selected target binding sequence. The relative specificity of an antibody molecule for a particular target can be relatively determined by competition assays, e.g. as described in Harlow, et al., ANTIBODIES: A LABORATORY MANUAL, Cold Spring Harbor Laboratory Press, Cold Spring Harbor, N.Y., 1988).

The term "subject" as used herein shall refer to a warm-blooded mammalian, particularly a human being or a non-human animal. MRSA is a critically important human pathogen that is also an emerging concern in veterinary medicine. It is present in a wide range of non-human animal species. Thus, the term "subject" may also particularly refer to animals including dogs, cats, rabbits, horses, cattle, pigs and poultry. In particular the medical use of the invention or the respective method of treatment applies to a subject in need of prophylaxis or treatment of a disease condition associated with a S. aureus infection. The subject may be a patient at risk of a S. aureus infection or suffering from disease, including early stage or late stage disease. The term "patient" includes human and other mammalian subjects that receive either prophylactic or therapeutic treatment. The term "treatment" is thus meant to include both prophylactic and therapeutic treatment.

A subject is e.g. treated for prophylaxis or therapy of S. aureus disease conditions. In particular, the subject is treated, which is either at risk of infection or developing such disease or disease recurrence, or a subject that is suffering from such infection and/or disease associated with such infection.

Specifically the term "prophylaxis" refers to preventive measures which is intended to encompass prevention of the onset of pathogenesis or prophylactic measures to reduce the risk of pathogenesis.

Specifically, the method for treating, preventing, or delaying a disease condition in a subject as described herein, is by interfering with the pathogenesis of S. aureus as causal agent of the condition, wherein the pathogenesis includes a step of forming a pore on the subject's cellular membrane, e.g. by the specific virulence factors or toxins.

The term "toxin" as used herein shall refer to the alpha-toxin (Ha) and the bi-component toxins of S. aureus.

The virulence of S. aureus is due to a combination of numerous virulence factors, which include surface-associated proteins that allow the bacterium to adhere to eukaryotic cell membranes, a capsular polysaccharide that protects it from opsonophagocytosis, and several exotoxins. S. aureus causes disease mainly through the production of secreted virulence factors such as hemolysins, enterotoxins and toxic shock syndrome toxin. These secreted virulence factors suppress the immune response by inactivating many immunological mechanisms in the host, and cause tissue destruction and help establish the infection. The latter is accomplished by a group of pore forming toxins, the most prominent of which is Hla, a key virulence factor for S. aureus pneumonia.

S. aureus produces a diverse array of further virulence factors and toxins that enable this bacterium to neutralize and withstand attack by different kinds of immune cells, specifically subpopulations of white blood cells that make up the body's primary defense system. The production of these virulence factors and toxins allow S. aureus to maintain an infectious state. Among these virulence factors, S. aureus produces several bi-component leukotoxins, which damage membranes of host defense cells and erythrocytes by the synergistic action of two non-associated proteins or subunits. Among these bi-component toxins, gamma-hemolysin (HlgAB and HlgCB) and the Pantone-Valentine Leukocidin (PVL) are the best characterized.

The toxicity of the leukocidins towards mammalian cells involves the action of two components. The first subunit is named class S component, and the second subunit is named class F component. The S and F subunits act synergistically to form pores on white blood cells including monocytes, macrophages, dendritic cells and neutrophils (collectively known as phagocytes). The repertoire of bi-component leukotoxins produced by S. aureus is known to include cognate and non-cognate pairs of the F and S components, e.g. gamma-hemolysins, PVL toxins and PVL-like toxins, including HlgAB, HlgCB, LukSF, LukED, LukGH, LukS-HlgB, LukSD, HlgA-LukD, HlgA-LukF, LukG-HlgA, LukEF, LukE-HlgB, HlgC-LukD or HlgC-LukF, which are preferred targets as described herein. FIG. 1 provides an overview of some prominent bi-component toxins.

The term "substantially pure" or "purified" as used herein shall refer to a preparation comprising at least 50% (w/w), preferably at least 60%, 70%, 80%, 90% or 95% of a compound, such as a nucleic acid molecule or an antibody. Purity is measured by methods appropriate for the compound (e.g. chromatographic methods, polyacrylamide gel electrophoresis, HPLC analysis, and the like).

The term "therapeutically effective amount", used herein interchangeably with any of the terms "effective amount" or "sufficient amount" of a compound, e.g. an antibody or immunogen of the present invention, is a quantity or activity sufficient to, when administered to the subject effect beneficial or desired results, including clinical results, and, as such, an effective amount or synonym thereof depends upon the context in which it is being applied.

An effective amount is intended to mean that amount of a compound that is sufficient to treat, prevent or inhibit such diseases or disorder. In the context of disease, therapeutically effective amounts of the antibody as described herein are specifically used to treat, modulate, attenuate, reverse, or affect a disease or condition that benefits from an inhibition of *S. aureus* or *S. aureus* pathogenesis.

The amount of the compound that will correspond to such an effective amount will vary depending on various factors, such as the given drug or compound, the pharmaceutical formulation, the route of administration, the type of disease or disorder, the identity of the subject or host being treated, and the like, but can nevertheless be routinely determined by one skilled in the art.

The antibody or the immunogen of the present invention may be used prophylactically to inhibit onset of *S. aureus* infection, or therapeutically to treat *S. aureus* infection, particularly *S. aureus* infections such as MRSA that are known to be refractory or in the case of the specific subject, have proven refractory to treatment with other conventional antibiotic therapy.

A therapeutically effective amount of the antibody as described herein, such as provided to a human patient in need thereof, may specifically be in the range of 0.5-500 mg, preferably 1-400 mg, even more preferred up to 300 mg, up to 200 mg, up to 100 mg or up to 10 mg, though higher doses may be indicated e.g. for treating acute disease conditions.

Moreover, a treatment or prevention regime of a subject with a therapeutically effective amount of the antibody of the present invention may consist of a single administration, or alternatively comprise a series of applications. For example, the antibody may be administered at least once a year, at least once a half-year or at least once a month. However, in another embodiment, the antibody may be administered to the subject from about one time per week to about a daily administration for a given treatment. The length of the treatment period depends on a variety of factors, such as the severity of the disease, either acute or chronic disease, the age of the patient, the concentration and the activity of the antibody format. It will also be appreciated that the effective dosage used for the treatment or prophylaxis may increase or decrease over the course of a particular treatment or prophylaxis regime. Changes in dosage may result and become apparent by standard diagnostic assays known in the art. In some instances, chronic administration may be required.

An effective amount of an immunogen as described herein, such as provided to a patient at risk of developing a disease condition associated with an *S. aureus* infection, may specifically be in the range of 1-15 mg/kg per dose.

For example the immunogen may be administered as a first dose followed by one or more booster dose(s), within a certain timeframe, according to a prime-boost immunization scheme to induce a long-lasting, efficacious immune response to *S. aureus* infection. A preferred vaccination schedule would encompass administration of three doses, e.g. a first dose on day 0, a second dose on day 5-40, and a third dose on day 10-100, preferably on days 0, 28 and 90. According to a preferred accelerated schedule the administration may be on days 0, 7 and 14. Accelerated schedules may be indicated for prophylaxis, e.g. for patients facing elective surgery. Usually alum is used as an adjuvant, e.g. as phosphate or hydroxide.

Therefore, the invention specifically refers to monoclonal antibodies cross-neutralizing both alpha hemolysin and bi-component toxins of *S. aureus* with a sequence homology of 20-28%. This was surprising, because of the low level of sequence homology. The chance to generate mAbs cross-neutralizing Hla and at least one bi-component toxin was expected to be low.

Although the detailed mode-of-action remains to be elucidated, the data obtained for #AB-24 (#9028) are of great potential value and provide the first proof-of-concept of a single antibody neutralizing both alpha hemolysin and multiple bi-component toxins as well.

The only publication describing multiple bi-component specificity antibodies (Laventie, *PNAS*, 2011:16404) is considered to be non-relevant for the current invention, since the dual specificity for LukS and HlgC was generated by designing a bi-specific antibody utilizing two different binding sites. In contrast, the present invention refers to the same binding site which is able to bind to the different toxins, e.g. four different toxins: alpha-toxin and F-components of the gamma-hemolysin, the Panten Valentine leukocidin (PVL, LukSF) and and LukED. It is feasible that the quadruple reactive mAb also binds the bovine LukM leukocidin based on high amino acid homology to LukED and LukSF.

In some embodiments, the antibodies of the invention that recognize an epitope on Hla and cross-react with HlgA, may have additionally cross-reactivity with other staphylococcal leukocidin S compounds such as HlgC, LukS-PVL, LukHLukS-I, LukE, LukEv, and LukM. Likewise, in some embodiments, the antibodies of the invention that recognize an epitope on Hla and cross-react with HlgB, may have additionally cross-reactivity other staphylococcal leukocidin F compounds such as LukF'-PV, LukF-PV, LukDv, LukD, LukF-I, and LukG. Cross-reactive anti-HlgA and/or anti-HlgB antibodies of the invention may inhibit or reduce HlgA activity and HlgB activity, respectively. In some embodiments, the cross-reactive anti-HlgA and/or anti-HlgB antibodies neutralize, e.g. substantially eliminate, HlgA and HlgB activity, respectively.

According to a specific aspect, there is provided an antibody binding the same epitope, which term includes variants binding to essentially the same epitope, as the antibody designated #AB-24, or comprising the same binding site, which term includes variants comprising essentially the same binding site, as the antibody designated #AB-24. The #AB-24 antibody and functionally active variants would particularly comprise a binding site potently neutralizing Hla and cross-neutralizing at least one of, at least two of or at least the three cognate toxin pairs LukS-LukF, LukE-LukD, and HlgB-HlgC, and possibly further bi-component toxins.

Antibodies are said to "bind to the same epitope" or "comprising the same binding site" or have "essentially the same binding" characteristics, if the antibodies cross-compete so that only one antibody can bind to the epitope at a given point of time, i.e. one antibody prevents the binding or modulating effect of the other.

The term "compete" or "cross-compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope, whether to the same, greater, or lesser extent, the antibodies are said to "cross-compete" with each other for binding of their respective epitope(s). Both competing and cross-competing antibodies are encompassed by the present invention.

Competition herein means a greater relative inhibition than about 30% as determined by competition ELISA analysis, e.g. as described in the Examples section. It may be desirable to set a higher threshold of relative inhibition as criteria of what is a suitable level of competition in a particular context, e.g., where the competition analysis is used to select or screen for new antibodies designed with the intended function of the binding of additional or other toxins of S. aureus. Thus, for example, it is possible to set criteria for the competitive binding, wherein at least 40% relative inhibition is detected, or at least 50%, at least 60%, at least 70%, at least 80%, at least 90% or even at least 100%, before an antibody is considered sufficiently competitive.

Specifically, there is provided an antibody comprising the variable region of the antibody designated #AB-24, in particular at least one of the CDR sequences, preferably at least two, at least 3, at least 4, at least 5 or at least six of the CDR sequences, or CDR variants thereof which are functionally active. More specifically, there is provided the antibody designated #AB-24.

Specifically, the #AB-24 antibody or any functionally active variant thereof may be produced employing the deposited material, such as one of or both of the deposited plasmids and/or one of or both of the deposited host cells.

According to a specific aspect, the antibody may be derived from an antibody encoded by the plasmid of the invention e.g. employing a partial sequence of the deposited material to engineer the #AB-24 antibody or any functionally active variant thereof.

According to a further specific aspect, the #AB-24 antibody or any functionally active variant thereof may be derived from an antibody produced by a host cell deposited under DSM 26747 and/or DSM 26748, e.g. employing a partial sequence of the deposited material to engineer the #AB-24 antibody or any functionally active variant thereof.

Specifically, the #AB-24 variant is a CDR variant that is functionally active, e.g. with partial alterations in at least one of the CDR sequences.

In certain aspects, the invention provides for such variant antibodies, preferably monoclonal antibodies, most preferably human antibodies, comprising a heavy chain and a light chain, wherein any of the heavy chain or VH variable region or the respective CDRs comprises an amino acid sequence as derived from the respective deposited plasmid and/or from the respective deposited host cell.

In certain aspects, the invention provides for such variant antibodies, preferably monoclonal antibodies, most preferably human antibodies, comprising a heavy chain and a light chain, wherein any of the light chain or VL variable region or the respective CDRs comprises an amino acid sequence as derived from the respective deposited plasmid and/or from the respective deposited host cell.

In certain aspects, the invention provides for such variant antibodies, preferably monoclonal antibodies, most preferably human antibodies, comprising a heavy chain and a light chain, wherein any of the heavy and light chain, or the VH/VL variable regions, or the respective CDRs comprises an amino acid sequence as derived from the respective deposited plasmids and/or from the respective deposited host cells.

In certain aspects, the invention also provides for such variant antibodies, comprising the respective binding sequences, such as the variable sequences and/or the CDR sequences, as derived from the deposited material, wherein the binding sequences comprises a sequence that has at least 70%, or at least 80%, or at least 90%, or at least 95%, or at least 99% identity to the amino acid sequence as derived from the deposited material, and wherein the variant is a functionally active variant.

As described herein, in one aspect the invention provides antibody molecules characterized by, e.g. the ability to compete with monoclonal antibody #AB-24 for binding to Hla, LukSF, LukED and HigCB. #AB-24 is a human IgG1 antibody, which the inventors isolated and characterized. The mature heavy variable chain of #AB-24 is e.g. produced employing the host cell of DSM 26747. The mature light variable chain of #AB-24 is e.g. produced employing the host cell of DSM 26748.

Preferred antibodies of the invention are binding said individual antigens with a high affinity, in particular with a high on and/or a low off rate, or a high avidity of binding. The binding affinity of an antibody is usually characterized in terms of the concentration of the antibody, at which half of the antigen binding sites are occupied, known as the dissociation constant (Kd, or $K_D$). Usually a binder is considered a high affinity binder with a Kd<$10^{-8}$ M, preferably a Kd<$10^{-9}$ M, even more preferred is a Kd<$10^{-10}$ M.

Yet, in a particularly preferred embodiment the individual antigen binding affinities are of medium affinity, e.g. with a Kd of less than $10^{-6}$ and up to $10^{-8}$ M, e.g. when binding to at least two antigens.

Medium affinity binders may be provided according to the invention, preferably in conjunction with an affinity maturation process, if necessary.

Affinity maturation is the process by which antibodies with increased affinity for a target antigen are produced. Any one or more methods of preparing and/or using affinity maturation libraries available in the art may be employed in order to generate affinity matured antibodies in accordance with various embodiments of the invention disclosed herein. Exemplary such affinity maturation methods and uses, such as random mutagenesis, bacterial mutator strains passaging, site-directed mutagenesis, mutational hotspots targeting, parsimonious mutagenesis, antibody shuffling, light chain shuffling, heavy chain shuffling, CDR1 and/or CDR1 mutagenesis, and methods of producing and using affinity maturation libraries amenable to implementing methods and uses in accordance with various embodiments of the invention disclosed herein, include, for example, those disclosed in: Prassler et al. (2009); Immunotherapy, Vol. 1(4), pp. 571-583; Sheedy et al. (2007), Biotechnol. Adv., Vol. 25(4), pp. 333-352; WO2012/009568; WO2009/036379; WO2010/105256; US2002/0177170; WO2003/074679.

With structural changes of an antibody, including amino acid mutagenesis or as a consequence of somatic mutation in immunoglobulin gene segments, variants of a binding site to an antigen are produced and selected for greater affinities. Affinity matured antibodies may exhibit a several logfold greater affinity than a parent antibody. Single parent antibodies may be subject to affinity maturation. Alternatively pools of antibodies with similar binding affinity to the target antigen may be considered as parent structures that are varied to obtain affinity matured single antibodies or affinity matured pools of such antibodies.

The preferred affinity matured variant of an antibody according to the invention exhibits at least a 10 fold increase in affinity of binding, preferably at least a 100 fold increase. The affinity maturation may be employed in the course of the selection campaigns employing respective libraries of parent molecules, either with antibodies having medium binding affinity to obtain the antibody of the invention having the specific target binding property of a binding affinity Kd<$10^{-8}$ M. Alternatively, the affinity may be even more increased by affinity maturation of the antibody according to the invention to obtain the high values corresponding to a Kd of less than $10^{-9}$ M, preferably less than $10^{-10}$ M or even less than $10^{-11}$ M, most preferred in the picomolar range.

Phagocytic effector cells may be activated through another route employing activation of complement. Antibodies that bind to surface antigens on microorganisms attract the first component of the complement cascade with their Fc region and initiate activation of the "classical" complement system. These results in the stimulation of phagocytic effector cells, which ultimately kill the target by complement dependent cytotoxicity (CDC).

According to a specific embodiment, the antibody of the invention has a cytotoxic activity in the presence of immune-effector cells as measured in a standard ADCC or CDC assay. A cytotoxic activity as determined by either of an ADCC or CDC assay may be shown for an antibody of the invention, if there is a significant increase in the percentage of cytolysis as compared to a control. The cytotoxic activity related to ADCC or CDC is preferably measured as the absolute percentage increase, which is preferably higher than 5%, more preferably higher than 10%, even more preferred higher than 20%.

The invention specifically provides for cross-reactive antibodies, which are obtained by a process identify neutralizing antibodies with multiple specificities, e.g. by a cross-reactive discovery selection scheme. Accordingly, an antibody library including antibodies showing reactivity with two targets, targets A and B, may first be selected for reactivity with one of the targets, e.g. target A, followed by selection for reactivity with the other target, e.g. target B. Each successive selection round reinforces the reactive strength of the resulting pool towards both targets. Accordingly, this method is particularly useful for identifying antibodies with cross-reactivity directed to the two different targets, and the potential to cross-neutralize a pathogen. The method can be extended to identifying antibodies showing reactivity towards further targets, by including additional rounds of enrichment towards the additional target(s).

Cross-reactive antibodies, in some instances, emerge through screening against single antigens. To increase the likelihood of isolating cross-reactivity clones one would apply multiple selective pressures by processively screening against multiple antigens. Special mAb selection strategies employ the different toxin components in an alternating fashion. For example, most potent neutralizing anti-Hla mAbs are then tested for binding to PVL and PVL like toxins on human neutrophils, which represent the major target for bi-component toxins during *S. aureus* infection.

The recombinant toxins may be used for selecting antibodies from an antibody library, e.g. a yeast-displayed antibody library.

In either event cross-reactivity can be further improved by antibody optimization methods known in the art. For example, certain regions of the variable regions of the immunoglobulin chains described herein may be subjected to one or more optimization strategies, including light chain shuffling, destinational mutagenesis, CDR amalgamation, and directed mutagenesis of selected CDR and/or framework regions.

Screening methods for identifying antibodies with the desired neutralizing properties may be inhibition of toxin binding to the target cells, inhibition of formation of dimers or oligomers. Inhibition of pore formation, inhibition of cell lysis, inhibition of the induction of cytokines, lymphokines, and any pro-inflammatory signaling, and/or inhibition of in vivo effect on animals (death, hemolysis, overshooting inflammation, organ dysfunction. Reactivity can be assessed based on direct binding to the desired toxins, e.g. using standard assays.

Once cross-neutralizing antibodies with the desired properties have been identified, the dominant epitope or epitopes recognized by the antibodies may be determined. Methods for epitope mapping are well-known in the art and are disclosed, for example, in *Epitope Mapping: A Practical Approach*, Westwood and Hay, eds., Oxford University Press, 2001.

Epitope mapping concerns the identification of the epitope to which an antibody binds. There are many methods known to those of skill in the art for determining the location of epitopes on proteins, including crystallography analysis of the antibody-antigen complex, competition assays, gene fragment expression assays, and synthetic peptide-based assays. An antibody that "binds the same epitope" as a reference antibody is herein understood in the following way. When two antibodies recognize epitopes that are identical or sterically overlapping epitopes, the antibodies are referred to as binding the same or essentially the same or substantially the same epitopes. A commonly used method for determining whether two antibodies bind to identical or sterically overlapping epitopes is the competition assay, which can be con-figured in all number of different formats, using either labeled antigen or labeled antibody. Usually, an antigen is immobilized on a 96-well plate, and the ability of unlabeled antibodies to block the binding of labeled antibodies is measured using radioactive or enzyme labels.

Once antibodies with the desired cross-neutralizing properties are identified, such antibodies, including antibody fragments can be produced by methods well-known in the art, including, for example, hybridoma techniques or recombinant DNA technology.

In the hybridoma method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Recombinant monoclonal antibodies can, for example, be produced by isolating the DNA encoding the required antibody chains and transfecting a recombinant host cell with the coding sequences for expression, using well known recombinant expression vectors, e.g. the plasmids of the invention or expression cassette(s) comprising the nucleotide sequences encoding the antibody sequences. Recombinant host cells can be prokaryotic and eukaryotic cells, such as those described above.

According to a specific aspect, the nucleotide sequence may be used for genetic manipulation to humanize the antibody or to improve the affinity, or other characteristics of the antibody. For example, the constant region may be engineered to more nearly resemble human constant regions to avoid immune response, if the antibody is used in clinical trials and treatments in humans. It may be desirable to genetically manipulate the antibody sequence to obtain greater affinity to the target toxins and greater efficacy against *S. aureus*. It will be apparent to one of skill in the art that one or more polynucleotide changes can be made to the antibody and still maintain its binding ability to the target toxins.

The production of antibody molecules, by various means, is generally well understood. U.S. Pat. No. 6,331,415 (Cabilly et al.), for example, describes a method for the recombinant production of antibodies where the heavy and light chains are expressed simultaneously from a single vector or from two separate vectors in a single cell. Wibbenmeyer et al., (1999, Biochim Biophys Acta 1430(2):191-202) and Lee and Kwak (2003, J. Biotechnology 101:189-198) describe the production of monoclonal antibodies from separately produced heavy and light chains, using plasmids expressed in separate cultures of *E. coli*. Various other techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

If desired, the antibody of the invention, e.g. the #AB-24 antibody may be sequenced and the polynucleotide sequence may then be cloned into a vector for expression or propagation. The sequence encoding the antibody may be maintained in vector in a host cell and the host cell can then be expanded and frozen for future use. Production of recombinant monoclonal antibodies in cell culture can be carried out through cloning of antibody genes from B cells by means known in the art.

In another aspect, the invention provides an isolated nucleic acid comprising a sequence that codes for production of the recombinant antibody of the present invention.

In another aspect, the invention provides an isolated nucleic acid comprising a sequence that codes for production of the recombinant epitope of the present invention, or a molecule comprising such epitope of the present invention. However, the epitope of the invention may also be synthetically produced, e.g. through any of the synthesis methods well-known in the art.

An antibody or epitope encoding nucleic acid can have any suitable characteristics and comprise any suitable features or combinations thereof. Thus, for example, an antibody or epitope encoding nucleic acid may be in the form of DNA, RNA, or a hybrid thereof, and may include non-naturally-occurring bases, a modified backbone, e.g., a phosphorothioate backbone that promotes stability of the nucleic acid, or both. The nucleic acid advantageously may be incorporated in an expression cassette, vector or plasmid of the invention, comprising features that promote desired expression, replication, and/or selection in target host cell(s). Examples of such features include an origin of replication component, a selection gene component, a promoter component, an enhancer element component, a polyadenylation sequence component, a termination component, and the like, numerous suitable examples of which are known.

The present disclosure further provides the recombinant DNA constructs comprising one or more of the nucleotide sequences described herein. These recombinant constructs are used in connection with a vector, such as a plasmid, phagemid, phage or viral vector, into which a DNA molecule encoding any disclosed antibody is inserted.

Monoclonal antibodies are produced using any method that produces antibody molecules by continuous cell lines in culture. Examples of suitable methods for preparing monoclonal antibodies include the hybridoma methods of Kohler et al. (1975, Nature 256:495-497) and the human B-cell hybridoma method (Kozbor, 1984, J. Immunol. 133:3001; and Brodeur et al., 1987, Monoclonal Antibody Production Techniques and Applications, (Marcel Dekker, Inc., New York), pp. 51-63).

The invention moreover provides pharmaceutical compositions which comprise an antibody or an immunogen as described herein and a pharmaceutically acceptable carrier or excipient. These pharmaceutical compositions can be administered in accordance with the present invention as a bolus injection or infusion or by continuous infusion. Pharmaceutical carriers suitable for facilitating such means of administration are well known in the art.

Pharmaceutically acceptable carriers generally include any and all suitable solvents, dispersion media, coatings, antibacterial and antifungal agents, isotonic and absorption delaying agents, and the like that are physiologically compatible with an antibody or related composition or combination provided by the invention. Further examples of pharmaceutically acceptable carriers include sterile water, saline, phosphate buffered saline, dextrose, glycerol, ethanol, and the like, as well as combinations of any thereof.

In one such aspect, an antibody can be combined with one or more carriers appropriate a desired route of administration, antibodies may be, e.g. admixed with any of lactose, sucrose, starch, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, polyvinyl alcohol, and optionally further tabletted or encapsulated for conventional administration. Alternatively, an antibody may be dissolved in saline, water, polyethylene glycol, propylene glycol, carboxymethyl cellulose colloidal solutions, ethanol, corn oil, peanut oil, cotton-seed oil, sesame oil, tragacanth gum, and/or various buffers. Other carriers, adjuvants, and modes of administration are well known in the pharmaceutical arts. A carrier may include a controlled release material or time delay material, such as glyceryl monostearate or glyceryl distearate alone or with a wax, or other materials well known in the art.

Additional pharmaceutically acceptable carriers are known in the art and described in, e.g. REMINGTON'S PHARMACEUTICAL SCIENCES. Liquid formulations can be solutions, emulsions or suspensions and can include excipients such as suspending agents, solubilizers, surfactants, preservatives, and chelating agents.

Pharmaceutical compositions are contemplated wherein an antibody or immunogen of the present invention and one or more therapeutically active agents are formulated. Stable formulations of the antibody or immunogen of the present invention are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are specifically sterile, preferably in the form of a sterile aqueous solution. This is readily accomplished by filtration through sterile filtration membranes or other methods. The antibody and other therapeutically active agents disclosed herein may also be formulated as immunoliposomes, and/or entrapped in microcapsules.

Administration of the pharmaceutical composition comprising an antibody or immunogen of the present invention, may be done in a variety of ways, including orally, subcutaneously, intravenously, intranasally, intraotically, transdermally, mucosal, topically, e.g., gels, salves, lotions, creams, etc., intraperitoneally, intramuscularly, intrapulmonary, e.g.

employing inhalable technology or pulmonary delivery systems, vaginally, parenterally, rectally, or intraocularly.

Exemplary formulations as used for parenteral administration include those suitable for subcutaneous, intramuscular or intravenous injection as, for example, a sterile solution, emulsion or suspension.

In one embodiment, the antibody or immunogen of the present invention is the only therapeutically active agent administered to a subject, e.g. as a disease modifying or preventing monotherapy.

Alternatively, the antibody or immunogen of the present invention is administered in combination with one or more other therapeutic or prophylactic agents, including but not limited to standard treatment, e.g. antibiotics, steroid and non-steroid inhibitors of inflammation, and/or other antibody based therapy, e.g. employing antibacterial or anti-inflammatory agents.

A combination therapy is particularly employing a standard regimen, e.g. as used for treating MRSA infection. This may include antibiotics, e.g. tygecycline, linezolide, methicillin and/or vancomycin.

In a combination therapy, the antibody may be administered as a mixture, or concomitantly with one or more other therapeutic regimens, e.g. either before, simultaneously or after concomitant therapy.

Prophylactic administration of immunogens in some cases may employ a vaccine comprising the immunogen of the present invention, i.e. a monovalent vaccine. Yet, a multivalent vaccine comprising different immunogens to induce an immune response against the same or different target pathogens may be used.

The biological properties of the antibody, the immunogen or the respective pharmaceutical preparations of the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic or as a prophylactic with the appropriate half-life, effector function, (cross-)neutralizing activity and/or immune response upon active or passive immunotherapy. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the subject agent or composition. Tests in humans are ultimately required for approval as drugs, and thus of course these experiments are contemplated. Thus, the antibody, immunogen and respective pharmaceutical compositions of the present invention may be tested in humans to determine their therapeutic or prophylactic efficacy, toxicity, immuno-genicity, pharmacokinetics, and/or other clinical properties.

The invention also provides the subject antibody of the invention for diagnostic purposes, e.g. for use in methods of detecting and quantitatively determining the concentration of a toxin or antibody as immunoreagent or target in a biological fluid sample.

The invention also provides methods for detecting the level of toxins or S. aureus infection in a biological sample, such as a body fluid, comprising the step of contacting the sample with an antibody of the invention. The antibody of the invention may be employed in any known assay method, such as competitive binding assays, direct and indirect sandwich assays, immunoprecipitation assays and enzyme-linked immunosorbent assays (ELISA).

A body fluid as used according to the present invention includes biological samples of a subject, such as tissue extract, urine, blood, serum, stool and phlegm.

In one embodiment the method comprises contacting a solid support with an excess of a certain type of antibody fragment which specifically forms a complex with a target, such as at least one of the toxins targeted by the antibody of the invention, conditions permitting the antibody to attach to the surface of the solid support. The resulting solid support to which the antibody is attached is then contacted with a biological fluid sample so that the target in the biological fluid binds to the antibody and forms a target-antibody complex. The complex can be labeled with a detectable marker. Alternatively, either the target or the antibody can be labeled before the formation the complex. For example, a detectable marker (label) can be conjugated to the antibody. The complex then can be detected and quantitatively determined thereby detecting and quantitatively determining the concentration of the target in the biological fluid sample.

For particular applications the antibody of the invention is conjugated to a label or reporter molecule, selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Antibodies conjugated to labels or reporter molecules may be used, for instance, in assay systems or diagnostic methods, e.g. to diagnose S. aureus infection or disease conditions associated therewith.

The antibody of the invention may be conjugated to other molecules which allow the simple detection of said conjugate in, for instance, binding assays (e.g. ELISA) and binding studies.

Another aspect of the present invention provides a kit comprising an antibody, which may include, in addition to one or more antibodies, various diagnostic or therapeutic agents. A kit may also include instructions for use in a diagnostic or therapeutic method. Such instructions can be, for example, provided on a device included in the kit, e.g. tools or a device to prepare a biological sample for diagnostic purposes, such as separating a cell and/or protein containing fraction before determining the respective toxin(s) to diagnose a disease. Advantageously, such a kit includes an antibody and a diagnostic agent or reagent that can be used in one or more of the various diagnostic methods described herein. In another preferred embodiment, the kit includes an antibody, e.g. in the lyophilized form, in combination with pharmaceutically acceptable carrier(s) that can be mixed before use to form an injectable composition for near term administration.

The antibody designated #AB-24 (herein also referred to as #9028), specifically the antibody light chain and/or heavy chain, is further characterized by the biological material deposited at the DSMZ—Deutsche Sammlung von Mikroorganismen und Zellkulturen, Mascheroder Weg 1 b/Inhoffenstraße 7B, 38124 Braunschweig (DE) under the accession numbers as indicated herein.

DSM 26747 is an E. coli host cell transformed with a plasmid comprising the coding sequence of the #AB-24 heavy chain (AB-24-HC): *Escherichia coli* DH5alpha AB-24-HC=DSM 26747, deposition date: Jan. 8, 2013; depositor: Arsanis Biosciences GmbH, Vienna, Austria.

DSM 26748 is an *E. coli* host cell transformed with a plasmid comprising the coding sequence of the #AB-24 light chain (AB-24-LC): *Escherichia coli* DH5alpha AB-24-LC=DSM 26748; deposition date: Jan. 8, 2013; depositor: Arsanis Biosciences GmbH, Vienna, Austria.

The subject matter of the following definitions is considered embodiments of the present invention:

1. A cross-neutralizing antibody comprising at least one polyspecific binding site that binds to alpha-toxin (Ha) and at least one of the bi-component toxins of *Staphylococcus aureus*.

2. Antibody according to definition 1, wherein said bi-component toxin is selected from the group consisting of cognate and non-cognate pairs of F and S components of gamma-hemolysins, PVL toxins and PVL-like toxins, preferably any of HlgAB, HlgCB, LukSF, LukED, LukGH, LukS-HlgB, LukSD, HlgA-LukD, HlgA-LukF, LukG-HlgA, LukEF, LukE-HlgB, HlgC-LukD or HlgC-LukF.

3. Antibody according to definition 1 or 2, wherein said binding site binds to at least two or at least three bi-component toxins, preferably at least two or three of any of HlgAB, HlgCB, LukSF and LukED, preferably HlgAB, HlgCB, LukSF and LukED.

4. Antibody according to any of definitions 1 to 3, wherein said binding site is a CDR binding site, preferably comprising the CDR sequences of a VH and/or a VL binding site.

5. Antibody according to any of definitions 1 to 4, which is a full-length monoclonal antibody or an antibody fragment thereof comprising at least one antibody domain incorporating the binding site, preferably an antibody selected from the group consisting of murine, chimeric, humanized or human antibodies, heavy-chain antibodies, Fab, Fd, scFv and single-domain antibodies like VH, VHH or VL, preferably a human IgG1 antibody.

6. Antibody according to any of definitions 1 to 5, which has an affinity to bind each of the toxins with a Kd of less than $10^{-8}$M, preferably less than $10^{-9}$M.

7. Antibody according to any of definitions 1 to 6, which exhibits in vitro neutralization potency in a cell-based assay with an 1050 of less than 50:1 mAb:toxin ratio (mol/mol), preferably less than 10:1, more preferably less than 1:1.

8. Antibody according to any of definitions 1 to 7, which neutralizes the targeted toxins in animals and inhibits *S. aureus* pathogenesis in vivo, preferably any of pneumonia, bacteremia or sepsis, peritonitis and osteomyelitis.

9. Antibody according to any of definitions 1 to 8, wherein the antibody binds the same epitope as an antibody designated #AB-24.

10. Antibody according to any of definitions 1 to 9, wherein the antibody comprises the same binding site as an antibody designated #AB-24.

11. Antibody according to any of definitions 1 to 10, wherein the antibody is derived from an antibody produced by a host cell deposited under DSM 26747 and/or DSM 26748, or a functionally active variant thereof.

12. Antibody according to definition 11, comprising
(a) an antibody light chain produced by a host cell deposited under DSM 26748; and/or
(b) an antibody heavy chain produced by a host cell deposited under DSM 26747;
(c) or a functionally active variant of (a) and/or (b).

13. A plasmid comprising a nucleotide sequence
encoding an antibody light chain designated #AB-24-LC comprised in a host cell deposited under DSM 26748; and/or
encoding an antibody heavy chain designated #AB-24-HC comprised in a host cell deposited under DSM 26747.

14. An expression cassette comprising a coding sequence to express a light chain and/or heavy chain of an antibody according to any of definitions 1 to 12, which expression cassette or coding sequence is derived from the plasmid according to definition 13.

15. Method of producing an antibody according to any of definitions 1 to 12, wherein a host cell is transformed with the plasmid of definition 13 or the expression cassette according to definition 14.

16. A host cell comprising the plasmid according to definition 13 or the expression cassette according to definition 14.

17. The host cell according to definition 16, which is deposited under DSM 26747 or DSM 26748.

18. Method of producing an antibody according to any of definitions 1 to 12, wherein a host cell according to definition 16 or 17 is cultivated or maintained under conditions to produce said antibody.

19. A method of identifying a candidate protective antibody comprising:
(a) providing a sample containing an antibody or antibody-producing cell; and
(b) assessing for binding of an antibody in or produced by the sample with an epitope recognized by the antibody designated #AB-24, wherein a positive reaction between the antibody and the epitope identifies the antibody as candidate protective antibody.

20. A method of identifying a candidate protective antibody comprising:
(a) providing a sample containing an antibody or antibody-producing cell; and
(b) assessing for binding of an antibody in or produced by the sample with alpha-toxin and at least one of a bi-component toxin of *Staphylococcus aureus*, wherein a positive reaction between the antibody and the toxins identifies the antibody as candidate protective antibody.

21. A method of producing an antibody according to any of definition 1 to 12, comprising
(a) providing a candidate protective antibody identified according to definition 19 or 20; and
(b) producing a monoclonal antibody, or a humanized or human form of the candidate protective antibody, or a derivative thereof with the same epitope binding specificity as the candidate protective antibody.

22. A method of producing an antibody according to any of definition 1 to 12, comprising
(a) immunizing a non-human animal with an epitope recognized by the antibody designated #AB-24;
(b) forming immortalized cell lines from the isolated B-cells;
(c) screening the cell lines obtained in b) to identify a cell line producing a monoclonal antibody that binds to the epitope; and
(d) producing the monoclonal antibody, or a humanized or human form of the antibody, or a derivative thereof with the same epitope binding specificity as the monoclonal antibody.

23. A method of producing an antibody according to any of definition 1 to 12, comprising
(a) immunizing a non-human animal with alpha-toxin and at least one of a bi-component toxin of *Staphylococcus aureus* and isolating B-cells producing antibodies;
(b) forming immortalized cell lines from the isolated B-cells;
(c) screening the cell lines to identify a cell line producing a monoclonal antibody that binds to alpha-toxin and at least one of a bi-component toxin of *Staphylococcus aureus*; and
(d) producing the monoclonal antibody, or a humanized or human form of the antibody, or a derivative thereof with the same epitope binding specificity as the monoclonal antibody.

24. Antibody according to any of definitions 1 to 12, for use in treating a subject at risk of or suffering from a *S. aureus* infection comprising administering to the subject an effective amount of the antibody to limit the infection in the subject, to ameliorate a disease condition resulting from said infection or to inhibit *S. aureus* pneumonia pathogenesis.

25. Antibody for use according to definition 25, for protecting against *S. aureus* infections.

26. Antibody for use according to definition 24 or 25, wherein the antibody is administered in a parenteral or mucosal formulation.

27. Pharmaceutical preparation of an antibody according to any of definitions 1 to 12, preferably comprising a parenteral or mucosal formulation, optionally containing a pharmaceutically acceptable carrier or excipient.

28. Antibody according to any of definitions 1 to 12, for diagnostic use to detect any *S. aureus* infections, including high toxin producing MRSA infections, such as necrotizing pneumonia, and toxin production in furunculosis and carbunculosis.

29. Antibody for use according to definition 28, wherein a systemic infection with *S. aureus* in a subject is determined ex vivo by contacting a sample of body fluid of said subject with the antibody, wherein a specific immune reaction of the antibody determines the infection.

30. Diagnostic preparation of an antibody according to any of definitions 1 to 12, optionally containing the antibody with a label and/or a further diagnostic reagent with a label.

31. Isolated conformational epitope recognized by an antibody designated #AB-24.

32. An immunogen comprising:
(a) an epitope according to definition 31;
(b) optionally further epitopes not natively associated with said epitope of (a); and
(c) a carrier.

33. Immunogen according to definition 32, wherein said carrier is a pharmaceutically acceptable carrier, preferably comprising buffer and/or adjuvant substances.

34. Immunogen according to definition 32 or 33, in a vaccine formulation, preferably for parenteral use.

35. Immunogen according to any of definitions 32 to 34, for use in treating a subject by administering an effective amount of said immunogen to protect the subject from an *S. aureus* infection, to prevent a disease condition resulting from said infection or to inhibit *S. aureus* pneumonia pathogenesis.

36. Immunogen according to definition 35, for eliciting a protective immune response.

37. Isolated nucleic acid encoding an antibody according to any of definitions 1 to 12 or an epitope according to definition 31.

The foregoing description will be more fully understood with reference to the following examples. Such examples are, however, merely representative of methods of practicing one or more embodiments of the present invention and should not be read as limiting the scope of invention.

EXAMPLES

Example 1: Generation of Recombinant Toxins

Ten *S-aureus* toxins—Hla, LukF, LukD, LukS, LukE, HlgA, HlgC, HlgB, LukG and LukH—were produced recombinantly in *E. coli* (BL21, Rosetta or Tuner DE3) (FIG. 1). Toxin genes for the mature proteins (determined using the SignalP 4.1 Server; www.cbs.dtu.dk) were codon optimized for *E. coli* expression and generated by gene synthesis based on published genome sequences of *Staphylococcus aureus* strains USA300_TCH1516, MRSA252 and MSHR1314 (SeqIDs 1 to 28, FIG. 9). All toxins, except for LukG and LukH, were expressed in soluble form with an N-terminal NusA/His$_6$ tag which was removed proteolitically. Purification consisted typically of three chromatographic steps 1) IMAC (Immobilized metal affinity column) 2) cation exchange or IMAC, and 3) size exclusion chromatography. LukG and LukH were expressed without tags in insoluble form, the proteins were refolded from inclusion bodies and purified; purification consisted of two steps on the size exclusion column for LukH and one step on cation exchange and one on anion exchange at pH 10.2-11.0 for LukG.

The proteins were assayed for purity (by SDS-PAGE) and monomeric state (by size exclusion) and their secondary structure (determined by circular dichroism) was compared with literature data, where available. All proteins were labeled with the amino reactive reagent Sulfo-NHS-LC biotin.

Example 2: Selection of Toxin Binding Human Monoclonal Antibodies

Toxin binding antibodies were selected by yeast surface display libraries developed according to WO2009/036379A2, WO2012009568 and WO2010105256. Toxin molecules were expressed as recombinant *E. coli* produced proteins and labeled with biotin. All toxins were tested for high purity and integrity, and also for functionality in in vitro assays and in vivo by toxin challenge of mice as described in Example 3.

A library of yeast cells engineered to express full length human IgG1 antibodies with an approx. $10^{9-10}$ diversity were incubated with biotin labeled toxins at different concentrations. Yeast cells expressing antibodies with the capacity of binding to the toxins were isolated by magnetic bead selection and fluorescence-activated cell sorting (FACS) employing streptavidin secondary reagents in several successive (up to five) selection rounds. Antibodies were then produced by the selected yeast clones and purified by Protein A affinity chromatography. Binding of individual, soluble mAbs to the different toxins was confirmed by interferometry measurements using a ForteBio Octet Red instrument [Pall Life Sciences]; the biotinylated antigen or the antibody was immobilized on the sensor and the association and dissociation of the antibody Fab fragment or of the antigen, respectively (typically 200 nM), in solution, were measured. The affinities (Kd values) were calculated based on the measured kinetic parameters (kon and koff)

Example 3: Identification of Human mAbs Able to Neutralize Multiple Staphylococcal Exotoxins First, 12 Hla binding mAbs with unique CDR sequences were tested for Hla neutralization in two different in vitro assays using either rabbit red blood cells or the human lung epithelial cell line A549. For the toxin inhibition assay with human lung epithelial cells (A549, HPACC #86012804), cells were trypsinized and plated on the preceding day at a density of 20,000 cells per well (96-well half area luminescence plates, Greiner, Austria) in F12K medium (Gibco, USA) supplemented with 10% FCS and Pen/Strep. Antibodies were serially diluted in F12K medium supplemented with 5% FCS and Pen/Strep (=A549 cell assay medium) in a separate dilution plate and mixed with alpha hemolysin (Ha) purified from bacterial culture supernatant at a fixed concentration [3.03 nM]. After a 1 hour pre-incubation step at room temperature, seeding medium on adherent A549 cells was discarded and replaced by the mAb-toxin mixture. Cells were intoxicated for 6 hours at 37° C. +5% C02 and viability was then measured using a commercially available kit (Cell Titer-Glo® Luminescent Cell Viability Assay; Promega, USA) according to the manufacturer's instructions. % viability was calculated relative to mock-treated controls. % inhibition of toxin activity was calculated using the following formula: % inhibition=[(viability toxin only–inhibited activity)/(viability toxin only)]×100.

For rabbit red blood cell hemolysis inhibition, rabbit EDTA-whole blood was obtained from New Zealand White Rabbits (Preclinics GmbH, Germany). Blood was diluted 1:1 with PBS w/o Ca/Mg (PAA Laboratories, Austria) and gradients were prepared by layering 15 ml diluted blood on 15 ml LSM 1077 (PAA Laboratories, Austria) in 50 ml polypropylene tubes. Following centrifugation at 680×g (RT, no brakes) platelets, plasma, PBMCs and Ficoll were removed by aspiration and discarded. The remaining RBC pellet was washed twice in 40 ml PBS w/o Ca/Mg (centrifugation 680×g, RT, no brakes) and finally resuspended in 20 ml PBS w/o Ca/Mg. Integrity and cell number of erythrocytes were determined in a standard hemocytometer. For neutralization assays with monoclonal antibodies, antibodies were serially diluted in PBS and mixed with alpha hemolysin at a fixed concentration [12.12 nM]. Hemolysis assay was started after a 1 hour pre-incubation step to allow antibody-toxin binding. 5×10E7 rabbit red blood cells diluted in PBS w/o Ca/Mg were added per well. % inhibition of toxin activity was calculated using the following formula: % inhibition=[(hemolysis toxin only–inhibited activity)/(hemolysis toxin only)]×100.

7 of the 12 mAbs displayed neutralizing activity in the tested concentrations, ranging from highly potent to weakly neutralizing ones (FIG. 2). These 7 antibodies had affinities ranging from Kd=9→300 nM (measured by ForteBio [Pall Life Sciences]) and neutralization potency strongly correlated with affinity.

The CDR sequences of these 7 mAbs were used for generating a first series of affinity maturation libraries that were interrogated again with Hla (lower concentration then used for naïve library selection) to select higher affinity offspring antibodies. The highest affinity offspring from each lineage was further affinity matured by a second series of affinity maturation. The resulting 42 mAbs from the 7 lineages had up to 10,000 fold increased affinity and neutralization potency. Many mAbs reached the limit of affinity measurement even with a highly sensitive MSD method using a Sector Imager 2400 instrument (Meso Scale Discovery). Typically 20 pM of biotinylated antigen was incubated with Fab or IgG, at various concentrations, for 16 h at room temperature, and the unbound antigen captured on immobilized IgG; a plot of unbound antigen versus Fab or IgG concentration gives the dissociation constant, Kd.] (Kd 4 pM, FIG. 3), and most of them also reached the theoretical limit of the in vitro neutralization assays with IC50 of 0.25 expressed as mAb to toxin ratio (1:4) (FIG. 4).

Example 4: Assay to Determine the Cross-Neutralization Potency of Hla Toxin Selected mAbs Testing of the 42 Hla mAbs from the seven lineages for cross-reactivity with bi-component toxins revealed one single offspring derived from the weakest neutralizing naïve clone that displayed picomolar binding affinities to Hla, HlgB and LukF, and single digit nM for LukD. (FIG. 5). Binding to these distantly related toxins resulted in highly potent neutralization of the corresponding bi-component toxins HlgB-HlgC, HlgB-HlgA, LukSF (PVL) and LukED (FIG. 6).

The very same broadly cross-neutralizing mAb (#AB-24) was identified from the yeast libraries with alternating screening with Hla and F-components.

The neutralizing potential of the #7667 lineage against Hla was determined on A549 cells (FIG. 6A) and on rabbit red blood cells as described in Example 3. All mAbs of this lineage were able to inhibit alpha hemolysin activity. Potency correlated well with the maturation status. While the weakest neutralizing activity was observed with naive clone #7667, strongest protection was seen with clones #9024, #AB-24, #9029 and #9030, which generated using a second series of affinity maturation libraries. The mAb #8268 clone, generated by maturation employing the first affinity maturation library, exhibited intermediate neutralizing activity.

The cross-neutralizing activity against the bicomponent toxins LukE-LukD, HlgB-HlgC and LukS-LukF was assessed in a viability assay with human neutrophils (FIG. 6 B-C). For this purpose neutrophils were isolated from fresh human whole blood, either obtained from the Red Cross (heparinized) or obtained by venipuncture from normal healthy volunteers in K-EDTA vacutainer tubes (BD, USA). To aggregate erythrocytes 1 part HetaSep solution (Stem Cell Technologies, France) was added to 5 parts of blood, mixed and incubated at 37° C. until the plasma/erythrocyte interphase was at approximately 50% of the total volume. The leukocyte enriched plasma layer was carefully layered on a 2-step Percoll gradient (73% and 63% Percoll Plus diluted in HBSS, GE Healthcare) and centrifuged at 680×g, RT, 30 min, no brakes. The first and second layer of the post-spin gradient (mainly serum and monocytes) was removed by aspiration. Neutrophils were harvested from the second opaque layer and washed twice in 50 ml HBSS (Gibco, USA)+10 mM Glucose. The number of viable cells was counted using trypan blue dye exclusion in a hemocytometer. The described isolation method usually yielded 1-5×10E8 neutrophils with a viability ≥95% out of 50 ml whole blood. For viability assays, cells were re-suspended in RPMI 1640 (PAA Laboratories, Austria) supplemented with 10% FCS, L-Glutamine and Pen/Strep (=neutrophil medium). Monoclonal antibodies were serially diluted in neutrophil medium and mixed with toxins at a fixed concentration that decreased cell viability ≥95% [2.94 nM for LukS-LukF and HlgC-HlgB, 7.35 nM for LukE-LukD]. Viability assay was started after a 1 hour pre-incubation step to allow antibody-toxin binding. 25,000 cells were added per well and the reaction was incubated for 4 hours at 37° C., +5% $CO_2$. Viability of PMNs was then examined using a commercially available kit (Cell Titer-Glo® Luminescent Cell Viability Assay; Promega, USA) according to the manufacturer's instructions. % viability was calculated relative to mock-treated controls. % inhibition of toxin activity was calculated using the following formula: % inhibition= [(viability toxin only−inhibited activity)/(viability toxin only)]×100. The following controls mAbs were included: #8247 (HIa monospecific mAb from another lineage (#7660)), #8207 (monospecific LukD mAb in LukE-LukD assay), #8210 (monospecific LukF mAb in LukS-LukF assay), #8182 (monospecific HlgB mAb in HlgC-HlgB assay) and #7335 (negative control mAb generated against hen egg lysozyme in all assays).

Although the naïve mAb #7667 and the offspring mAb #8268, generated by maturation using the first affinity maturation library, did not show detectable neutralizing activity against any of the cognate bicomponent toxins, the corresponding offspring mAb #AB-24, generated by maturation using the second affinity maturation library, was found to be a potent inhibitor of LukE-LukD, HlgC-HlgB and LukS-LukF on human neutrophils (FIG. 6 B-C). Although comparable in HIa neutralizing activity, the other matured mAbs of the same lineage that were matured using the second affinity maturation library were not able to cross-neutralize all three bi-component toxins in this assay. However, #9029 was found to have comparable potency than #AB-24 in LukE-LukD neutralization. The results of the in vitro neutralization assays were in line with the ForteBio kD measurements, where #AB-24 exhibited binding to HIa×HlgB× LukD×LukF, and #9029 was found to be a HIa×LukD binder.

Example 5: Assay to Determine Biological Activity

In vitro potency was proved to be predictive for in vivo efficacy. Treatment of mice with the #AB-24 mAbs protected very well against lethal challenge with HIa or HlgAB toxins (FIG. 7). In vivo cross-neutralizing potential of mAb #AB-24 was tested in various mouse models. In pilot studies the minimal lethal concentration of the purified toxins of interest was determined by administration of serial dilutions and subsequently monitoring survival for 14 days. In case of intranasal instillation of HIa, the minimal lethal dose was found to be 0.32 µg/mouse. Following intravenous injection of various doses of HlgAB, a minimal lethal dose of 0.375 µg (of both components) was determined.

Based on these results, in challenge experiments aiming to test protective capacity of passive immunization by mAbs the following challenge doses were used: 0.4 µg for HIa applied intranasally, and 0.5 µg for each components of HlgAB administered intravenously.

Passive immunization with mAb #AB-24 was performed intraperitoneally either 4 h (HIa challenge) or 24 h (HlgAB challenge) prior to the lethal challenge by toxins. Groups of 5 mice received various doses of the individual mAbs dissolved in PBS. Control groups received either PBS alone or the highest dose of isotype matched non-specific mAb. Following challenge with the purified toxins, lethality of mice was monitored daily for 7 days.

In FIG. 7 the outcome of the HIa challenge experiment is depicted. LI control mice succumbed to toxin challenge within 24 h, whereas mAb #AB-24 provided significant protection repeatedly at the 100 µg mAb/mouse dose (60-100%). The very same antibody also protected mice from lethal HlgAB challenge and rescued 80% and 40% of mice at 200 and 50 µg/mouse doses, respectively.

These experiments proved the cross-protective potential of #AB-24 for two of the two most important staphylococcal cytotoxin that are are structuraly related, however, only very distantly at the primary amino acid sequence level (27% amino acid identity).

Example 6: Assay to Determine Competition of HIa mAbs

Competition between the HIa mAbs was studied by interferometry (Forte-Bio). In a typical set-up, HIa [5 µg/ml in buffer (PBS plus 0.1% BSA)] was immobilized onto Streptavidin sensors (Pall Life Sciences). The sensors were then treated with the primary antibody (or buffer only), followed by the secondary antibody (10 µg/ml each), typically for 10 min each; (the buffer only condition gave the response corresponding to 100% binding of the secondary antibody to HIa). The percentage inhibition of secondary antibody binding was calculated, for each primary antibody (FIG. 8).

For the three antibodies shown in FIG. 8, the self-inhibition varied from 81 to 91%, while the inhibition between different antibodies varied from 30 to 76%. For the purpose of a fine differentiation between antibodies, and based on data with additional HIa antibodies, an inhibition limit of 80% was set in this study. Hence it was considered that any antibody that is able to inhibit binding of the second antibody by 80% is competing with the said secondary antibody, whereas if the inhibition falls below 80%, the antibodies are not sufficiently competitive.

The invention claimed is:

1. A recombinant monoclonal cross-neutralizing antibody composition comprising at least one polyspecific binding site that binds to alpha-toxin (Hla) and at least one of a bi-component toxin of *Staphylococcus aureus* wherein the antibody has an affinity to bind each of said Hla and said at least one of a bi-component toxin with a Kd of less than $10^{-9}$M.

2. The recombinant monoclonal cross-neutralizing antibody composition according to claim 1, wherein said bi-component toxin of *Staphylococcus aureus* is selected from the group consisting of cognate and non-cognate pairs of F and S components of gamma-hemolysins, PVL toxins and PVL-like toxins, HlgAB, HlgCB, LukSF, LukED, LukGH, LukS-HlgB, LukSD, HlgA-LukD, HlgA-LukF, LukG-HlgA, LukEF, LukE-HlgB, HlgC-LukD and HlgC-LukF.

3. The recombinant monoclonal cross-neutralizing antibody composition according to claim 1, wherein said binding site binds to at least two or at least three bi-component toxins selected from the group consisting of HlgAB, HlgCB, LukSF and LukED.

4. The recombinant monoclonal cross-neutralizing antibody composition according to claim 1, wherein said binding site is a CDR binding site comprising CDR sequences of a VH and/or a VL binding site.

5. The recombinant monoclonal cross-neutralizing antibody composition according to claim 1, which is a full-length monoclonal antibody or an antibody fragment thereof comprising at least one antibody domain incorporating the binding site which has an affinity to bind each of the toxins with a Kd of less than $10^{-9}$M.

6. The recombinant monoclonal cross-neutralizing antibody composition according to claim 1, wherein the antibody binds the same epitope as an antibody designated #AB-24.

7. The recombinant monoclonal cross-neutralizing antibody composition according to claim 1, wherein the cross-neutralizing antibody comprises a light chain and a heavy chain, and wherein the light chain is #AB-24-LC and/or the heavy chain is #AB-24-HC, wherein #AB-24-LC is the same as comprised in a host cell deposited under DSM 26748; and #AB-24-HC is the same as comprised in a host cell deposited under DSM 26747, or a functionally active variant of any of #AB-24-LC or #AB-24-HC.

8. A plasmid comprising a nucleotide sequence encoding the recombinant cross-neutralizing antibody of claim 1.

9. An expression cassette comprising the nucleotide sequence encoding the recombinant cross-neutralizing antibody according to claim 8.

10. A host cell comprising the expression cassette according to claim 9.

11. A method of producing an antibody comprising an antibody light chain designated #AB-24-LC comprised in a host cell deposited under DSM 26748 and/or an antibody heavy chain designated #AB-24-HC comprised in a host cell deposited under DSM 26747, wherein the method comprises cultivating or maintaining a host cell comprising a plasmid comprising a nucleotide sequence
   encoding the antibody light chain designated #AB-24-LC comprised in the host cell deposited under DSM 26748; and/or
   encoding the antibody heavy chain designated #AB-24-HC comprised in the host cell deposited under DSM 26747 under conditions to produce said antibody.

12. A method of identifying a candidate antibody comprising:
   (a) providing a sample containing a sample antibody or a cell producing the sample antibody; and
   (b) assessing for binding of the sample antibody with an epitope recognized by an antibody comprising an antibody light chain designated #AB-24-LC comprised in a host cell deposited under DSM 26748; and/or an antibody heavy chain designated #AB-24-HC comprised in a host cell deposited under DSM 26747, wherein a positive reaction between the sample antibody and the epitope identifies the sample antibody as the candidate-antibody.

13. A method of identifying a candidate antibody comprising:
   (a) providing a sample containing a sample antibody or a cell producing the sample antibody; and
   (b) assessing for binding of the sample antibody with alpha-toxin and at least one of a bi-component toxin of *Staphylococcus aureus*, wherein a positive reaction between the sample antibody and the toxins identifies the sample antibody as the candidate antibody.

14. A method of producing a monoclonal antibody, comprising
   (a) providing the candidate antibody identified according to claim 12; and
   (b) producing the monoclonal antibody, or a humanized or human form of the candidate antibody, or a functionally active derivative thereof with a same epitope binding specificity as the candidate antibody.

15. A method of therapeutically treating a subject suffering from a *S. aureus* infection comprising administering to the subject an effective amount of a recombinant cross-neutralizing antibody comprising at least one polyspecific binding site that binds to alpha-toxin (Hla) and at least one of a bi-component toxin of *Staphylococcus aureus* to limit the infection in the subject, to therapeutically treat a disease condition resulting from said infection or to inhibit *S. aureus* pneumonia pathogenesis.

16. A pharmaceutical preparation, comprising the recombinant monoclonal cross-neutralizing antibody composition according to claim 1 and a pharmaceutically acceptable carrier or excipient.

17. A method of diagnosing an *S. aureus* infection in a subject, comprising
   1) obtaining a result of contacting a sample obtained from the subject with a recombinant cross-neutralizing antibody comprising at least one polyspecific binding site that binds to alpha-toxin (Hla) and at least one of a bi-component toxin of *Staphylococcus aureus*, wherein binding of the antibody to a material in the sample indicates the infection, and
   2) advising the subject of the result,
   wherein the *S. aureus* infection includes any of high toxin producing MRSA infections, necrotizing pneumonia, and/or toxin production in furunculosis and carbunculosis.

18. A diagnostic preparation of the recombinant cross-neutralizing antibody according to claim 1, comprising the antibody with a label.

19. An immunogen comprising:
   (a) a conformational epitope recognized by an antibody comprising an antibody light chain designated #AB-24-LC comprised in a host cell deposited under DSM 26748; and/or an antibody heavy chain designated #AB-24-HC comprised in a host cell deposited under DSM 26747;
   (b) further one or more additional *S. aureus* epitopes; and
   (c) a carrier.

20. A method of treating a subject comprising administering an effective amount of an immunogen comprising (a) an isolated conformational epitope recognized by an antibody comprising an antibody light chain designated #AB-24-LC comprised in a host cell deposited under DSM 26748; and/or an antibody heavy chain designated #AB-24-HC comprised in a host cell deposited under DSM 26747; (b) optionally further one or more additional *S. aureus* epitopes; and
   (c) a carrier, wherein the treatment protects the subject from an *S. aureus* infection, prevents a disease condition resulting from said infection or inhibits *S. aureus* pneumonia pathogenesis.

21. An isolated nucleic acid encoding the recombinant cross-neutralizing antibody according to claim 1.

* * * * *

SEQUENCE LISTING

```
<160> NUMBER OF SEQ ID NOS: 28

<210> SEQ ID NO 1
<211> LENGTH: 879
<212> TYPE: DNA
<213> ORGANISM: Staphylococcus aureus

<400> SEQUENCE: 1
gccgacagcg acatcaacat caaaacgggc acgacggaca ttggctcaaa tacgacggtg      60
aaaacgggcg atctggttac ctatgacaaa gaaaacggca tgcataaaaa agtgttttat     120
agtttcatcg atgacaaaaa ccacaacaaa aaactgctgg tcattcgtac caaaggcacg     180
atcgcaggcc agtatcgcgt gtacagcgaa gaaggcgcta ataaatcagg tctggcatgg     240
```

```
ccgtcggctt taaagttca gctgcaactg ccggataacg aagtcgcgca aattagcgac    300
tattacccgc gtaactctat cgataccaaa gaatacatgt ctaccctgac gtacggcttc    360
aacggtaatg ttaccggcga tgacacgggt aaaattggcg gtctgatcgg cgccaacgtg    420
agcattggtc atacccctgaa atatgttcag ccggacttta aaaccatcct ggaatctccg    480
acggataaaa agtgggctg aaagttatc ttcaacaaca tggttaacca gaactggggt    540
ccgtatgatc gtgactcatg gaacccggtc tacggcaatc aactgtttat gaaaacccgc    600
aacggttcga tgaaagcggc cgataacttc ctggacccga taaagcgag ctctctgctg    660 agttccggct ttagtccgga cttcgcgacc gtgattacga tggatcgcaa agcctccaaa    720
cagcaaacca atattgatgt catctatgaa cgtgtgcgcg atgactacca gctgcactgg    780
accagcacga actggaaagg taccaatacg aaagataaat ggattgaccg ctcctcggaa    840
cgctacaaaa ttgactggga aaagaagaa atgacgaac                             879

<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255
```

```
Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290

<210> SEQ ID NO 3
<211> LENGTH: 852
<212> TYPE: DNA
<213> ORGANISM: Staphylococcus aureus

<400> SEQUENCE: 3
gacaacaaca ttgaaaacat tggtgatggc gcagaagtgg tgaaacgcac ggaagatacc      60
tcaagcgata aatggggtgt gacgcagaac attcagttcg atttcgtcaa agacaaaaaa     120
tacaacaaag atgcactgat tctgaaaatg caaggcttta tcaacagcaa aaccacgtac     180
tacaactaca aaaacaccga ccatatcaaa gctatgcgtt ggccgttcca gtacaatatc     240
ggtctgaaaa cgaacgatcc gaatgttgac ctgatcaact acctgccgaa aaacaaaatc     300
gattcagtga acgtttcgca aaccctgggc tacaatatcg gcggtaactt taatagtggc     360
ccgtccaccg gcggtaacgg tagcttcaac tactctaaaa cgatcagtta caaccagcaa     420
aactacatct ctgaagtcga acgtcagaac agcaaatctg tgcaatgggg cattaaagcg     480
aattccttta tcacctcact gggcaaaatg tcgggtcatg atccgaacct gtttgtgggt     540
tataaaccgt acagccagaa cccgcgcgat tatttcgttc cggacaatga actgccgccg     600
ctggtccatt ctggctttaa cccgagtttc attgcaaccg tgagccacga aaaaggctcg     660
ggtgatacca gcgaatttga aatcacgtat ggtcgcaata tggacgttac ccatgcgacg     720
cgtcgcacca cgcactatgg caactcctac ctggaaggtt cacgtattca atgccttc      780 gttaaccgca attacacggt gaaatacgaa gtcaactgga aaacgcacga atcaaagtg     840 aaaggtcata ac                                                         852

<210> SEQ ID NO 4
<211> LENGTH: 284
<212> TYPE: PRT
<213> ORGANISM: Staphylococcus aureus

<400> SEQUENCE: 4

Asp Asn Asn Ile Glu Asn Ile Gly Asp Gly Ala Glu Val Val Lys Arg
1               5                   10                  15

Thr Glu Asp Thr Ser Ser Asp Lys Trp Gly Val Thr Gln Asn Ile Gln
            20                  25                  30

Phe Asp Phe Val Lys Asp Lys Lys Tyr Asn Lys Asp Ala Leu Ile Leu
        35                  40                  45

Lys Met Gln Gly Phe Ile Asn Ser Lys Thr Thr Tyr Tyr Asn Tyr Lys
    50                  55                  60

Asn Thr Asp His Ile Lys Ala Met Arg Trp Pro Phe Gln Tyr Asn Ile
65                  70                  75                  80

Gly Leu Lys Thr Asn Asp Pro Asn Val Asp Leu Ile Asn Tyr Leu Pro
                85                  90                  95

Lys Asn Lys Ile Asp Ser Val Asn Val Ser Gln Thr Leu Gly Tyr Asn
            100                 105                 110

Ile Gly Gly Asn Phe Asn Ser Gly Pro Ser Thr Gly Gly Asn Gly Ser
        115                 120                 125
```

Phe Asn Tyr Ser Lys Thr Ile Ser Tyr Asn Gln Gln Asn Tyr Ile Ser
            130                 135                 140
Glu Val Glu Arg Gln Asn Ser Lys Ser Val Gln Trp Gly Ile Lys Ala
145                 150                 155                 160
Asn Ser Phe Ile Thr Ser Leu Gly Lys Met Ser Gly His Asp Pro Asn
                165                 170                 175
Leu Phe Val Gly Tyr Lys Pro Tyr Ser Gln Asn Pro Arg Asp Tyr Phe
            180                 185                 190
Val Pro Asp Asn Glu Leu Pro Pro Leu Val His Ser Gly Phe Asn Pro
        195                 200                 205
Ser Phe Ile Ala Thr Val Ser His Glu Lys Gly Ser Gly Asp Thr Ser
210                 215                 220
Glu Phe Glu Ile Thr Tyr Gly Arg Asn Met Asp Val Thr His Ala Thr
225                 230                 235                 240
Arg Arg Thr Thr His Tyr Gly Asn Ser Tyr Leu Glu Gly Ser Arg Ile
                245                 250                 255
His Asn Ala Phe Val Asn Arg Asn Tyr Thr Val Lys Tyr Glu Val Asn
            260                 265                 270
Trp Lys Thr His Glu Ile Lys Val Lys Gly His Asn
            275                 280

<210> SEQ ID NO 5
<211> LENGTH: 903
<212> TYPE: DNA
<213> ORGANISM: Staphylococcus aureus

<400> SEQUENCE: 5
gcgcagcaca tcacgccggt ctccgaaaaa aagttgacg acaaaatcac cctgtataaa      60
acgacggcca cgagcgactc tgacaaactg aaaatttctc agatcctgac cttcaacttc     120
atcaaagata aagttacga taaagacacg ctgattctga agcggccgg taacatctat      180
tctggctaca ccaaaccgaa tccgaaagac acgatcagct ctcaattcta ctggggttcc    240
aaatacaaca tctcaatcaa cagtgattcc aacgactccg tcaatgtggt tgattatgca    300
ccgaaaaacc agaatgaaga attccaagtc cagcaaaccg tgggctatag ttacggcggt    360
gacattaaca tctcgaatgg tctgagcggc ggtggcaacg gctcaaaatc gttcagcgaa    420
acgatcaact acaaacagga tcttaccgt accagtctgg ataaacgcac gaatttcaag    480
aaaattggtt gggacgttga agcgcataaa atcatgaaca tggttgggg cccgtatggc    540
cgtgattctt atcacagtac ctacggtaac gaaatgtttc tgggctcccg ccagtcaaac    600
ctgaatgccg gtcaaaattt cctggaatac cataaaatgc cggttctgag ccgtggtaac    660
tttaatccgg aattcattgg cgtcctgtcg cgcaaacaga acgcagcgaa aaaatctaaa    720
atcaccgtga cgtatcagcg tgaaatggat cgctacacca acttttggaa tcaactgcat    780
tggatcggca caactacaa agatgaaaac cgtgccaccc acacgagcat ctacgaagtt    840
gactgggaaa accacacggt gaaactgatt gatacccaaa gtaaagaaaa aaacccgatg    900
tcg                                                                  903

<210> SEQ ID NO 6
<211> LENGTH: 301
<212> TYPE: PRT
<213> ORGANISM: Staphylococcus aureus

<400> SEQUENCE: 6

Ala Gln His Ile Thr Pro Val Ser Glu Lys Lys Val Asp Asp Lys Ile

```
              1               5                  10                 15
            Thr Leu Tyr Lys Thr Thr Ala Thr Ser Asp Ser Asp Lys Leu Lys Ile
                           20                  25                  30

Ser Gln Ile Leu Thr Phe Asn Phe Ile Lys Asp Lys Ser Tyr Asp Lys
                           35                  40                  45

Asp Thr Leu Ile Leu Lys Ala Gly Asn Ile Tyr Ser Gly Tyr Thr
                        50                  55                  60

Lys Pro Asn Pro Lys Asp Thr Ile Ser Ser Gln Phe Tyr Trp Gly Ser
             65                 70                  75                  80

Lys Tyr Asn Ile Ser Ile Asn Ser Asp Ser Asn Asp Ser Val Asn Val
                               85                  90                  95

Val Asp Tyr Ala Pro Lys Asn Gln Asn Glu Glu Phe Gln Val Gln Gln
                          100                 105                 110

Thr Val Gly Tyr Ser Tyr Gly Gly Asp Ile Asn Ile Ser Asn Gly Leu
                          115                 120                 125

Ser Gly Gly Gly Asn Gly Ser Lys Ser Phe Ser Glu Thr Ile Asn Tyr
                       130                 135                 140

Lys Gln Glu Ser Tyr Arg Thr Ser Leu Asp Lys Arg Thr Asn Phe Lys
            145                 150                 155                 160

Lys Ile Gly Trp Asp Val Glu Ala His Lys Ile Met Asn Asn Gly Trp
                            165                 170                 175

Gly Pro Tyr Gly Arg Asp Ser Tyr His Ser Thr Tyr Gly Asn Glu Met
                        180                 185                 190

Phe Leu Gly Ser Arg Gln Ser Asn Leu Asn Ala Gly Gln Asn Phe Leu
                        195                 200                 205

Glu Tyr His Lys Met Pro Val Leu Ser Arg Gly Asn Phe Asn Pro Glu
                    210                 215                 220

Phe Ile Gly Val Leu Ser Arg Lys Gln Asn Ala Ala Lys Lys Ser Lys
            225                 230                 235                 240

Ile Thr Val Thr Tyr Gln Arg Glu Met Asp Arg Tyr Thr Asn Phe Trp
                            245                 250                 255

Asn Gln Leu His Trp Ile Gly Asn Asn Tyr Lys Asp Glu Asn Arg Ala
                        260                 265                 270

Thr His Thr Ser Ile Tyr Glu Val Asp Trp Glu Asn His Thr Val Lys
                        275                 280                 285

Leu Ile Asp Thr Gln Ser Lys Glu Lys Asn Pro Met Ser
                    290                 295                 300

<210> SEQ ID NO 7
<211> LENGTH: 849
<212> TYPE: DNA
<213> ORGANISM: Staphylococcus aureus

<400> SEQUENCE: 7
aatacgaata tcgaaaatat cggcgacggc gcagaagtta tcaaacgcac ggaagatgtc      60
agcagcaaaa aatggggtgt tacgcagaat gttcagttcg atttcgtcaa agacaaaaaa     120
tacaacaaag atgcactgat tgtgaaaatg caaggcttta tcaattctcg taccagtttc     180
tccgacgtta aaggcagtgg ttatgaactg acgaaacgca tgatttggcc gtttcagtac     240
aacatcggtc tgaccacgaa agatccgaac gtttccctga tcaactacct gccgaaaaac     300
aaaatcgaaa ccacggacgt cggccagacc ctgggttaca acattggcgg taattttcaa     360
agcgctccgt ctatcggcgg taacggctca ttcaattact cgaaaaccat tagctatacg     420
cagaaaagtt acgtgtccga agttgataaa caaaactcaa aatcggtcaa atggggcgtg     480
```

```
aaagcgaacg aatttgtcac cccggatggt aaaaaatctg cccatgaccg ttacctgttt    540
gtgcagtcgc cgaatggtcc gacgggtagc gcacgtgaat actttgcccc ggataatcag    600
ctgccgccgc tggtgcaatc tggctttaac ccgagtttca ttaccacgct gagccatgaa    660
aaaggcagct ctgatacctc cgaattcgaa atttcatatg gtcgtaatct ggacatcacc    720
tacgcaacgc tgtttccgcg taccggtatc tatgcagaac gcaaacacaa cgcttttgtt    780
aaccgcaatt tcgttgtccg ctacgaagtg aactggaaaa cccatgaaat caaagtgaaa    840
ggccataac                                                             849
```

<210> SEQ ID NO 8
<211> LENGTH: 283
<212> TYPE: PRT
<213> ORGANISM: Staphylococcus aureus

<400> SEQUENCE: 8

```
Asn Thr Asn Ile Glu Asn Ile Gly Asp Gly Ala Glu Val Ile Lys Arg
1               5                   10                  15

Thr Glu Asp Val Ser Ser Lys Lys Trp Gly Val Thr Gln Asn Val Gln
            20                  25                  30

Phe Asp Phe Val Lys Asp Lys Lys Tyr Asn Lys Asp Ala Leu Ile Val
        35                  40                  45

Lys Met Gln Gly Phe Ile Asn Ser Arg Thr Ser Phe Ser Asp Val Lys
    50                  55                  60

Gly Ser Gly Tyr Glu Leu Thr Lys Arg Met Ile Trp Pro Phe Gln Tyr
65                  70                  75                  80

Asn Ile Gly Leu Thr Thr Lys Asp Pro Asn Val Ser Leu Ile Asn Tyr
                85                  90                  95

Leu Pro Lys Asn Lys Ile Glu Thr Thr Asp Val Gly Gln Thr Leu Gly
            100                 105                 110

Tyr Asn Ile Gly Gly Asn Phe Gln Ser Ala Pro Ser Ile Gly Gly Asn
        115                 120                 125

Gly Ser Phe Asn Tyr Ser Lys Thr Ile Ser Tyr Thr Gln Lys Ser Tyr
    130                 135                 140

Val Ser Glu Val Asp Lys Gln Asn Ser Lys Ser Val Lys Trp Gly Val
145                 150                 155                 160

Lys Ala Asn Glu Phe Val Thr Pro Asp Gly Lys Lys Ser Ala His Asp
                165                 170                 175

Arg Tyr Leu Phe Val Gln Ser Pro Asn Gly Pro Thr Gly Ser Ala Arg
            180                 185                 190

Glu Tyr Phe Ala Pro Asp Asn Gln Leu Pro Pro Leu Val Gln Ser Gly
        195                 200                 205

Phe Asn Pro Ser Phe Ile Thr Thr Leu Ser His Glu Lys Gly Ser Ser
    210                 215                 220

Asp Thr Ser Glu Phe Glu Ile Ser Tyr Gly Arg Asn Leu Asp Ile Thr
225                 230                 235                 240

Tyr Ala Thr Leu Phe Pro Arg Thr Gly Ile Tyr Ala Glu Arg Lys His
                245                 250                 255

Asn Ala Phe Val Asn Arg Asn Phe Val Val Arg Tyr Glu Val Asn Trp
            260                 265                 270

Lys Thr His Glu Ile Lys Val Lys Gly His Asn
        275                 280
```

<210> SEQ ID NO 9

<211> LENGTH: 903
<212> TYPE: DNA
<213> ORGANISM: Staphylococcus aureus

<400> SEQUENCE: 9

```
gcccaacaca ttacgccggt ctcggaaaaa aaagtggatg acaaaatcac gctgtataaa    60
acgacggcaa cctcagataa cgacaaactg aacattagtc agatcctgac cttcaacttc   120
atcaaagata atcctacga taaagacacg ctggtgctga agcggccgg caacattaat    180
tcaggttaca aaaaaccgaa cccgaaagac tataattact cgcagtttta ttggggcggt   240
aaatacaacg tcagcgtgag ctctgaatct aacgatgcag tcaatgtggt tgactatgct   300
ccgaaaaacc agaatgaaga atttcaagtg cagcaaaccc tgggctatag ctacggcggt   360
gatattaaca tctcaaatgg cctgtcgggc ggtctgaacg gttcgaaaag cttctctgaa   420
accatcaact acaaacagga aagctaccgt accacgattg atcgcaaaac gaaccataaa   480
tctatcggct ggggtgttga agcgcacaaa attatgaaca atggctgggg tccgtatggc   540
cgtgattcct atgacccgac ctacggtaat gaactgtttc tgggcggtcg ccagagttcc   600
tcaaacgcgg gccaaaattt cctgccgacg catcagatgc cgctgctggc acgtggtaac   660
tttaatccgg aattcatcag tgtgctgtcc cacaaacaaa acgataccaa aaaatctaaa   720
atcaaagtta cgtatcaacg tgaaatggac cgctacacca ccagtggaa tcgcctgcat   780
tgggttggta caactacaa aaccagaac accgttacgt tcacctctac gtacgaagtc   840
gattggcaaa accatacggt caaactgatt ggcacggaca gcaagaaac gaacccgggc   900
gtc                                                                903
```

<210> SEQ ID NO 10
<211> LENGTH: 301
<212> TYPE: PRT
<213> ORGANISM: Staphylococcus aureus

<400> SEQUENCE: 10

```
Ala Gln His Ile Thr Pro Val Ser Glu Lys Lys Val Asp Asp Lys Ile
1               5                   10                  15

Thr Leu Tyr Lys Thr Thr Ala Thr Ser Asp Asn Asp Lys Leu Asn Ile
            20                  25                  30

Ser Gln Ile Leu Thr Phe Asn Phe Ile Lys Asp Lys Ser Tyr Asp Lys
        35                  40                  45

Asp Thr Leu Val Leu Lys Ala Ala Gly Asn Ile Asn Ser Gly Tyr Lys
    50                  55                  60

Lys Pro Asn Pro Lys Asp Tyr Asn Tyr Ser Gln Phe Tyr Trp Gly
65                  70                  75                  80

Lys Tyr Asn Val Ser Val Ser Ser Glu Ser Asn Asp Ala Val Asn Val
                85                  90                  95

Val Asp Tyr Ala Pro Lys Asn Gln Asn Glu Glu Phe Gln Val Gln Gln
            100                 105                 110

Thr Leu Gly Tyr Ser Tyr Gly Gly Asp Ile Asn Ile Ser Asn Gly Leu
        115                 120                 125

Ser Gly Gly Leu Asn Gly Ser Lys Ser Phe Ser Glu Thr Ile Asn Tyr
    130                 135                 140

Lys Gln Glu Ser Tyr Arg Thr Thr Ile Asp Arg Lys Thr Asn His Lys
145                 150                 155                 160

Ser Ile Gly Trp Gly Val Glu Ala His Lys Ile Met Asn Asn Gly Trp
                165                 170                 175
```

Gly Pro Tyr Gly Arg Asp Ser Tyr Asp Pro Thr Tyr Gly Asn Glu Leu
            180                 185                 190

Phe Leu Gly Gly Arg Gln Ser Ser Ser Asn Ala Gly Gln Asn Phe Leu
        195                 200                 205

Pro Thr His Gln Met Pro Leu Leu Ala Arg Gly Asn Phe Asn Pro Glu
    210                 215                 220

Phe Ile Ser Val Leu Ser His Lys Gln Asn Asp Thr Lys Lys Ser Lys
225                 230                 235                 240

Ile Lys Val Thr Tyr Gln Arg Glu Met Asp Arg Tyr Thr Asn Gln Trp
                245                 250                 255

Asn Arg Leu His Trp Val Gly Asn Asn Tyr Lys Asn Gln Asn Thr Val
            260                 265                 270

Thr Phe Thr Ser Thr Tyr Glu Val Asp Trp Gln Asn His Thr Val Lys
        275                 280                 285

Leu Ile Gly Thr Asp Ser Lys Glu Thr Asn Pro Gly Val
    290                 295                 300

<210> SEQ ID NO 11
<211> LENGTH: 840
<212> TYPE: DNA
<213> ORGANISM: Staphylococcus aureus

<400> SEQUENCE: 11
gaaaacaaaa tcgaagacat cggccaaggt gctgaaatca tcaaacgcac gcaagacatc    60
acgagtaaac gcctggcaat cacgcagaat attcagttcg atttcgtgaa agacaaaaaa   120
tacaacaaag atgcactggt ggttaaaatg caaggcttta tcagctctcg taccacgtac   180
agcgatctga aaaatatcc gtacattaaa cgcatgatct ggccgttcca gtacaacatc   240
agtctgaaaa ccaagattc caacgtggac ctgattaatt acctgccgaa aaacaaaatc   300
gatagtgcgg acgtttccca gaaactgggc tataacattg gcggtaattt tcaatcagcc   360
ccgtcgatcg gcggtagtgg ttccttcaat tactcaaaaa ccatctcgta caaccagaaa   420
aattacgtta cggaagtcga agccaaaac tctaaaggcg tgaaatgggg tgttaaagcg   480
aattcatttg tcaccccgaa cggccaggtg tcggcgtatg atcagtacct gtttgcacaa   540 gaccccgacgg gtccggcagc acgtgattat ttcgttccgg acaatcagct gccgccgctg   600
attcaaagcg gctttaaccc gtctttcatc accacgctgt cccatgaacg tggcaaaggt   660
gataaaagcg aatttgaaat tacctatggt cgcaacatgg atgcaaccta tgcttacgtt   720
acgcgtcatc gcctggcagt cgatcgtaaa cacgacgctt tcaaaaaccg caatgtcacc   780
gtgaaatacg aagtcaactg gaaaacgcac gaagtcaaaa tcaaatcaat cacccccgaaa   840

<210> SEQ ID NO 12
<211> LENGTH: 280
<212> TYPE: PRT
<213> ORGANISM: Staphylococcus aureus

<400> SEQUENCE: 12

Glu Asn Lys Ile Glu Asp Ile Gly Gln Gly Ala Glu Ile Ile Lys Arg
1               5                   10                  15

Thr Gln Asp Ile Thr Ser Lys Arg Leu Ala Ile Thr Gln Asn Ile Gln
            20                  25                  30

Phe Asp Phe Val Lys Asp Lys Lys Tyr Asn Lys Asp Ala Leu Val Val
        35                  40                  45

Lys Met Gln Gly Phe Ile Ser Ser Arg Thr Thr Tyr Ser Asp Leu Lys
    50                  55                  60

Lys Tyr Pro Tyr Ile Lys Arg Met Ile Trp Pro Phe Gln Tyr Asn Ile
65                  70                  75                  80

Ser Leu Lys Thr Lys Asp Ser Asn Val Asp Leu Ile Asn Tyr Leu Pro
            85                  90                  95

Lys Asn Lys Ile Asp Ser Ala Asp Val Ser Gln Lys Leu Gly Tyr Asn
            100                 105                 110

Ile Gly Gly Asn Phe Gln Ser Ala Pro Ser Ile Gly Gly Ser Gly Ser
            115                 120                 125

Phe Asn Tyr Ser Lys Thr Ile Ser Tyr Asn Gln Lys Asn Tyr Val Thr
130                 135                 140

Glu Val Glu Ser Gln Asn Ser Lys Gly Val Lys Trp Gly Val Lys Ala
145                 150                 155                 160

Asn Ser Phe Val Thr Pro Asn Gly Gln Val Ser Ala Tyr Asp Gln Tyr
                165                 170                 175

Leu Phe Ala Gln Asp Pro Thr Gly Pro Ala Ala Arg Asp Tyr Phe Val
            180                 185                 190

Pro Asp Asn Gln Leu Pro Pro Leu Ile Gln Ser Gly Phe Asn Pro Ser
            195                 200                 205

Phe Ile Thr Thr Leu Ser His Glu Arg Gly Lys Gly Asp Lys Ser Glu
210                 215                 220

Phe Glu Ile Thr Tyr Gly Arg Asn Met Asp Ala Thr Tyr Ala Tyr Val
225                 230                 235                 240

Thr Arg His Arg Leu Ala Val Asp Arg Lys His Asp Ala Phe Lys Asn
                245                 250                 255

Arg Asn Val Thr Val Lys Tyr Glu Val Asn Trp Lys Thr His Glu Val
            260                 265                 270

Lys Ile Lys Ser Ile Thr Pro Lys
            275                 280

<210> SEQ ID NO 13
<211> LENGTH: 858
<212> TYPE: DNA
<213> ORGANISM: Staphylococcus aureus

<400> SEQUENCE: 13
gcaaacgaca cggaagacat cggcaaaggt tcagacatcg aaatcatcaa acgcacggaa      60
gacaaaacga gcaataaatg gggtgtgacc cagaacattc aattcgattt cgtgaaagac     120
aaaaaataca ataaagatgc gctgattctg aaaatgcagg gctttatcag ctctcgtacc     180
acgtactaca actacaagaa aaccaaccat gttaaagcca tgcgctggcc gttccaatac     240
aacatcggtc tgaaaacgaa tgacaaatat gtcagtctga ttaactacct gccgaaaaat     300
aaaatcgaat cgaccaacgt gagccagacg ctgggctata acattggcgg taattttcaa     360
tccgcaccgt cactgggcgg taacggttca ttcaattact caaatcgat cagctatacc     420 cagcaaaact acgtgtctga agttgaacag caaaattcta aaagtgtcct gtggggcgtg     480
aaagcgaata gctttgccac ggaatctggt cagaaaagtg catttgattc cgacctgttc     540
gtgggctata accgcattc aaaagatccg cgtgactact cgtgccgga ttcggaactg     600 ccgccgctgg ttcagtcagg tttttaaccccg tcgttcattg ctaccgttag tcacgaaaaa     660
ggcagttccg ataccteccga atttgaaatt acgtatggtc gtaatatgga cgtcacccat     720
gcaatcaaac gcagcacgca ctatggcaac tcttacctgg atggtcatcg tgttcacaat     780
gcttttgtca accgcaatta tacggtgaaa tacgaagtca actggaaaac gcacgaaatc     840
aaagtcaaag gtcaaaac                                                                858

<210> SEQ ID NO 14
<211> LENGTH: 286
<212> TYPE: PRT
<213> ORGANISM: Staphylococcus aureus

<400> SEQUENCE: 14

```
Ala Asn Asp Thr Glu Asp Ile Gly Lys Gly Ser Asp Ile Glu Ile Ile
1               5                   10                  15

Lys Arg Thr Glu Asp Lys Thr Ser Asn Lys Trp Gly Val Thr Gln Asn
            20                  25                  30

Ile Gln Phe Asp Phe Val Lys Asp Lys Tyr Asn Lys Asp Ala Leu
        35                  40                  45

Ile Leu Lys Met Gln Gly Phe Ile Ser Ser Arg Thr Thr Tyr Tyr Asn
    50                  55                  60

Tyr Lys Lys Thr Asn His Val Lys Ala Met Arg Trp Pro Phe Gln Tyr
65                  70                  75                  80

Asn Ile Gly Leu Lys Thr Asn Asp Lys Tyr Val Ser Leu Ile Asn Tyr
                85                  90                  95

Leu Pro Lys Asn Lys Ile Glu Ser Thr Asn Val Ser Gln Thr Leu Gly
            100                 105                 110

Tyr Asn Ile Gly Gly Asn Phe Gln Ser Ala Pro Ser Leu Gly Gly Asn
        115                 120                 125

Gly Ser Phe Asn Tyr Ser Lys Ser Ile Ser Tyr Thr Gln Gln Asn Tyr
    130                 135                 140

Val Ser Glu Val Glu Gln Asn Ser Lys Ser Val Leu Trp Gly Val
145                 150                 155                 160

Lys Ala Asn Ser Phe Ala Thr Glu Ser Gly Gln Lys Ser Ala Phe Asp
                165                 170                 175

Ser Asp Leu Phe Val Gly Tyr Lys Pro His Ser Lys Asp Pro Arg Asp
            180                 185                 190

Tyr Phe Val Pro Asp Ser Glu Leu Pro Pro Leu Val Gln Ser Gly Phe
        195                 200                 205

Asn Pro Ser Phe Ile Ala Thr Val Ser His Glu Lys Gly Ser Ser Asp
    210                 215                 220

Thr Ser Glu Phe Glu Ile Thr Tyr Gly Arg Asn Met Asp Val Thr His
225                 230                 235                 240

Ala Ile Lys Arg Ser Thr His Tyr Gly Asn Ser Tyr Leu Asp Gly His
                245                 250                 255

Arg Val His Asn Ala Phe Val Asn Arg Asn Tyr Thr Val Lys Tyr Glu
            260                 265                 270

Val Asn Trp Lys Thr His Glu Ile Lys Val Lys Gly Gln Asn
        275                 280                 285
```

<210> SEQ ID NO 15
<211> LENGTH: 900
<212> TYPE: DNA
<213> ORGANISM: Staphylococcus aureus

<400> SEQUENCE: 15
gcggaaggca aaattacccc ggtctcggtg aaaaagttg acgacaaagt gacgctgtat         60
aaaacgacgg ccacggctga ttcggataaa tttaaaatta gccagatcct gaccttcaac      120
ttcatcaaag ataatctta cgataaagac accctggtgc tgaaagcaac gggcaacatc       180
aatagcggtt tgttaaacc gaacccgaat gattacgact tctcaaaact gtattgggc        240

```
gcaaaataca atgtttcgat tagctctcag agtaacgatt ccgtcaatgt ggttgactat    300
gctccgaaaa accaaaatga agaatttcag gtgcaaaaca ccctgggtta cacgttcggc    360
ggtgatattt caatctcgaa tggcctgagt ggcggtctga acggtaatac cgcgttttcc    420
gaaacgatta actataaaca ggaaagctac cgtaccacgc tgtctcgcaa caccaattat    480
aaaaatgtcg gctggggtgt ggaagcccat aaaatcatga acaatggctg gggtccgtat    540
ggccgtgact cctttcaccc gacgtacggc aacgaactgt tcctggcagg tcgccagagt    600
tccgcatatg caggtcaaaa tttattgcc cagcatcaaa tgccgctgct gagccgttct    660
aactttaatc cggaattcct gtcagtcctg tcgcaccgcc aggatggcgc gaaaaaatct    720
aaaatcaccg ttacgtacca gcgtgaaatg gacctgtacc aaatccgctg gaacggcttc    780
tattgggcag gtgctaacta caaaaacttc aaaacccgta cgttcaaatc tacctatgaa    840
atcgattggg aaaaccacaa agtcaaactg ctggacacga agaaacggaa aaataataaa    900
```

<210> SEQ ID NO 16
<211> LENGTH: 300
<212> TYPE: PRT
<213> ORGANISM: Staphylococcus aureus

<400> SEQUENCE: 16

```
Ala Glu Gly Lys Ile Thr Pro Val Ser Val Lys Val Asp Asp Lys
1               5                   10                  15

Val Thr Leu Tyr Lys Thr Thr Ala Thr Ala Asp Ser Asp Lys Phe Lys
            20                  25                  30

Ile Ser Gln Ile Leu Thr Phe Asn Phe Ile Lys Asp Lys Ser Tyr Asp
        35                  40                  45

Lys Asp Thr Leu Val Leu Lys Ala Thr Gly Asn Ile Asn Ser Gly Phe
    50                  55                  60

Val Lys Pro Asn Pro Asn Asp Tyr Asp Phe Ser Lys Leu Tyr Trp Gly
65                  70                  75                  80

Ala Lys Tyr Asn Val Ser Ile Ser Ser Gln Ser Asn Asp Ser Val Asn
                85                  90                  95

Val Val Asp Tyr Ala Pro Lys Asn Gln Asn Glu Glu Phe Gln Val Gln
            100                 105                 110

Asn Thr Leu Gly Tyr Thr Phe Gly Gly Asp Ile Ser Ile Ser Asn Gly
        115                 120                 125

Leu Ser Gly Gly Leu Asn Gly Asn Thr Ala Phe Ser Glu Thr Ile Asn
    130                 135                 140

Tyr Lys Gln Glu Ser Tyr Arg Thr Thr Leu Ser Arg Asn Thr Asn Tyr
145                 150                 155                 160

Lys Asn Val Gly Trp Gly Val Glu Ala His Lys Ile Met Asn Asn Gly
                165                 170                 175

Trp Gly Pro Tyr Gly Arg Asp Ser Phe His Pro Thr Tyr Gly Asn Glu
            180                 185                 190

Leu Phe Leu Ala Gly Arg Gln Ser Ala Tyr Ala Gly Gln Asn Phe
        195                 200                 205

Ile Ala Gln His Gln Met Pro Leu Leu Ser Arg Ser Asn Phe Asn Pro
    210                 215                 220

Glu Phe Leu Ser Val Leu Ser His Arg Gln Asp Gly Ala Lys Lys Ser
225                 230                 235                 240

Lys Ile Thr Val Thr Tyr Gln Arg Glu Met Asp Leu Tyr Gln Ile Arg
                245                 250                 255
```

Trp Asn Gly Phe Tyr Trp Ala Gly Ala Asn Tyr Lys Asn Phe Lys Thr
            260                 265                 270

Arg Thr Phe Lys Ser Thr Tyr Glu Ile Asp Trp Glu Asn His Lys Val
        275                 280                 285

Lys Leu Leu Asp Thr Lys Glu Thr Glu Asn Asn Lys
        290                 295                 300

<210> SEQ ID NO 17
<211> LENGTH: 971
<212> TYPE: DNA
<213> ORGANISM: Staphylococcus aureus

<400> SEQUENCE: 17

```
aactcggctc ataaagatag tcaggatcaa aataaaaaag aacacgtgga taaatcacaa      60
cagaaagata aacgcaatgt caccaataaa gataaaaata gcaccgcacc ggatgacatt     120
ggcaaaaacg gtaaaatcac caaacgtacc gaaacggtgt atgatgaaaa aacgaatatt     180
ctgcagaacc tgcaatttga tttcatcgat gacccgacct acgacaaaaa tgtgctgctg     240
gttaaaaaac agggcagcat tcattctaac ctgaaattcg aaagtcacaa agaagagaaa     300
aactccaact ggctgaaata tccgtcagaa taccatgtcg atttccaggt gaaacgtaat     360
cgcaaaaccg aaattctgga ccaactgccg aaaaacaaaa tcagtaccgc caaagttgat     420
agtacgtttt cctatagctc tggcggtaaa ttcgactcta ccaaaggcat cggtcgtacg     480
agttccaact catactcgaa aaccatctcg tacaaccagc aaaactacga tacgatcgca     540
agcggcaaaa acaataactg gcatgttcac tggtctgtca ttgctaacga tctgaaatat     600
ggcggtgaag ttaaaaatcg caacgacgaa ctgctgtttt accgtaatac ccgcatcgcg     660
acggtcgaaa acccggaact gtcattcgcg tcgaaatatc gttacccggc cctggtgcgc     720
tccggtttta atccggaatt cctgacctac ctgagcaacg aaaaatctaa cgaaaaaacg     780
cagttcgaag tcacctatac gcgtaatcaa gatattctga aaaaccgtcc gggcattcac     840
tacgcaccgc cgatcctgga aaaaacaaa gatggtcagc gcctgatcgt gacctatgaa     900
gttgactgga aaacaaaac cgtgaaagtg gtggacaaat actcggacga caataaaccg     960
tacaaagaag g                                                         971
```

<210> SEQ ID NO 18
<211> LENGTH: 323
<212> TYPE: PRT
<213> ORGANISM: Staphylococcus aureus

<400> SEQUENCE: 18

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Ala Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

```
Val Asp Phe Gln Val Lys Arg Asn Arg Lys Thr Glu Ile Leu Asp Gln
            115                 120                 125

Leu Pro Lys Asn Lys Ile Ser Thr Ala Lys Val Asp Ser Thr Phe Ser
        130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Ile Leu Glu Lys
        275                 280                 285

Asn Lys Asp Gly Gln Arg Leu Ile Val Thr Tyr Glu Val Asp Trp Lys
        290                 295                 300

Asn Lys Thr Val Lys Val Val Asp Lys Tyr Ser Asp Asp Asn Lys Pro
305                 310                 315                 320

Tyr Lys Glu

<210> SEQ ID NO 19
<211> LENGTH: 927
<212> TYPE: DNA
<213> ORGANISM: Staphylococcus aureus

<400> SEQUENCE: 19
aaaatcaaca gcgaaatcaa acaagtcagc gaaaaaaatc tggatggcga tacgaaaatg      60
tacacgcgca cggcaaccac gagcgattcg cagaaaaaca tcacccagag cctgcaattt     120
aatttcctga ccgaaccgaa ctacgataaa gaaacggtgt catcaaagc aaaaggcacc      180 atcggctcag tctgcgtat tctggacccg aatggctact ggaactcgac cctgcgctgg      240
ccgggtagct attctgtgag tattcagaat gttgatgaca acaataacac caacgttacg     300
gattttgctc cgaaaaatca agatgaaagc cgtgaagtca atataccta cggctataaa      360 acgggcggtg atttctctat caatcgcggc ggtctgaccg gtaatattac gaaagaatcg     420
aactatagcg aaaccatctc ctaccagcaa ccgtcatatc gtaccctgct ggatcagtcc     480
acgtcacata aaggcgttgg ttggaaagtc gaagcgcacc tgatcaataa catgggccat     540
gatcacaccc gtcaactgac gaatgatagc gacaaccgca cgaaatctga aattttagt     600 ctgacccgca atggtaacct gtgggcgaaa gataacttca cgccgaaaga caaaatgccg     660
gtcaccgtgt ccgaaggctt taatccggaa ttcctggccg ttatgtctca tgataaaaaa     720
gacaaaggta aaagtcagtt cgtggttcac tacaaacgtt ccatggatga attcaaaatc     780
gactggaacc gccatggctt ctggggttac tggagcggtg aaaaccacgt cgataaaaaa     840
gaagaaaaac tgtctgcact gtatgaagtg gactggaaaa cccacaatgt caaattcgtg     900
```
aaagttctga atgataatga aaaaaaa                                              927

<210> SEQ ID NO 20
<211> LENGTH: 309
<212> TYPE: PRT
<213> ORGANISM: Staphylococcus aureus

<400> SEQUENCE: 20

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 21
<211> LENGTH: 966
<212> TYPE: DNA
<213> ORGANISM: Staphylococcus aureus

<400> SEQUENCE: 21

-continued

```
gcaaacaagg actcccagga ccagaccaaa aaagaacacg tcgataaagc acagcagaaa    60
gaaaagcgta atgtcaacga taaagataaa aataccccgg gcccggatga cattggcaaa   120
aacggcaagg ttaccaaacg taccgtcagt gaatatgaca agaaaccaa tattctgcag    180 aacctgcaat tgatttcat cgatgacccg acgtacgaca aaaatgtgct gctggttaaa    240
aagcaaggta gtatccattc aacctgaag tttgaaagcc accgtaatga aaccaacgcg    300
agttggctga atatccgtc cgaataccat gtcgatttcc aggtgcaacg caatccgaaa    360
acggaaattc tggaccagct gccgaaaaac aagatctcaa ccgcaaaagt ggattcgacg   420
tttagttatt ccctgggcgg taaattcgac agcaccaaag gcattggtcg caccagcagc   480
aacagctact cgaagagcat ctcttacaac cagcaaaact acgataccat cgcaagcggc   540
aaaaacaata accgtcatgt tcactggtct gtggttgcta atgatctgaa gtatggtaac   600
gaaatcaaaa atcgcaacga cgaatttctg ttctaccgta atcccgcct gagtacggtc   660 gaaaaccccgg aactgtcatt tgcgtcgaaa tatcgttacc cggccctggt tcgctccggc   720
tttaatccgg aatttctgac ctacatcagc aacgaaaagt ctaacgaaaa gacgcgtttc   780
gaagtgacct atacgcgcaa tcaggatatc ctgaaaaaca gcccgggcat tcactacggt   840
cagccgatcc tggaacaaaa caaagatggc cagcgtttta ttgtcgtgta tgaagtggac   900
tggaaaaata gaccgttaa ggttgtcgaa aaatattctg atcagaacaa gccgtacaaa   960
gaaggt                                                               966
```

<210> SEQ ID NO 22
<211> LENGTH: 322
<212> TYPE: PRT
<213> ORGANISM: Staphylococcus aureus

<400> SEQUENCE: 22

```
Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Lys Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Val Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ser Thr Phe Ser Tyr Ser
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Val Val
            180                 185                 190

Ala Asn Asp Leu Lys Tyr Gly Asn Glu Ile Lys Asn Arg Asn Asp Glu
```

```
            195                 200                 205
Phe Leu Phe Tyr Arg Asn Thr Arg Leu Ser Thr Val Glu Asn Pro Glu
        210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Ser Asn Glu
            245                 250                 255

Lys Thr Arg Phe Glu Val Thr Tyr Thr Arg Asn Gln Asp Ile Leu Lys
        260                 265                 270

Asn Lys Pro Gly Ile His Tyr Gly Gln Pro Ile Leu Glu Gln Asn Lys
    275                 280                 285

Asp Gly Gln Arg Phe Ile Val Val Tyr Glu Val Asp Trp Lys Asn Lys
        290                 295                 300

Thr Val Lys Val Val Glu Lys Tyr Ser Asp Gln Asn Lys Pro Tyr Lys
305                 310                 315                 320

Glu Gly
```

<210> SEQ ID NO 23
<211> LENGTH: 945
<212> TYPE: DNA
<213> ORGANISM: Staphylococcus aureus

<400> SEQUENCE: 23

```
gcaagctcgt atgcggaaat caaaagcaag atcaccaccg tctcagaaaa gaacctggat    60
ggcgacacca gatgtacac ccgtaccgcg accacgagcg atacggaaaa gaaaattagc    120
cagtctctgc aatttaattt cctgaccgaa ccgaactacg acaagaaac ggtgtttatt    180
aaagccaagg gcaccatcgg cagcggtctg aaaattctga atccgaacgg ctactggaac    240
agcaccctgc gttggccggg tagttattcc gtttcaattc agaacgtcga tgacaacaat    300
aactcaacca atgtcacgga ttttgcaccg aaaaaccaag acgaatcgcg tgaagtgaaa    360
tatacctacg gctataagac gggcggtgat ttcagtatca atcgcggcgg tctgaccggt    420
aacatcacga aggaaaagaa ctactcggaa accatcagct accagcaacc gtcttatcgt    480
accctgattg atcagccgac cacgaataaa ggcgtcgcgt ggaaggtgga agcccatagc    540
atcaataaca tgggtcatga tcacacccgt caactgacga acgactctga tgaccgcgtg    600
aaatctgaaa ttttttagtct gacccgcaat ggcaacctgt gggcaaaaga taatttcacg    660
ccgaaaaaca agatgccggt gaccgtttcc gaaggcttta atccggaatt tctggctgtt    720
atgtcccatg ataaaaacga caaaggtaag tcacgtttca tcgtccacta taaacgctcg    780
atggatgact ttaaactgga ttggaataag catggcttct ggggttactg gagtggtgaa    840
aaccacgttg accagaaaga agaaaagctg tccgccctgt atgaagtgga ttggaaaacg    900
cacgacgtta aactgattaa gaccatcaac gataaagaac agaag              945
```

<210> SEQ ID NO 24
<211> LENGTH: 315
<212> TYPE: PRT
<213> ORGANISM: Staphylococcus aureus

<400> SEQUENCE: 24

```
Ala Ser Ser Tyr Ala Glu Ile Lys Ser Lys Ile Thr Thr Val Ser Glu
1               5                   10                  15

Lys Asn Leu Asp Gly Asp Thr Lys Met Tyr Thr Arg Thr Ala Thr Thr
            20                  25                  30
```

Ser Asp Thr Glu Lys Lys Ile Ser Gln Ser Leu Gln Phe Asn Phe Leu
    35                  40                  45

Thr Glu Pro Asn Tyr Asp Lys Glu Thr Val Phe Ile Lys Ala Lys Gly
50                  55                  60

Thr Ile Gly Ser Gly Leu Lys Ile Leu Asn Pro Asn Gly Tyr Trp Asn
65                  70                  75                  80

Ser Thr Leu Arg Trp Pro Gly Ser Tyr Ser Val Ser Ile Gln Asn Val
            85                  90                  95

Asp Asp Asn Asn Asn Ser Thr Asn Val Thr Asp Phe Ala Pro Lys Asn
                100                 105                 110

Gln Asp Glu Ser Arg Glu Val Lys Tyr Thr Tyr Gly Tyr Lys Thr Gly
            115                 120                 125

Gly Asp Phe Ser Ile Asn Arg Gly Gly Leu Thr Gly Asn Ile Thr Lys
    130                 135                 140

Glu Lys Asn Tyr Ser Glu Thr Ile Ser Tyr Gln Gln Pro Ser Tyr Arg
145                 150                 155                 160

Thr Leu Ile Asp Gln Pro Thr Thr Asn Lys Gly Val Ala Trp Lys Val
                165                 170                 175

Glu Ala His Ser Ile Asn Asn Met Gly His Asp His Thr Arg Gln Leu
            180                 185                 190

Thr Asn Asp Ser Asp Asp Arg Val Lys Ser Glu Ile Phe Ser Leu Thr
    195                 200                 205

Arg Asn Gly Asn Leu Trp Ala Lys Asp Asn Phe Thr Pro Lys Asn Lys
210                 215                 220

Met Pro Val Thr Val Ser Glu Gly Phe Asn Pro Glu Phe Leu Ala Val
225                 230                 235                 240

Met Ser His Asp Lys Asn Asp Lys Gly Lys Ser Arg Phe Ile Val His
                245                 250                 255

Tyr Lys Arg Ser Met Asp Asp Phe Lys Leu Asp Trp Asn Lys His Gly
            260                 265                 270

Phe Trp Gly Tyr Trp Ser Gly Glu Asn His Val Asp Gln Lys Glu Glu
    275                 280                 285

Lys Leu Ser Ala Leu Tyr Glu Val Asp Trp Lys Thr His Asp Val Lys
290                 295                 300

Leu Ile Lys Thr Ile Asn Asp Lys Glu Gln Lys
305                 310                 315

<210> SEQ ID NO 25
<211> LENGTH: 954
<212> TYPE: DNA
<213> ORGANISM: Staphylococcus aureus

<400> SEQUENCE: 25
gactcacagg accaaaacaa aaaggaacac gttgataagg cacagcagaa agacaagcaa    60
gatagcacca agaaaggcaa aaacgttgcg gccccggatg acgtcggcaa aaacggcaag   120
gtgaccaaac gtacggaaag cgaatacgat gaaaagacca catcctgca gaacctggaa    180 tttaatttca tcgatgaccc gacctacgat aaagacgtcc tgctggtgaa aaagcaaggc   240
agtattcatt ccaacctgaa gttcgaaagt cacaaagaag aaaagaacag cacctggctg   300
aaatatccgt cagaatacca tgttgatttc caggtcaagc gtaacccgaa accgaaatt    360 ctggaccaac tgccgaaaaa taagatcagt acggcaaaag tggattcaac cttttcgtat   420
acgctgggcg gtaaattcga ctccattaaa ggcatcggtc gcaatagctc taacagctat   480
tctcagacca tttcgtataa tcagcaaaac tacgatacga tcgcgagcgg caaaaacaat   540

```
aactggcatg tgcactggtc tgttattgcc aacgatctga agtatggcgg tgaagttaaa    600
aatcgtaacg acgaatttct gttctaccgt aacacccgca cgagttccgt tgataatccg    660
gaatcatcgt ttgcagctaa atatcgttac ccggcactgg tccgcagtgg ttttaatccg    720
gaatttctga cctatctgag caacgaaaag tctaatgaaa aaacgcagtt tgaagtgacc    780
tatacgcgta accaagatat cctgaaaaat agcccgggcc tgcattacgc tccgccgatt    840
ctggaaaaga acaaggttgg tcaccgcttt atcgtcacct atgaagtgga ttggaaaaat    900
aagacggtga aggtggttga caaatactct gatgaccagc cgttccgcga aggt          954
```

<210> SEQ ID NO 26
<211> LENGTH: 318
<212> TYPE: PRT
<213> ORGANISM: Staphylococcus aureus

<400> SEQUENCE: 26

Asp Ser Gln Asp Gln Asn Lys Lys Glu His Val Asp Lys Ala Gln Gln
 1               5                  10                  15

Lys Asp Lys Gln Asp Ser Thr Lys Lys Gly Lys Asn Val Ala Ala Pro
            20                  25                  30

Asp Asp Val Gly Lys Asn Gly Lys Val Thr Lys Arg Thr Glu Ser Glu
        35                  40                  45

Tyr Asp Glu Lys Thr Asn Ile Leu Gln Asn Leu Glu Phe Asn Phe Ile
    50                  55                  60

Asp Asp Pro Thr Tyr Asp Lys Asp Val Leu Leu Val Lys Lys Gln Gly
65                  70                  75                  80

Ser Ile His Ser Asn Leu Lys Phe Glu Ser His Lys Glu Glu Lys Asn
                85                  90                  95

Ser Thr Trp Leu Lys Tyr Pro Ser Glu Tyr His Val Asp Phe Gln Val
            100                 105                 110

Lys Arg Asn Pro Lys Thr Glu Ile Leu Asp Gln Leu Pro Lys Asn Lys
        115                 120                 125

Ile Ser Thr Ala Lys Val Asp Ser Thr Phe Ser Tyr Thr Leu Gly Gly
    130                 135                 140

Lys Phe Asp Ser Ile Lys Gly Ile Gly Arg Asn Ser Ser Asn Ser Tyr
145                 150                 155                 160

Ser Gln Thr Ile Ser Tyr Asn Gln Gln Asn Tyr Asp Thr Ile Ala Ser
                165                 170                 175

Gly Lys Asn Asn Asn Trp His Val His Trp Ser Val Ile Ala Asn Asp
            180                 185                 190

Leu Lys Tyr Gly Gly Glu Val Lys Asn Arg Asn Asp Glu Phe Leu Phe
        195                 200                 205

Tyr Arg Asn Thr Arg Thr Ser Ser Val Asp Asn Pro Glu Ser Ser Phe
    210                 215                 220

Ala Ala Lys Tyr Arg Tyr Pro Ala Leu Val Arg Ser Gly Phe Asn Pro
225                 230                 235                 240

Glu Phe Leu Thr Tyr Leu Ser Asn Glu Lys Ser Asn Glu Lys Thr Gln
                245                 250                 255

Phe Glu Val Thr Tyr Thr Arg Asn Gln Asp Ile Leu Lys Asn Ser Pro
            260                 265                 270

Gly Leu His Tyr Ala Pro Pro Ile Leu Glu Lys Asn Lys Val Gly His
        275                 280                 285

Arg Phe Ile Val Thr Tyr Glu Val Asp Trp Lys Asn Lys Thr Val Lys
    290                 295                 300

Val Val Asp Lys Tyr Ser Asp Asp Gln Pro Phe Arg Glu Gly
305                 310                 315

<210> SEQ ID NO 27
<211> LENGTH: 927
<212> TYPE: DNA
<213> ORGANISM: Staphylococcus aureus

<400> SEQUENCE: 27

```
aaaatcaaat cggaaatcac gcaagttagc gaacagaata tcgacggcaa tacgaagatg     60
tttacccgca cggcaacgac ctcggatagc cagaaaaaga tcagccagtc tctgcaattt    120
aacttcctga ccgaaccgaa ctacgacaag gaaacggtgt tcatcaaggc aaagggcacc    180
atcggctctg gtctgaaaat tctggacccg aacggctact ggaatagtac cctgcgttgg    240
ccgggtagtt attccgtgtc aatccagaac gttgataaca ataccaatac gaaggttacg    300
gattttgccc cgaaaaacca agacgaaacc cgcgaagtca agtataccta cggctataaa    360
acgggcggtg atttctcgat tagcccgggc ggtattaccg gtaacatcac gaaagaacgt    420
aattattctg aaaccatcag ttaccagcaa ccgagttatc gcaccctgat tgaccagccg    480
gcgacgaata agggcgttgg ttggaaagtc gaagcccatc tgatcaacaa tatgggccat    540
gatcacaccc gtcaactgac gaacgattcc gacaatcgcg tgggctcaga aattttacc     600
ctgacgcgta acggtaatct gtgggcgaaa gataacttca cgccgaaaaa taagatgccg    660
gtcaccgtgt ccgaaggctt taacccggaa tttctggccg ttatgtcgca tgataaaaag    720
gacaaaggca agagcaaatt tgtggttcac tataaacgta cgatggatga ctttaaaatc    780
gattggatgc gccatggctt ctggggttac tggaccggta aaaatcacgt tgaccagaag    840
gaagaaaaac tgtctgcact gtatgaagtc gattggaaaa cccacgacgt gaagttcatt    900
aaagctctgg atgacaaaga aaagaaa                                        927
```

<210> SEQ ID NO 28
<211> LENGTH: 309
<212> TYPE: PRT
<213> ORGANISM: Staphylococcus aureus

<400> SEQUENCE: 28

Lys Ile Lys Ser Glu Ile Thr Gln Val Ser Glu Gln Asn Ile Asp Gly
1               5                   10                  15

Asn Thr Lys Met Phe Thr Arg Thr Ala Thr Ser Asp Ser Gln Lys
            20                  25                  30

Lys Ile Ser Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Lys Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asn Asn Thr Asn
                85                  90                  95

Thr Lys Val Thr Asp Phe Ala Pro Lys Asn Gln Asp Glu Thr Arg Glu
            100                 105                 110

Val Lys Tyr Thr Tyr Gly Tyr Lys Thr Gly Gly Asp Phe Ser Ile Ser
        115                 120                 125

Pro Gly Gly Ile Thr Gly Asn Ile Thr Lys Glu Arg Asn Tyr Ser Glu
    130                 135                 140

-continued

```
Thr Ile Ser Tyr Gln Gln Pro Ser Tyr Arg Thr Leu Ile Asp Gln Pro
145                 150                 155                 160

Ala Thr Asn Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Val Gly Ser Glu Ile Phe Thr Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Lys Phe Val Val His Tyr Lys Arg Thr Met Asp
                245                 250                 255

Asp Phe Lys Ile Asp Trp Met Arg His Gly Phe Trp Gly Tyr Trp Thr
            260                 265                 270

Gly Lys Asn His Val Asp Gln Lys Glu Glu Lys Leu Ser Ala Leu Tyr
            275                 280                 285

Glu Val Asp Trp Lys Thr His Asp Val Lys Phe Ile Lys Ala Leu Asp
    290                 295                 300

Asp Lys Glu Lys Lys
305
```